(12) United States Patent
Muto et al.

(10) Patent No.: US 7,598,418 B2
(45) Date of Patent: Oct. 6, 2009

(54) AMIDE DERIVATIVES

(75) Inventors: Susumu Muto, Tokyo (JP); Akiko Itai, Tokyo (JP)

(73) Assignee: Institute of Medicinal Molecular Design, Inc., Tokyo (JP)

( * ) Notice: Subject to any disclaimer, the term of this patent is extended or adjusted under 35 U.S.C. 154(b) by 0 days.

(21) Appl. No.: 10/510,242

(22) PCT Filed: Apr. 18, 2003

(86) PCT No.: PCT/JP03/04986

§ 371 (c)(1),
(2), (4) Date: May 18, 2005

(87) PCT Pub. No.: WO03/086377

PCT Pub. Date: Oct. 23, 2003

(65) Prior Publication Data

US 2005/0215645 A1    Sep. 29, 2005

(30) Foreign Application Priority Data

Apr. 18, 2002    (JP) .............................. 2002-115629

(51) Int. Cl.
| | |
|---|---|
| A61K 31/18 | (2006.01) |
| A61K 31/22 | (2006.01) |
| A61K 31/255 | (2006.01) |
| A61K 31/341 | (2006.01) |
| A61K 31/36 | (2006.01) |
| C07D 235/14 | (2006.01) |
| C07D 307/52 | (2006.01) |
| C07D 317/58 | (2006.01) |

(52) U.S. Cl. .............................. 564/89; 564/88; 564/86; 564/85; 564/84; 564/80

(58) Field of Classification Search .................. None
See application file for complete search history.

(56) References Cited

U.S. PATENT DOCUMENTS

| 4,579,805 A | 4/1986 | Bergthaller et al. |
|---|---|---|
| 5,378,715 A | 1/1995 | Stein et al. |
| 5,399,487 A | 3/1995 | Butenas et al. |
| 5,707,985 A * | 1/1998 | McKenzie et al. .......... 514/183 |
| 6,417,181 B1 * | 7/2002 | Bender et al. ............... 514/183 |

FOREIGN PATENT DOCUMENTS

| EP | 1402890 | 3/2004 |
|---|---|---|
| GB | 827446 | 2/1960 |
| GB | 1364952 | 8/1974 |
| GB | 2397817 | 8/2004 |
| JP | 48-30733 | 4/1973 |
| JP | 60-140240 | 7/1985 |
| JP | 3-217459 | 9/1991 |
| JP | 5-503721 | 6/1993 |
| JP | 6-504052 | 5/1994 |
| JP | 2001-504492 | 4/2001 |
| RU | 1646258 | * 2/1996 |
| WO | 92/07557 | 5/1992 |
| WO | 92/12119 | 7/1992 |
| WO | 98/22125 | 5/1998 |
| WO | WO99/37609 | * 7/1999 |
| WO | 03-035621 | 5/2003 |

OTHER PUBLICATIONS

Marsilje H. T. et al. Bioorganic & Medicinal Chemistry Letters, 2000, vol. 10, pp. 477-481.*
Stein et al. Journal of Medicinal Chemistry 1995, vol. 38, pp. 1344-1354.*
Butenas et al. CAS abstract of: Biochemistry, 1992, vol. 31, pp. 5399-5411.*
The Merck Manual of diagnosis and therapy, 7th edition, 1999, Published by Merch Research Laboratories, pp. 397-398, 948-949, 1916 and 1979-1981.*
CAplus abstract of SU 1646258 published 1996.*
P.R. Graves et al., J. of Biol. Chem., vol. 275, No. 8, Feb. 25, 2000, pp. 5600-5605.
B. Hu et al., J. Biol. Chem., vol. 276, No. 21, May 25, 2001, pp. 17693-17698.

(Continued)

Primary Examiner—Paul A Zucker
Assistant Examiner—Yevegeny Valenrod
(74) Attorney, Agent, or Firm—Greenblum & Bernstein, P.L.C.

(57) ABSTRACT

A medicament for enhancing an effect of a cancer therapy based on a mode of action of DNA injury, which comprises as an active ingredient a compound represented by the following general formula (I) or a salt thereof:

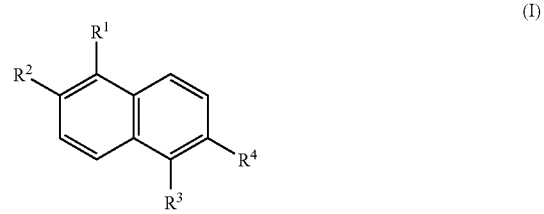

(I)

wherein one of $R^1$ and $R^2$ represents hydrogen atom and the other represents the formula —X-A wherein A represents hydrogen atom or an acyl group, X represents oxgen atom or NH; one of $R^3$ and $R^4$ represents hydrogen atom and the other represents the following formula:

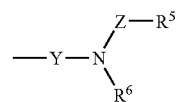

wherein Y represents a sulfonyl group or a carbonyl group, $R^5$ represents a cyclic group, Z represents a single bond or a $C_1$ to $C_4$ alkylene group, $R^6$ represents hydrogen atom or a $C_1$ to $C_6$ alkyl group.

21 Claims, No Drawings

OTHER PUBLICATIONS

K. Tomita et al., Jpn. J. Cancer Res., vol. 80, Jan. 1989, pp. 83-88.
A. Monks et al., Invest. New Drugs, vol. 18, 2000, pp. 95-107.
E.C. Busby et al., Cancer Res., vol. 60, Apr. 15, 2000, pp. 2108-2112.
J.N. Sarkaria et al., Cancer Res., vol. 59, Sep. 1, 1999, pp. 4375-4382.
B.-B.S. Zhou et al., J. Biol. Chem., vol. 275, No. 14, Apr. 7, 2000, pp. 10342-10348.
Z. Shi et al., Cancer Res., vol. 61, Feb. 1, 2001, pp. 1065-1072.
K. Kawakami et al., Biochem. Biophys. Res. Commun., vol. 219, 1996.
W.-Y. Wang et al., Acta Pharmacol Sin, vol. 21, No. 1, Jan. 2000, pp. 35-40.
J. Bendig et al., Tetrahedron, vol. 48, No. 42, 1992, pp. 9207-9216.
S.R. Wilson et al., Tetrahedron, vol. 49, No. 17, 1993, pp. 3655-3663.
R.D. Desai et al., Jour. Indian Chem. Soc., vol. 46, No. 5, 1969, pp. 411-415.
S. Fujita et al., Anal. Chem., vol. 66, 1994, pp. 1347-1353.
English Language Abstract of JP 3-217459, Published Sep. 25, 1991.
U.S. Appl. No. 10/478,687.
U.S. Appl. No. 10/488,254.
Gebauer-Fülnegg and Glückmann, *Monatshefte fuer Chemie* vol. 53-54: pp. 100-110 (1929).

* cited by examiner

AMIDE DERIVATIVES

FIELD OF INVENTION

The present invention relates to medicaments for enhancing the effect of cancer therapy on the basis of mechanism of injuring DNA, and novel compounds useful as active ingredients of said medicament.

BACKGROUND ART

Anticancer agents are administered in treatments of cancer patients at present. However, their life-prolongation rates are undesirably low, and moreover, cancer patients administered with an anticancer agent are forced to tolerate severe side effects such as fever, nausea, epilation, chill, fatigue, immune malfunction, gastrointestinal disorder, liver disorder, and kidney disorder, which becomes a cause of significant deterioration of the QOL (Quality of Life) of the cancer patients. Furthermore, reduction of sensitivity of cancer cells to anticancer agents, caused by the use of the anticancer agents, may lead to prolonged administration period of administration of the anticancer agents and increase of doses, and as a result, deaths resulting from side effects of the anticancer agents are often observed. Therefore, the administration of anticancer agents may spoil advantages of patients, as well as significantly diminish social and economic benefits. This is caused by the fact that anticancer agents, which are expectedly used to exhibit selective cytotoxicity to cancer cells that disorderly divide and proliferate, actually act cytotoxically on normal cells, particularly on cells in the intestine and marrow.

In recent years, reports have been made on caffeine which is a low molecule organic compound and UCN-01(7-hydroxy staurosporine) having actions to enhance radiation susceptibility of cancer cells which are radiation resistant (J. Biol. Chem., 275, 5600-5605, 2000; J. Biol. Chem., 276, 17693-17698, 2001). Cancer therapy by radiation is also based on the mode of action of artificial injury of DNAs, and is considered to be basically equivalent to anticancer agents such as bleomycin based on the mode of action of DNA injury. Accordingly, it is believed that a drug that enhances selective toxicity to cancer cells can be developed even for anticancer agents based on the mode of action of DNA injury which are available at present.

In fact, it is reported that caffeine increases the actions of anticancer agents such as adriamycin, cisplatin, cyclophosphamide, and mitomycin C based on the mode of action of DNA injury (Jpn. J. Cancer. Res., 80, 83-88, 1989). However, potency remains insufficient, and separation from toxicity is unsatisfactory. UCN-01 is also reported to enhance actions of several kinds of anticancer agents based on the mode of action of DNA injury (Invest. New Drugs, 18, 95-107, 2000).

As for the mode of action of the potentiation of anticancer agents, the action is presumed to be based on a destruction of a certain part of the cell cycle (for example, G1 period and G2 period: Cancer Res., 60, 2108-2112, 2000; Cancer Res., 59, 4375-4382(1999), since caffeine and UCN-01 inhibit protein kinases involved in a control of a cell cycle (J. Biol. Chem., 275, 10342-10348, 2000; Cancer Res., 61, 1065-1072, 2001). However, no conclusive evidence has been obtained. In addition, since caffeine and UNC-01 as a staurosporin derivative have inhibitory actions against multiple kinds of protein kinases (Biochem. Biophys. Res. Commun., 219, 778-783, 1996; Acta Pharmacol. Sin., 21, 35-40, 2000), a possibility of involvement of a mechanism other than the destruction of the cell cycle can not be denied. Accordingly, a clear mode of action remains unidentified. Furthermore, there is a high possibility that these agents have inhibitory actions also against protein kinases participating in intracellular signal transduction, which is considered to be a possible cause of inducing serious side effects.

As explained above, no effective means is available at present to solve various problems caused by the cancer therapies based on the mode of action of DNA injury. Developments of new drugs or therapies, that potentiate the effects of available anticancer agents and radiation therapy based on the mode of action of DNA injury and that enhance selectivity to cancer cells to decrease side effects, will contribute to increase the QOL and advantages of cancer patients as well as social and economic benefits.

DISCLOSURE OF THE INVENTION

An object of the present invention is to provide medicaments for enhancing the effect of cancer therapy based on the mode of action of DNA injury. More specifically, an object of the present invention is to provide medicaments which, per se, have weak anticancer activity (cytotoxicity), but in combination of an anticancer agent based on the mode of action of DNA injury or a therapy such as radiation which gives artificial injuries to DNA, can selectively damage or kill cancer cells at a lower dose of anticancer agent or a lower radiation dose so as to significantly reduce affects on normal cells. Furthermore, another object of the present invention is to provide medicaments to reduce side effects resulting from cancer therapy by potentiation of the effects of the above cancer therapy and by reduction of a dose of the anticancer agent and/or radiation dose. Still further object of the present invention is to provide novel compounds which are useful as active ingredients of the above medicaments.

The inventors of the present invention focused on protein kinase inhibitors to solve the aforementioned objects, and carried out search for compounds having desired pharmacological activities by using computerized molecular design technology as a means to discover candidate compounds. The inventors carried out an automatic search program of a ligand from a three-dimensional compound database based on the three-dimensional structure of the protein by using the ATP binding regions of several kinds of protein kinases whose structures are registered in PDB (Protein Data Bank), and by virtual screenings, they selected compounds having potentials as protein kinase inhibitors from compounds registered in databases of commercial compounds. The inventors classified the resulting compounds on the basis of their skeletons, and by using several typical compounds, they carried out tests of combined effects with bleomycin on cancer cells and normal cells and tests of cytotoxicity to cancer cells and normal cells when the compounds are used alone. The inventors selected compounds having strong and desired pharmacological activities, and further prepared their derivatives to achieve the present invention.

The present invention thus provides a medicament for enhancing an effect of a cancer therapy based on a mode of action of DNA injury which comprises as an active ingredient a substance selected from the group consisting of a compound represented by the following general formula (I) and a pharmacologically acceptable salt thereof, and a hydrate thereof and a solvate thereof:

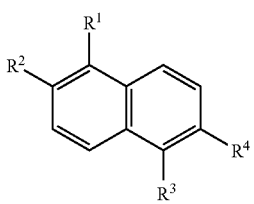

wherein one of R¹ and R² represents hydrogen atom and the other represents the formula —X-A wherein A represents hydrogen atom or an acyl group, X represents oxygen atom or NH; one of R³ and R⁴ represents hydrogen atom and the other represents the following formula:

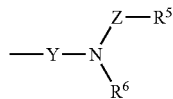

wherein Y represents a sulfonyl group or a carbonyl group, R⁵ represents a cyclic group which may be substituted, Z represents a single bond or a $C_1$ to $C_4$ alkylene group which may be substituted, or when Z is substituted, said substituent may bind to R⁵ to form a ring group, R⁶ represents hydrogen atom or a $C_1$ to $C_6$ alkyl group which may be substituted, or R⁶ may bind to Z or R⁵ to form a cyclic group, provided that the compound represented by the following formula:

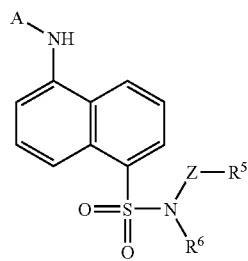

wherein each of A, Z, R⁵ and R⁵ has the same meaning as that defined above is excluded.

According to preferred embodiments of the aforementioned invention, provided are the aforementioned medicament wherein R⁵ is an aromatic ring group which may be substituted; the aforementioned medicament wherein Z is a methylene group which may be substituted, or when Z is substituted, said substituent may bind to R⁵ to form a ring group; the aforementioned medicament wherein Y is a sulfonyl group; and the aforementioned medicament wherein R¹ is a group represented by the formula —O-A wherein A represents hydrogen atom or an acyl group, and R² is hydrogen atom.

Furthermore, according to preferred embodiments of the aforementioned invention, provided are the aforementioned medicament wherein the cancer therapy based on the mode of action of DNA injury is carried out by administration of an anticancer agent and/or radiation; the aforementioned medicament wherein the anticancer agent is selected from a group consisting of bleomycin, adriamycin, cisplatin, cyclophosphamide, mitomycin C, and their derivatives; and the aforementioned medicament which is a specific inhibitor against a protein kinase and/or its analogous enzyme.

From another aspect, the present invention provides a medicament for reducing a side effect resulting from a cancer therapy based on the mode of action of DNA injury which comprises as an active ingredient a compound represented by the aforementioned general formula (I) or a physiologically acceptable salt thereof.

From further another aspect, the present invention provides use of the compound represented by the aforementioned general formula (I) or the physiologically acceptable salt thereof for manufacture of the aforementioned medicament; a method of enhancing an effect of cancer therapy based on the mode of action of DNA injury in a mammal including a human, which comprises the step of applying a cancer therapy based on the mode of action of DNA injury to a cancer patient, and the step of administering the compound represented by the aforementioned general formula (I) or the physiologically acceptable salt thereof at a dose sufficient to potentiate the effect of the aforementioned cancer therapy; a method of reducing a side effect resulting from a cancer therapy based on the mode of action of DNA injury in a mammal including a human, which comprises the step of applying a cancer therapy based on the mode of action of DNA injury to a cancer patient, and the step of administering the compound represented by the aforementioned general formula (I) or the physiologically acceptable salt thereof at a dose sufficient to reduce the side effect of the aforementioned cancer therapy.

Furthermore, the present invention provides a compound represented by the aforementioned general formula (I) or a pharmacologically acceptable salt thereof, or a hydrate thereof or a solvate thereof, provided that the following compound is excluded.

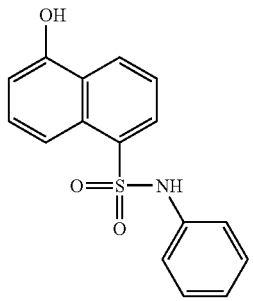

BEST MODE FOR CARRYING OUT THE INVENTION

The terms used in the present specification have the following meanings.

As the halogen atom, any of fluorine atom, chlorine atom, bromine atom, or iodine atom may be used unless otherwise specifically referred to.

Examples of the hydrocarbon group include, for example, an aliphatic hydrocarbon group, an aryl group, an arylene group, an aralkyl group, a bridged cyclic hydrocarbon group, a spiro cyclic hydrocarbon group, and a terpene hydrocarbon.

Examples of the aliphatic hydrocarbon group include, for example, alkyl group, alkenyl group, alkynyl group, alkylene group, alkenylene group, alkylidene group and the like which are straight chain or branched chain monovalent or bivalent acyclic hydrocarbon groups; cycloalkyl group, cycloalkenyl group, cycloalkanedienyl group, cycloalkyl-alkyl group, cycloalkylene group, and cycloalkenylene group, which are saturated or unsaturated monovalent or bivalent alicyclic hydrocarbon groups.

Examples of the alkyl group include, for example, methyl, ethyl, n-propyl, isopropyl, n-butyl, isobutyl, sec-butyl, tert-butyl, n-pentyl, isopentyl, 2-methylbutyl, 1-methylbutyl, neopentyl, 1,2-dimethylpropyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-ethylbutyl, 1-ethyl-1-methylpropyl, n-heptyl, n-octyl, n-nonyl, n-decyl, n-undecyl, n-dodecyl, n-tridecyl, n-tetradecyl, and n-pentadecyl, which are $C_1$ to $C_{15}$ straight chain or branched chain alkyl groups.

Examples of the alkenyl group include, for example, vinyl, prop-1-en-1-yl, allyl, isopropenyl, but-1-en-1-yl, but-2-en-1-yl, but-3-en-1-yl, 2-methylprop-2-en-1-yl, 1-methylprop-2-en-1-yl, pent-1-en-1-yl, pent-2-en-1-yl, pent-3-en-1-yl, pent-4-en-1-yl, 3-methylbut-2-en-1-yl, 3-methylbut-3-en-1-yl, hex-1-en-1-yl, hex-2-en-1-yl, hex-3-en-1-yl, hex-4-en-1-yl, hex-5-en-1-yl, 4-methylpent-3-en-1-yl, 4-methylpent-3-en-1-yl, hept-1-en-1-yl, hept-6-en-1-yl, oct-1-en-1-yl, oct-7-en-1-yl, non-1-en-1-yl, non-8-en-1-yl, dec-1-en-1-yl, dec-9-en-1-yl, undec-1-en-1-yl, undec-10-en-1-yl, dodec-1-en-1-yl, dodec-11-en-1-yl, tridec-1-en-1-yl, tridec-12-en-1-yl, tetradec-1-en-1-yl, tetradec-13-en-1-yl, pentadec-1-en-1-yl, and pentadec-14-en-1-yl, which are $C_2$ to $C_{15}$ straight chain or branched chain alkenyl groups.

Examples of the alkynyl group include, for example, ethynyl, prop-1-yn-1-yl, prop-2-yn-1-yl, but-1-yn-1-yl, but-3-yn-1-yl, 1-methylprop-2-yn-1-yl, pent-1-yn-1-yl, pent-4-yn-1-yl, hex-1-yn-1-yl, hex-5-yn-1-yl, hept-1-yn-1-yl, hept-6-yn-1-yl, oct-1-yn-1-yl, oct-7-yn-1-yl, non-1-yn-1-yl, non-8-yn-1-yl, dec-1-yn-1-yl, dec-9-yn-1-yl, undec-1-yn-1-yl, undec-10-yn-1-yl, dodec-1-yn-1-yl, dodec-11-yn-1-yl, tridec-1-yn-1-yl, tridec-12-yn-1-yl, tetradec-1-yn-1-yl, tetradec-13-yn-1-yl, pentadec-1-yn-1-yl, and pentadec-14-yn-1-yl, which are $C_2$ to $C_{15}$ straight chain or branched chain alkynyl groups.

Examples of the alkylene group include, for example, methylene, ethylene, ethane-1,1-diyl, propane-1,3-diyl, propane-1,2-diyl, propane-2,2-diyl, butane-1,4-diyl, pentane-1,5-diyl, hexane-1,6-diyl, and 1,1,4,4-tetramethylbutane-1,4-diyl group, which are $C_1$ to $C_8$ straight chain or branched chain alkylene groups.

Examples of the alkenylene group include, for example, ethene-1,2-diyl, propene-1,3-diyl, but-1-ene-1,4-diyl, but-2-ene-1,4-diyl, 2-methylpropene-1,3-diyl, pent-2-ene-1,5-diyl, and hex-3-ene-1,6-diyl, which are $C_1$ to $C_6$ straight chain or branched chain alkylene groups.

Examples of the alkylidene group include, for example, methylidene, ethylidene, propylidene, isopropylidene, butylidene, pentylidene, and hexylidene, which are $C_1$ to $C_6$ straight chain or branched chain alkylidene groups.

Examples of the cycloalkyl group include, for example, cyclopropyl, cyclobutyl, cyclopentyl, cyclohexyl, cycloheptyl, and cyclooctyl, which are $C_3$ to $C_8$ cycloalkyl groups. The aforementioned cycloalkyl group may be fused with benzene ring, naphthalene ring and the like, and examples include, for example, 1-indanyl, 2-indanyl, 1,2,3,4-tetrahydronaphthalen-1-yl, and 1,2,3,4-tetrahydronaphthalen-2-yl.

Examples of the cycloalkenyl group include, for example, 2-cyclopropen-1-yl, 2-cyclobuten-1-yl, 2-cyclopenten-1-yl, 3-cyclopenten-1-yl, 2-cyclohexen-1-yl, 3-cyclohexen-1-yl, 1-cyclobuten-1-yl, and 1-cyclopenten-1-yl, which are $C_3$ to $C_6$ cycloalkenyl groups. The aforementioned cycloalkenyl group may be fused with benzene ring, naphthalene ring and the like, and examples include, for example, 1-indanyl, 2-indanyl, 1,2,3,4-tetrahydronaphthalen-1-yl, 1,2,3,4-tetrahydronaphthalen-2-yl, 1-indenyl, and 2-indenyl.

Examples of the cycloalkanedienyl group include, for example, 2,4-cyclopentadien-1-yl, 2,4-cyclohexanedien-1-yl, and 2,5-cyclohexanedien-1-yl, which are $C_5$ to $C_6$ cycloalkanedienyl groups. The aforementioned cycloalkanedienyl group may be fused with benzene ring, naphthalene ring and the like, and examples include, for example, 1-indenyl and 2-indenyl.

Examples of the cycloalkyl-alkyl group include the groups in which one or more hydrogen atoms of the alkyl group are substituted with cycloalkyl group(s), and include, for example, cyclopropylmethyl, 1-cyclopropylethyl, 2-cyclopropylethyl, 3-cyclopropylpropyl, 4-cyclopropylbutyl, 5-cyclopropylpentyl, 6-cyclopropylhexyl, cyclobutylmethyl, cyclopentylmethyl, cyclobutylmethyl, cyclopentylmethyl, cyclohexylmethyl, cyclohexylpropyl, cyclohexylbutyl, cycloheptylmethyl, cyclooctylmethyl, and 6-cyclooctylhexyl, which are $C_4$ to $C_{14}$ cycloalkyl-alkyl groups.

Examples of the cycloalkylene group include, for example, cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, cycloheptane-1,1-diyl, cycloheptane-1,2-diyl, cyclooctane-1,1,-diyl, and cyclooctane-1,2-diyl, which are $C_3$ to $C_8$ cycloalkylene groups.

Examples of the cycloalkenylene group include, for example, 2-cyclopropene-1,1-diyl, 2-cyclobutene-1,1-diyl, 2-cyclopentene-1,1-diyl, 3-cyclopentene-1,1-diyl, 2-cyclohexene-1,1-diyl, 2-cyclohexene-1,2-diyl, 2-cyclohexene-1,4-diyl, 3-cyclohexene-1,1-diyl, 1-cyclobutene-1,2-diyl, 1-cyclopentene-1,2-diyl, and 1-cyclohexene-1,2-diyl, which are $C_3$ to $C_6$ cycloalkenylene groups.

Examples of the aryl group include a monocyclic or a fused polycyclic aromatic hydrocarbon group, and include, for example, phenyl, 1-naphtyl, 2-naphtyl, anthryl, phenanthryl, and acenaphthylenyl, which are $C_6$ to $C_{14}$ aryl groups. The aforementioned aryl group may be fused with the aforementioned $C_3$ to $C_8$ cycloalkyl group, $C_3$ to $C_6$ cycloalkenyl group, $C_5$ to $C_6$ cycloalkanedienyl group or the like, and examples include, for example, 4-indanyl, 5-indanyl, 1,2,3,4-tetrahydronaphthalen-5-yl, 1,2,3,4-tetrahydronaphthalen-6-yl, 3-acenaphthenyl, 4-acenaphthenyl, inden-4-yl, inden-5-yl, inden-6-yl, inden-7-yl, 4-phenalenyl, 5-phenalenyl, 6-phenalenyl, 7-phenalenyl, 8-phenalenyl, and 9-phenalenyl.

Examples of the arylene group include, for example, 1,2-phenylene, 1,3-phenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,4-diyl, naphthalene-2,5-diyl, naphthalene-2,6-diyl, naphthalene-2,7-diyl, naphthalene-2,8-diyl, and anthracene-1,4-diyl, which are $C_6$ to $C_{14}$ arylene groups.

Examples of the aralkyl group include the groups in which one or more hydrogen atoms of the alkyl group are substituted with aryl group(s), and include, for example, benzyl, 1-naphthylmethyl, 2-naphthylmethyl, anthracenylmethyl, phenanthrenylmethyl, acenaphthylenylmethyl, diphenylmethyl, 1-phenethyl, 2-phenethyl, 1-(1-naphthyl)ethyl, 1-(2-naphthyl)ethyl, 2-(1-naphthyl)ethyl, 2-(2-naphthyl)ethyl, 3-phenylpropyl, 3-(1-naphthyl)propyl, 3-(2-naphthyl)propyl, 4-phenylbutyl, 4-(1-naphthyl)butyl, 4-(2-naphthyl)butyl, 5-phenylpentyl, 5-(1-naphthyl)pentyl, 5-(2-naphthyl)pentyl, 6-phenylhexyl, 6-(1-naphthyl)hexyl, and 6-(2-naphthyl)hexyl, which are $C_7$ to $C_{16}$ aralkyl groups.

Examples of the bridged cyclic hydrocarbon group include, for example, bicyclo[2.1.0]pentyl, bicyclo[2.2.1]heptyl, bicyclo[2.2.1]octyl, and adamantyl.

Examples of the spiro cyclic hydrocarbon group include, for example, spiro[3.4]octyl, and spiro[4.5]deca-1,6-dienyl.

Examples of the terpene hydrocarbon include, for example, geranyl, neryl, linalyl, phytyl, menthyl, and bornyl.

Examples of the halogenated alkyl group include the groups in which one or more hydrogen atoms of the alkyl group are substituted with halogen atom(s), and include, for example, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, 2,2,2-trifluoroethyl, pentafluoroethyl, 3,3,3-trifluoropropyl, heptafluoropropyl, heptafluoroisopropyl, nonafluorobutyl, and perfluorohexyl, which are $C_1$ to $C_6$ straight chain or branched chain halogenated alkyl groups substituted with 1 to 13 halogen atoms.

Examples of the heterocyclic group include, for example, a monocyclic or a fused polycyclic hetero aryl group which comprises at least one hetero atom selected from oxygen atom, sulfur atom, nitrogen atom and the like as ring-constituting atoms (ring forming atoms), and a monocyclic or a fused polycyclic non-aromatic heterocyclic group which comprises at least one hetero atom selected from oxygen atom, sulfur atom, nitrogen atom and the like as ring-constituting atoms (ring forming atoms). When the heterocyclic group comprises two or more ring forming hetero atoms, each of them may be the same or different.

Examples of the monocyclic heteroaryl group include, for example, 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1-imidazolyl, 2-imidazolyl, 4-imidazolyl, 5-imidazolyl, 1-pyrazolyl, 3-pyrazolyl, 4-pyrazolyl, 5-pyrazolyl, (1,2,3-oxadiazol)-4-yl, (1,2,3-oxadiazol)-5-yl, (1,2,4-oxadiazol)-3-yl, (1,2,4-oxadiazol)-5-yl, (1,2,5-oxadiazol)-3-yl, (1,2,5-oxadiazol)-4-yl, (1,3,4-oxadiazol)-2-yl, (1,3,4-oxadiazol)-5-yl, furazanyl, (1,2,3-thiadiazol)-4-yl, (1,2,3-thiadiazol)-5-yl, (1,2,4-thiadiazol)-3-yl, (1,2,4-thiadiazol)-5-yl, (1,2,5-thiadiazol)-3-yl, (1,2,5-thiadiazol)-4-yl, (1,3,4-thiadiazolyl)-2-yl, (1,3,4-thiadiazolyl)-5-yl, (1H-1,2,3-triazol)-1-yl, (1H-1,2,3-triazol)-4-yl, (1H-1,2,3-triazol)-5-yl, (2H-1,2,3-triazol)-2-yl, (2H-1,2,3-triazol)-4-yl, (1H-1,2,4-triazol)-1-yl, (1H-1,2,4-triazol)-3-yl, (1H-1,2,4-triazol)-5-yl, (4H-1,2,4-triazol)-3-yl, (4H-1,2,4-triazol)-4-yl, (1H-tetrazol)-1-yl, (1H-tetrazol)-5-yl, (2H-tetrazol)-2-yl, (2H-tetrazol)-5-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, (1,2,3-triazin)-4-yl, (1,2,3-triazin)-5-yl, (1,2,4-triazin)-3-yl, (1,2,4-triazin)-5-yl, (1,2,4-triazin)-6-yl, (1,3,5-triazin)-2-yl, 1-azepinyl, 2-azepinyl, 3-azepinyl, 4-azepinyl, (1,4-oxazepin)-2-yl, (1,4-oxazepin)-3-yl, (1,4-oxazepin)-5-yl, (1,4-oxazepin)-6-yl, (1,4-oxazepin)-7-yl, (1,4-thiazepin)-2-yl, (1,4-thiazepin)-3-yl, (1,4-thiazepin)-5-yl, (1,4-thiazepin)-6-yl, and (1,4-thiazepin)-7-yl, which are 5 to 7-membered monocyclic heteroaryl groups.

Examples of the fused polycyclic heteroaryl group include, for example, 2-benzofuranyl, 3-benzofuranyl, 4-benzofuranyl, 5-benzofuranyl, 6-benzofuranyl, 7-benzofuranyl, 1-isobenzofuranyl, 4-isobenzofuranyl, 5-isobenzofuranyl, 2-benzo[b]thienyl, 3-benzo[b]thienyl, 4-benzo[b]thienyl, 5-benzo[b]thienyl, 6-benzo[b]thienyl, 7-benzo[b]thienyl, 1-benzo[c]thienyl, 4-benzo[c]thienyl, 5-benzo[c]thienyl, 1-indolyl, 1-indolyl, 2-indolyl, 3-indolyl, 4-indolyl, 5-indolyl, 6-indolyl, 7-indolyl, (2H-isoindol)-1-yl, (2H-isoindol)-2-yl, (2H-isoindol)-4-yl, (2H-isoindol)-5-yl, (1H-indazol)-1-yl, (1H-indazol)-3-yl, (1H-indazol)-4-yl, (1H-indazol)-5-yl, (1H-indazol)-6-yl, (1H-indazol)-7-yl, (2H-indazol)-1-yl, (2H-indazol)-2-yl, (2H-indazol)-4-yl, (2H-indazol)-5-yl, 2-benzoxazolyl, 2-benzoxazolyl, 4-benzoxazolyl, 5-benzoxazolyl, 6-benzoxazolyl, 7-benzoxazolyl, (1,2-benzisoxazol)-3-yl, (1,2-benzisoxazol)-4-yl, (1,2-benzisoxazol)-5-yl, (1,2-benzisoxazol)-6-yl, (1,2-benzisoxazol)-7-yl, (2,1-benzisoxazol)-3-yl, (2,1-benzisoxazol)-4-yl, (2,1-benzisoxazol)-5-yl, (2,1-benzisoxazol)-6-yl, (2,1-benzisoxazol)-7-yl, 2-benzothiazolyl, 4-benzothiazolyl, 5-benzothiazolyl, 6-benzothiazolyl, 7-benzothiazolyl, (1,2-benzisothiazol)-3-yl, (1,2-benzisothiazol)-4-yl, (1,2-benzisothiazol)-5-yl, (1,2-benzisothiazol)-6-yl, (1,2-benzisothiazol)-7-yl, (2,1-benzisothiazol)-3-yl, (2,1-benzisothiazol)-4-yl, (2,1-benzisothiazol)-5-yl, (2,1-benzisothiazol)-6-yl, (2,1-benzisothiazol)-7-yl, (1,2,3-benzoxadiazol)-4-yl, (1,2,3-benzoxadiazol)-5-yl, (1,2,3-benzoxadiazol)-6-yl, (1,2,3-benzoxadiazol)-7-yl, (2,1,3-benzoxadiazol)-4-yl, (2,1,3-benzoxadiazol)-5-yl, (1,2,3-benzothiadiazol)-4-yl, (1,2,3-benzothiadiazol)-5-yl, (1,2,3-benzothiadiazol)-6-yl, (1,2,3-benzothiadiazol)-7-yl, (2,1,3-benzothiadiazol)-4-yl, (2,1,3-benzothiadiazol)-5-yl, (1H-benzotriazol)-1-yl, (1H-benzotriazol)-4-yl, (1H-benzotriazol)-5-yl, (1H-benzotriazol)-6-yl, (1H-benzotriazol)-7-yl, (2H-benzotriazol)-2-yl, (2H-benzotriazol)-4-yl, (2H-benzotriazol)-5-yl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 3-cinnolinyl, 4-cinnolinyl, 5-cinnolinyl, 6-cinnolinyl, 7-cinnolinyl, 8-cinnolinyl, 2-quinazolinyl, 4-quinazolinyl, 5-quinazolinyl, 6-quinazolinyl, 7-quinazolinyl, 8-quinazolinyl, 2-quinoxalinyl, 5-quinoxalinyl, 6-quinoxalinyl, 1-phthalazinyl, 5-phthalazinyl, 6-phthalazinyl, 2-naphthyridinyl, 3-naphthyridinyl, 4-naphthyridinyl, 2-purinyl, 6-purinyl, 7-purinyl, 8-purinyl, 2-pteridinyl, 4-pteridinyl, 6-pteridinyl, 7-pteridinyl, 1-carbazolyl, 2-carbazolyl, 3-carbazolyl, 4-carbazolyl, 9-carbazolyl, 2-(α-carbolinyl), 3-(α-carbolinyl), 4-(α-carbolinyl), 5-(α-carbolinyl), 6-(α-carbolinyl), 7-(α-carbolinyl), 8-(α-carbolinyl), 9-(α-carbolinyl), 1-(β-carbolinyl), 3-(β-carbolinyl), 4-(β-carbolinyl), 5-(β-carbolinyl), 6-(β-carbolinyl), 7-(β-carbolinyl), 8-(β-carbolinyl), 9-(β-carbolinyl), 1-(γ-carbolinyl), 2-(γ-carbolinyl), 4-(γ-carbolinyl), 5-(γ-carbolinyl), 6-(γ-carbolinyl), 7-(γ-carbolinyl), 8-(γ-carbolinyl), 9-(γ-carbolinyl), 1-acridinyl, 2-acridinyl, 3-acridinyl, 4-acridinyl, 9-acridinyl, 1-phenoxazinyl, 2-phenoxazinyl, 3-phenoxazinyl, 4-phenoxazinyl, 10-phenoxazinyl, 1-phenothiazinyl, 2-phenothiazinyl, 3-phenothiazinyl, 4-phenothiazinyl, 10-phenothiazinyl, 1-phenazinyl, 2-phenazinyl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 2-phenanthrolinyl, 3-phenanthrolinyl, 4-phenanthrolinyl, 5-phenanthrolinyl, 6-phenanthrolinyl, 7-phenanthrolinyl, 8-phenanthrolinyl, 9-phenanthrolinyl, 10-phenanthrolinyl, 1-thianthrenyl, 2-thianthrenyl, 1-indolizinyl, 2-indolizinyl, 3-indolizinyl, 5-indolizinyl, 6-indolizinyl, 7-indolizinyl, 8-indolizinyl, 1-phenoxathiinyl, 2-phenoxathiinyl, 3-phenoxathiinyl, 4-phenoxathiinyl, thieno[2,3,-b]furyl, pyrrolo[1,2-b]pyridazinyl, pyrazolo[1,5-a]pyridyl, imidazo[11,2-a]pyridyl, imidazo[1,5-a]pyridyl, imidazo[1,2-b]pyridazinyl, imidazo[1,2-a]pyrimidinyl, 1,2, 4-triazolo[4,3-a]pyridyl, and 1,2,4-triazolo[4,3-a]pyridazinyl, which are 8 to 14-membered fused polycyclic heteroaryl groups.

Examples of the monocyclic non-aromatic heterocyclic group include, for example, 1-aziridinyl, 1-azetidinyl, 1-pyrrolidinyl, 2-pyrrolidinyl, 3-pyrrolidinyl, 2-tetrahydrofuryl, 3-tetrahydrofuryl, thiolanyl, 1-imidazolidinyl, 2-imidazolidinyl, 4-imidazolidinyl, 1-pyrazolidinyl, 3-pyrazolidinyl, 4-pyrazolidinyl, 1-(2-pyrrolinyl), 1-(2-imidazolinyl), 2-(2-imidazolinyl), 1-(2-pyrazolinyl), 3-(2-pyrazolinyl), piperidino, 2-piperidinyl, 3-piperidinyl, 4-piperidinyl, 1-homopiperidinyl, 2-tetrahydropyranyl, morpholino, (thiomorpholin)-4-yl, 1-piperazinyl, and 1-homopiperazinyl, which are 3 to 7-membered saturated or unsaturated monocyclic non-aromatic heterocyclic groups.

Examples of the fused polycyclic non-aromatic heterocyclic group include, for example, 2-quinuclidinyl, 2-chromanyl, 3-chromanyl, 4-chromanyl, 5-chromanyl, 6-chromanyl, 7-chromanyl, 8-chromanyl, 1-isochromanyl, 3-isochromanyl, 4-isochromanyl, 5-isochromanyl, 6-isochromanyl, 7-isochromanyl, 8-isochromanyl, 2-thiochromanyl, 3-thiochromanyl, 4-thiochromanyl, 5-thiochromanyl, 6-thiochromanyl, 7-thiochromanyl, 8-thiochromanyl, 1-isothiochromanyl, 3-isothiochromanyl, 4-isothiochromanyl, 5-isothiochromanyl, 6-isothiochromanyl, 7-isothiochromanyl, 8-isothiochromanyl, 1-indolinyl, 2-indolinyl, 3-indolinyl, 4-indolinyl, 5-indolinyl, 6-indolinyl, 7-indolinyl, 1-isoindolinyl, 2-isoindolinyl, 4-isoindolinyl, 5-isoindolinyl, 2-(4H-chromenyl), 3-(4H-chromenyl), 4-(4H-chromenyl), 5-(4H-chromenyl), 6-(4H-chromenyl), 7-(4H-chromenyl), 8-(4H-chromenyl), 1-isochromenyl, 3-isochromenyl, 4-isochromenyl, 5-isochromenyl, 6-isochromenyl, 7-isochromenyl, 8-isochromenyl, 1-(1H-pyrrolidinyl), 2-(1H-pyrrolidinyl), 3-(1H-pyrrolidinyl), 5-(1H-pyrrolidinyl), 6-(1H-pyrrolidinyl), and 7-(1H-pyrrolidinyl), which are 8 to 10-membered saturated or unsaturated fused polycyclic non-aromatic heterocyclic groups.

In the present specification, among the aforementioned heterocyclic groups, a monocyclic or a fused polycyclic heteroaryl groups which may have one or more hetero atoms selected from oxygen atom, sulfur atom, nitrogen atom and the like as ring-constituting atoms (ring forming atoms) in addition to the nitrogen atom that has the bond, and a monocyclic or a fused polycyclic non-aromatic heterocyclic groups which may have one or more hetero atoms selected from oxygen atom, sulfur atom, nitrogen atom and the like as ring-constituting atoms (ring forming atoms) in addition to the nitrogen atom that has the bond, are referred to as "cyclic amino group." When the cyclic amino group has two or more hetero atoms as ring-constituting atoms, each of them may be the same or different. Examples include, for example, 1-pyrrolidinyl, 1-imidazolidinyl, 1-pyrazolidinyl, 1-oxazolidinyl, 1-thiazolidinyl, piperidino, morpholino, 1-piperazinyl, thiomorpholin-4-yl, 1-homopiperidinyl, 1-homopiperazinyl, 2-pyrolin-1-yl, 2-imidazolin-1-yl, 2-pyrazolin-1-yl, 1-indolinyl, 2-isoindolinyl, 1,2,3,4-tetrahydroquinolin-1-yl, 1,2,3,4-tetrahydroisoquinolin-2-yl, 1-pyrrolyl, 1-imidazolyl, 1-pyrazolyl, 1-indolyl, 1-indazolyl, and 2-isoindolyl.

In the present specification, the aforementioned cycloalkyl group, cycloalkenyl group, cycloalkanedienyl group, aryl group, and heterocyclic group are generically referred to as "cyclic group." Furthermore, among said cyclic groups, particularly, aryl group, monocyclic heteroaryl group, and fused polycyclic heteroaryl group are generically referred to as "aromatic ring group."

Examples of the hydrocarbon-oxy group include the groups in which a hydrogen atom of the hydroxy group is substituted with a hydrocarbon group, and examples of the hydrocarbon include similar groups to the aforementioned hydrocarbon groups. Examples of the hydrocarbon-oxy group include, for example, alkoxy group (alkyl-oxy group), alkenyl-oxy group, alkynyl-oxy group, cycloalkyl-oxy group, cycloalkyl-alkyl-oxy group and the like, which are aliphatic hydrocarbon-oxy groups; aryl-oxy group; aralkyl-oxy group; and alkylene-dioxy group.

Examples of the alkoxy (alkyl-oxy group) include, for example, methoxy, ethoxy, n-propoxy, isopropoxy, n-butoxy, isobutoxy, sec-butoxy, tert-butoxy, n-pentyloxy, isopentyloxy, 2-methylbutoxy, 1-methylbutoxy, neopentyloxy, 1,2-dimethylpropoxy, 1-ethylpropoxy, n-hexyloxy, 4-methylpentyloxy, 3-methylpentyloxy, 2-methylpentyloxy, 1-methylpentyloxy, 3,3-dimethylbutoxy, 2,2-dimethybutoxy, 1,1-dimethylbutoxy, 1,2-dimethylbutoxy, 1,3-dimethylbutoxy, 2,3-dimethylbutoxy, 2-ethylbutoxy, 1-ethylbutoxy, 1-ethyl-1-methylpropoxy, n-heptyloxy, n-octyloxy, n-nonyloxy, n-decyloxy, n-undecyloxy, n-dodecyloxy, n-tridecyloxy, n-tetradecyloxy, and n-pentadecyloxy, which are $C_1$ to $C_{15}$ straight chain or branched chain alkoxy groups.

Examples of the alkenyl-oxy group include, for example, vinyloxy, (prop-1-en-1-yl)oxy, allyloxy, isopropenyloxy, (but-1-en-1-yl)oxy, (but-2-en-1-yl)oxy, (but-3-en-1-yl)oxy, (2-methylprop-2-en-1-yl)oxy, (1-methylprop-2-en-1-yl)oxy, (pent-1-en-1-yl)oxy, (pent-2-en-1-yl)oxy, (pent-3-en-1-yl)oxy, (pent-4-en-1-yl)oxy, (3-methylbut-2-en-1-yl)oxy, (3-methylbut-3-en-1-yl)oxy, (hex-1-en-1-yl)oxy, (hex-2-en-1-yl)oxy, (hex-3-en-1-yl)oxy, (hex-4-en-1-yl)oxy, (hex-5-en-1-yl)oxy, (4-methylpent-3-en-1-yl)oxy, (4-methylpent-3-en-1-yl)oxy, (hept-1-en-1-yl)oxy, (hept-6-en-1-yl)oxy, (oct-1-en-1-yl)oxy, (oct-7-en-1-yl)oxy, (non-1-en-1-yl)oxy, (non-8-en-1-yl)oxy, (dec-1-en-1-yl)oxy, (dec-9-en-1-yl)oxy, (undec-1-en-1-yl)oxy, (undec-10-en-1-yl)oxy, (dodec-1-en-1-yl)oxy, (dodec-11-en-1-yl)oxy, (tridec-1-en-1-yl)oxy, (tridec-12-en-1-yl)oxy, (tetradec-1-en-1-yl)oxy, (tetradec-13-en-1-yl)oxy, (pentadec-1-en-1-yl)oxy, and (pentadec-14-en-1-yl)oxy, which are $C_2$ to $C_{15}$ straight chain or branched chain alkenyl-oxy groups.

Examples of the alkynyl-oxy group include, for example, ethynyloxy, (prop-1-yn-1-yl)oxy, (prop-2-yn-1-yl)oxy, (but-1-yn-1-yl)oxy, (but-3-yn-1-yl)oxy, (1-methylprop-2-yn-1-yl)oxy, (pent-1-yn-1-yl)oxy, (pent-4-yn-1-yl)oxy, (hex-1-yn-1-yl)oxy, (hex-5-yn-1-yl)oxy, (hept-1-yn-1-yl)oxy, (hept-6-yn-1-yl)oxy, (oct-1-yn-1-yl)oxy, (oct-7-yn-1-yl)oxy, (non-1-yn-1-yl)oxy, (non-8-yn-1-yl)oxy, (dec-1-yn-1-yl)oxy, (dec-9-yn-1-yl)oxy, (undec-1-yn-1-yl)oxy, (undec-10-yn-1-yl)oxy, (dodec-1-yn-1-yl)oxy, (dodec-11-yn-1-yl)oxy, (tridec-1-yn-1-yl)oxy, (tridec-12-yn-1-yl)oxy, (tetradec-1-yn-1-yl)oxy, (tetradec-13-yn-1-yl)oxy, (pentadec-1-yn-1-yl)oxy, and (pentadec-14-yn-1-yl)oxy, which are $C_2$ to $C_{15}$ straight chain or branched chain alkynyl-oxy groups.

Examples of the cycloalkyl-oxy group include, for example, cyclopropoxy, cyclobutoxy, cyclopentyloxy, cyclohexyloxy, cycloheptyloxy, and cyclooctyloxy, which are $C_3$ to $C_8$ cycloalkyl-oxy groups.

Examples of the cycloalkyl-alkyl-oxy group include, for example, cyclopropylmethoxy, 1-cyclopropylethoxy, 2-cyclopropylethoxy, 3-cyclopropylpropoxy, 4-cyclopropylbutoxy, 5-cyclopropylpentyloxy, 6-cyclopropylhexyloxy, cyclobutylmethoxy, cyclopentylmethoxy, cyclobutylmethoxy, cyclopentylmethoxy, cyclohexylmethoxy, 2-cyclohexylethoxy, 3-cyclohexylpropoxy, 4-cyclohexylbutoxy, cycloheptylmethoxy, cyclooctylmethoxy, and 6-cyclooctylhexyloxy, which are $C_4$ to $C_{14}$ cycloalkyl-alkyl-oxy groups.

Examples of the aryl-oxy group include, for example, phenoxy, 1-naphthyloxy, 2-naphthyloxy, anthryloxy, phenanthryloxy, and acenaphthylenyloxy, which are $C_6$ to $C_{14}$ aryl-oxy groups.

Examples of the aralkyl-oxy group include, for example, benzyloxy, 1-naphthylmethoxy, 2-naphthylmethoxy, anthracenylmethoxy, phenanthrenylmethoxy, acenaphthylenylmethoxy, diphenylmethoxy, 1-phenethyloxy, 2-phenethyloxy, 1-(1-naphthyl)ethoxy, 1-(2-naphthyl)ethoxy, 2-(1-naphthyl)ethoxy, 2-(2-naphthyl)ethoxy, 3-phenylpropoxy, 3-(1-naphthyl)propoxy, 3-(2-naphthyl)propoxy, 4-phenylbutoxy, 4-(1-naphthyl)butoxy, 4-(2-naphthyl)butoxy, 5-phenylpentyloxy, 5-(1-naphthyl)pentyloxy, 5-(2-naphthyl)pentyloxy, 6-phenylhexyloxy, 6-(1-naphthyl)hexyloxy, and 6-(2-naphthyl)hexyloxy, which are $C_7$ to $C_{16}$ aralkyl-oxy groups.

Examples of the alkylenedioxy group include, for example, methylenedioxy, ethylenedioxy, 1-methylmethylenedioxy, and 1,1-dimethylmethylenedioxy.

Examples of the halogenated alkoxy group (halogenated alkyl-oxy group) include the groups in which a hydrogen atom of the hydroxy group is substituted with a halogenated alkyl group, and include, for example, fluoromethoxy, difluoromethoxy, chloromethoxy, bromomethoxy, iodomethoxy, trifluoromethoxy, trichloromethoxy, 2,2,2-trifluoroethoxy, pentafluoroethoxy, 3,3,3-trifluoropropoxy, heptafluoropropoxy, heptafluoroisopropoxy, nonafluorobutoxy, and perfluorohexyloxy, which are $C_1$ to $C_6$ straight chain or branched chain halogenated alkoxy groups substituted with 1 to 13 halogen atoms.

Examples of the heterocyclic-oxy group include the groups in which a hydrogen atom of the hydroxy group is substituted with a heterocyclic group, and examples of the heterocyclic ring include similar groups to the aforementioned heterocyclic groups. Examples of the heterocyclic-oxy group include, for example, a monocyclic heteroaryl-oxy group, a fused polycyclic heteroaryl-oxy group, a monocyclic non-aromatic heterocyclic-oxy group, and a fused polycyclic non-aromatic heterocyclic-oxy group.

Examples of the monocyclic heteroaryl-oxy group include, for example, 3-thienyloxy, (isoxazol-3-yl)oxy, (thiazol-4-yl)oxy, 2-pyridyloxy, 3-pyridyloxy, 4-pyridyloxy, and (pyrimidin-4-yl)oxy.

Examples of the fused polycyclic heteroaryl-oxy group include, for example, 5-indolyloxy, (benzimidazol-2-yl)oxy, 2-quinolyloxy, 3-quinolyloxy, and 4-quinolyloxy.

Examples of the monocyclic non-aromatic heterocyclic-oxy group include, for example, 3-pyrrolidinyloxy, and 4-piperidinyloxy.

Examples of the fused polycyclic non-aromatic heterocyclic-oxy group include, for example, 3-indolynyloxy, and 4-chromanyloxy.

Examples of the hydrocarbon-sulfanyl group include the groups in which a hydrogen atom of the sulfanyl group is substituted with a hydrocarbon group, and examples of the hydrocarbon include similar groups to the aforementioned hydrocarbon groups. Examples of the hydrocarbon-sulfanyl groups include, for example, alkyl-sulfanyl group, alkenyl-sulfanyl group, alkynyl-sulfanyl group, cycloalkyl-sulfanyl group, cycloalkyl-alkyl-sulfanyl group and the like, which are aliphatic hydrocarbon-sulfanyl groups; aryl-sulfanyl group, and aralkyl-sulfanyl group.

Examples of the alkyl-sulfanyl group include, for example, methylsulfanyl, ethylsulfanyl, n-propylsulfanyl, isopropylsulfanyl, n-butylsulfanyl, isobutylsulfanyl, sec-butylsulfanyl, tert-butylsulfanyl, n-pentylsulfanyl, isopentylsulfanyl, (2-methylbutyl)sulfanyl, (1-methylbutyl)sulfanyl, neopentylsulfanyl, (1,2-dimethylpropyl)sulfanyl, (1-ethylpropyl) sulfanyl, n-hexylsulfanyl, (4-methylpentyl)sulfanyl, (3-methylpentyl)sulfanyl, (2-methylpentyl)sulfanyl, (1-methylpentyl)sulfanyl, (3,3-dimethylbutyl)sulfanyl, (2,2-dimethylbutyl)sulfanyl, (1,1-dimethylbutyl)sulfanyl, (1,2-dimethylbutyl)sulfanyl, (1,3-dimethylbutyl)sulfanyl, (2,3-dimethylbutyl)sulfanyl, (2-ethylbutyl)sulfanyl, (1-ethylbutyl)sulfanyl, (1-ethyl-1-methylpropyl)sulfanyl, n-heptylsulfanyl, n-octylsulfanyl, n-nonylsulfanyl, n-decylsulfanyl, n-undecylsulfanyl, n-dodecylsulfanyl, n-tridecylsulfanyl, n-tetradecylsulfanyl, and n-pentadecylsulfanyl, which are $C_1$ to $C_{15}$ straight chain or branched chain alkyl-sulfanyl groups.

Examples of the alkenyl-sulfanyl group include, for example, vinylsulfanyl, (prop-1-en-1-yl)sulfanyl, allylsulfanyl, isopropenylsulfanyl, (but-1-en-1-yl)sulfanyl, (but-2-en-1-yl)sulfanyl, (but-3-en-1-yl)sulfanyl, (2-methylprop-2-en-1-yl)sulfanyl, (1-methylprop-2-en-1-yl)sulfanyl, (pent-1-en-1-yl)sulfanyl, (pent-2-en-1-yl)sulfanyl, (pent-3-en-1-yl)sulfanyl, (pent-4-en-1-yl)sulfanyl, (3-methylbut-2-en-1-yl)sulfanyl, (3-methylbut-3-en-1-yl)sulfanyl, (hex-1-en-1-yl)sulfanyl, (hex-2-en-1-yl)sulfanyl, (hex-3-en-1-yl)sulfanyl, (hex-4-en-1-yl)sulfanyl, (hex-5-en-1-yl)sulfanyl, (4-methylpent-3-en-1-yl)sulfanyl, (4-methylpent-3-en-1-yl)sulfanyl, (hept-1-en-1-yl)sulfanyl, (hept-6-en-1-yl)sulfanyl, (oct-1-en-1-yl)sulfanyl, (oct-7-en-1-yl)sulfanyl, (non-1-en-1-yl)sulfanyl, (non-8-en-1-yl)sulfanyl, (dec-1-en-1-yl)sulfanyl, (dec-9-en-1-yl)sulfanyl, (undec-1-en-1-yl)sulfanyl, (undec-10-en-1-yl)sulfanyl, (dodec-1-en-1-yl)sulfanyl, (dodec-11-en-1-yl)sulfanyl, (tridec-1-en-1-yl)sulfanyl, (tridec-12-en-1-yl)sulfanyl, (tetradec-1-en-1-yl)sulfanyl, (tetradec-13-en-1-yl)sulfanyl, (pentadec-1-en-1-yl)sulfanyl, and (pentadec-14-en-1-yl)sulfanyl, which are $C_2$ to $C_{15}$ straight chain or branched chain alkenyl-sulfanyl groups.

Examples of the alkynyl-sulfanyl group include, for example, ethynylsulfanyl, (prop-1-yn-1-yl)sulfanyl, (prop-2-yn-1-yl)sulfanyl, (but-1-yn-1-yl)sulfanyl, (but-3-yn-1-yl)sulfanyl, (1-methylprop-2-yn-1-yl)sulfanyl, (pent-1-yn-1-yl)sulfanyl, (pent-4-yn-1-yl)sulfanyl, (hex-1-yn-1-yl)sulfanyl, (hex-5-yn-1-yl)sulfanyl, (hept-1-yn-1-yl)sulfanyl, (hept-6-yn-1-yl)sulfanyl, (oct-1-yn-1-yl)sulfanyl, (oct-7-yn-1-yl)sulfanyl, (non-1-yn-1-yl)sulfanyl, (non-8-yn-1-yl)sulfanyl, (dec-1-yn-1-yl)sulfanyl, (dec-9-yn-1-yl)sulfanyl, (undec-1-yn-1-yl)sulfanyl, (undec-10-yn-1-yl)sulfanyl, (dodec-1-yn-1-yl)sulfanyl, (dodec-11-yn-1-yl)sulfanyl, (tridec-1-yn-1-yl)sulfanyl, (tridec-12-yn-1-yl)sulfanyl, (tetradec-1-yn-1-yl)sulfanyl, (tetradec-13-yn-1-yl)sulfanyl, (pentadec-1-yn-1-yl)sulfanyl, and (pentadec-14-yn-1-yl)sulfanyl, which are $C_2$ to $C_{15}$ straight chain or branched chain alkynyl-sulfanyl groups.

Examples of the cycloalkyl-sulfanyl group include, for example, cyclopropylsulfanyl, cyclobutylsulfanyl, cyclopentylsulfanyl, cyclohexylsulfanyl, cycloheptylsulfanyl, and cyclooctylsulfanyl, which are $C_3$ to $C_8$ cycloalkyl-sulfanyl groups.

Examples of the cycloalkyl-alkyl-sulfanyl group include, for example, (cyclopropylmethyl)sulfanyl, (1-cyclopropylethyl)sulfanyl, (2-cyclopropylethyl)sulfanyl, (3-cyclopropylpropyl)sulfanyl, (4-cyclopropylbutyl)sulfanyl, (5-cyclopropylpentyl)sulfanyl, (6-cyclopropylhexyl)sulfanyl, (cyclobutylmethyl)sulfanyl, (cyclopentylmethyl)sulfanyl, (cyclobutylmethyl)sulfanyl, (cyclopentylmethyl)sulfanyl, (cyclohexylmethyl)sulfanyl, (2-cyclohexylethyl)sulfanyl, (3-cyclohexylpropyl)sulfanyl, (4-cyclohexylbutyl)sulfanyl, (cycloheptylmethyl)sulfanyl, (cyclooctylmethyl)sulfanyl, and (6-cyclooctylhexyl)sulfanyl, which are $C_4$ to $C_{14}$ cycloalkyl-alkyl groups.

Examples of the aryl-sulfanyl group include, for example, phenylsulfanyl, 1-naphthylsulfanyl, 2-naphthylsulfanyl, anthrylsulfanyl, fenanthrylsulfanyl, and acenaphthylenylsulfanyl, which are $C_6$ to $C_{14}$ aryl-sulfanyl groups.

Examples of the aralkyl-sulfanyl group include, for example, benzylsulfanyl, (1-naphthylmethyl)sulfanyl, (2-naphthylmethyl)sulfanyl, (anthracenylmethyl)sulfanyl, (phenanthrenylmethyl)sulfanyl, (acenaphthylenylmethyl) sulfanyl, (diphenylmethyl)sulfanyl, (1-phenethyl)sulfanyl, (2-phenethyl)sulfanyl, (1-(1-naphthyl)ethyl)sulfanyl, (1-(2-naphthyl)ethyl)sulfanyl, (2-(1-naphthyl)ethyl)sulfanyl, (2-(2-naphthyl)ethyl)sulfanyl, (3-phenylpropyl)sulfanyl, (3-(1-naphthyl)propyl)sulfanyl, (3-(2-naphthyl)propyl)sulfanyl, (4-phenylbutyl)sulfanyl, (4-(1-naphthyl)butyl)sulfanyl, (4-(2-naphthyl)butyl)sulfanyl, (5-phenylpentyl)sulfanyl, (5-(1-naphthyl)pentyl)sulfanyl, (5-(2-naphthyl)pentyl)sulfanyl, (6-phenylhexyl)sulfanyl, (6-(1-naphthyl)hexyl)sulfanyl, and (6-(2-naphthyl)hexyl)sulfanyl, which are $C_7$ to $C_{16}$ aralkyl-sulfanyl groups.

Examples of the halogenated alkyl-sulfanyl group include the groups in which a hydrogen atom of the sulfanyl group is substituted with a halogenated alkyl group, and include, for example, (fluoromethyl)sulfanyl, (chloromethyl)sulfanyl, (bromomethyl)sulfanyl, (iodomethyl)sulfanyl, (difluoromethyl)sulfanyl, (trifluoromethyl)sulfanyl, (trichloromethyl)sulfanyl, (2,2,2-trifluoroethyl)sulfanyl, (pentafluoroethyl)sulfanyl, (3,3,3-trifluoropropyl)sulfanyl, (heptafluoropropyl)sulfanyl, (heptafluoroisopropyl)sulfanyl, (nonafluorobutyl)sulfanyl, and (perfluorohexyl)sulfanyl, which are $C_1$ to $C_6$ straight chain or branched chain halogenated alkyl-sulfanyl groups substituted with 1 to 13 halogen atoms.

Examples of the heterocyclic-sulfanyl group include the groups in which a hydrogen atom of the sulfanyl group is substituted with a heterocyclic group, and examples of the heterocyclic ring include similar groups to the aforementioned heterocyclic groups. Examples of the heterocyclic-sulfanyl group include, for example, a monocyclic heteroaryl-sulfanyl group, a fused polycyclic heteroaryl-sulfanyl group, a monocyclic non-aromatic heterocyclic-sulfanyl group, and a fused polycyclic non-aromatic heterocyclic-sulfanyl group.

Examples of the monocyclic heteroaryl-sulfanyl group include, for example, (imidazol-2-yl)sulfanyl, (1,2,4-triazol-2-yl)sulfanyl, (pyridin-2-yl)sulfanyl, (pyridin-4-yl)sulfanyl, and (pyrimidin-2-yl)sulfanyl.

Examples of the fused polycyclic heteroaryl-sulfanyl group include, for example, (benzimidazol-2-yl)sulfanyl, (quinolin-2-yl)sulfanyl, and (quinolin-4-yl)sulfanyl.

Examples of the monocyclic non-aromatic heterocyclic-sulfanyl groups include, for example, (3-pyrrolidinyl)sulfanyl, and (4-piperidinyl)sulfanyl.

Examples of the fused polycyclic non-aromatic heterocyclic-sulfanyl group include, for example, (3-indolinyl)sulfanyl, and (4-chromanyl)sulfanyl.

Examples of the acyl group include, for example, formyl group, glyoxyloyl group, thioformyl group, and groups represented by the following formulas:

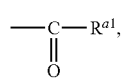 (ω-1A)

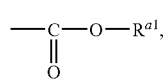 (ω-2A)

-continued

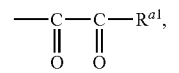 (ω-3A)

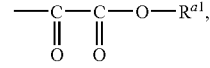 (ω-4A)

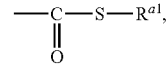 (ω-5A)

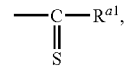 (ω-6A)

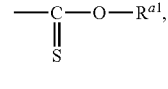 (ω-7A)

 (ω-8A)

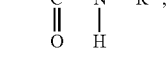 (ω-9A)

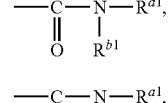 (ω-10A)

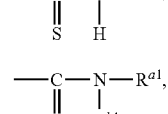 (ω-11A)

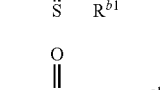 (ω-12A)

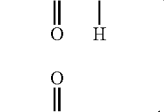 (ω-13A)

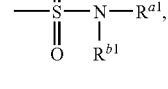 (ω-14A)

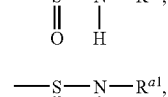 (ω-15A)

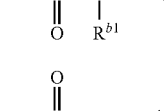 (ω-16A)

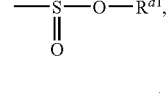 (ω-17A)

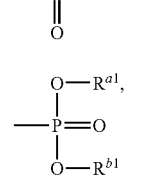 (ω-18A)

(ω-19A)

-continued

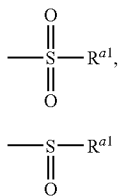

(ω-20A)

$$-S-R^{a1},$$

(ω-21A)

$$-S-R^{a1}$$
$$\parallel$$
$$O$$

wherein each of $R^{a1}$ and $R^{b1}$ independently represents a hydrocarbon group or a heterocyclic group, or when each of $R^{a1}$ and $R^{b1}$ binds to the same nitrogen atom, $R^{a1}$ and $R^{b1}$ may combine to each other, together with the nitrogen atom to which they bind, to form a cyclic amino group.

In the definition of the aforementioned acyl group, among the groups represented by the formula (ω-1A), those groups in which $R^{a1}$ is a hydrocarbon group are referred to as "hydrocarbon-carbonyl group" whose examples include, for example, acetyl, propionyl, butyryl, isobutyryl, valeryl, isovaleryl, pivaloyl, lauroyl, myristoryl, palmitoyl, acryloyl, propioloyl, methacryloyl, crotonoyl, isocrotonoyl, cyclohexylcarbonyl, cyclohexylmethylcarbonyl, benzoyl, 1-naphthoyl, 2-naphthoyl, and phenylacetyl, and those groups in which $R^{a1}$ is a heterocyclic group are referred to as "heterocyclic ring-carbonyl group" whose examples include, for example, 2-thenoyl, 3-furoyl, nicotinoyl, and isonicotinoyl.

Among the groups represented by the formula (ω-2A), those groups in which $R^{a1}$ is a hydrocarbon group are referred to as "hydrocarbon-oxy-carbonyl group" whose examples include, for example, methoxycarbonyl, ethoxycarbonyl, phenoxycarbonyl, and benzyloxycarbonyl, and those groups in which $R^{a1}$ is a heterocyclic group are referred to as "heterocyclic ring-oxy-carbonyl group" whose examples include, for example, 3-pyridyloxycarbonyl.

Among the groups represented by the formula (ω-3A), those groups in which $R^{a1}$ is a hydrocarbon group are referred to as "hydrocarbon-carbonyl-carbonyl group" whose examples include, for example, pyruvoyl, and those groups in which $R^{a1}$ is a heterocyclic group are referred to as "heterocyclic ring-carbonyl-carbonyl group."

Among the groups represented by the formula (ω-4A), those groups in which $R^{a1}$ is a hydrocarbon group are referred to as "hydrocarbon-oxy-carbonyl-carbonyl group" whose examples include, for example, methoxalyl and ethoxalyl groups, and those groups in which $R^{a1}$ is a heterocyclic group are referred to as "heterocyclic ring-oxy-carbonyl-carbonyl group."

Among the groups represented by the formula (ω-5A), those groups in which $R^{a1}$ is a hydrocarbon group are referred to as "hydrocarbon-sulfanyl-carbonyl group," and those groups in which $R^{a1}$ is a heterocyclic group are referred to as "heterocyclic ring-sulfanyl-carbonyl group."

Among the groups represented by the formula (ω-6A), those groups in which $R^{a1}$ is a hydrocarbon group are referred to as "hydrocarbon-thiocarbonyl group," and those groups in which $R^{a1}$ is a heterocyclic group are referred to as "heterocyclic ring-thiocarbonyl group."

Among the groups represented by the formula (ω-7A), those groups in which $R^{a1}$ is a hydrocarbon group are referred to as "hydrocarbon-oxy-thiocarbonyl group," and those groups in which $R^{a1}$ is a heterocyclic group are referred to as "heterocyclic ring-oxy-thiocarbonyl group."

Among the groups represented by the formula (ω-8A), those groups in which $R^{a1}$ is a hydrocarbon group are referred to as "hydrocarbon-sulfanyl-thiocarbonyl group," and those groups in which $R^{a1}$ is a heterocyclic group are referred to as "heterocyclic ring-sulfanyl-thiocarbonyl group."

Among the groups represented by the formula (ω-9A), those groups in which $R^{a1}$ is a hydrocarbon group are referred to as referred to as "N-hydrocarbon-carbamoyl group" whose examples include, for example, N-methylcarbamoyl group, and those groups in which $R^{a1}$ is a heterocyclic group are referred to as "N-heterocyclic ring-carbamoyl group."

Among the groups represented by the formula (ω-10A), those groups in which both $R^{a1}$ and $R^{b1}$ are hydrocarbon groups are referred to as "N,N-di(hydrocarbon)-carbamoyl group" whose examples include, for example, N,N-dimethylcarbamoyl group, those groups in which both $R^{a1}$ and $R^{b1}$ are heterocyclic groups are referred to as "N,N-di(heterocyclic ring)-carbamoyl group," those groups in which $R^{a1}$ is a hydrocarbon group and $R^{b1}$ is a heterocyclic group are referred to as "N-hydrocarbon-N-heterocyclic ring-substituted carbamoyl group," and those groups in which $R^{a1}$ and $R^{b1}$ combine to each other, together with the nitrogen atom to which they bind, to form a cyclic amino group are referred to as "cyclic amino-carbonyl group" whose examples include, for example, morpholino-carbonyl.

Among the groups represented by the formula (ω-11A), those groups in which $R^{a1}$ is a hydrocarbon group are referred to as "N-hydrocarbon-thiocarbamoyl group," and those groups in which $R^{a1}$ is a heterocyclic group are referred to as "N-heterocyclic ring-thiocarbamoyl group."

Among the groups represented by the formula (ω-12A), those groups in which both $R^{a1}$ and $R^{b1}$ are hydrocarbon groups are referred to as "N,N-di(hydrocarbon)-thiocarbamoyl group," those groups in which both $R^{a1}$ and $R^{b1}$ are heterocyclic groups are referred to as "N,N-di(heterocyclic ring)-thiocarbamoyl group," those groups in which $R^{a1}$ is a hydrocarbon group and $R^{b1}$ is a heterocyclic group are referred to as "N-hydrocarbon-N-heterocyclic ring-thiocarbamoyl group," and those groups in which $R^{a1}$ and $R^{b1}$ combine to each other, together with the nitrogen atom to which they bind, to form a cyclic amino group are referred to as "cyclic amino-thiocarbonyl group."

Among the groups represented by the formula (ω-13A), those groups in which $R^{a1}$ is a hydrocarbon group are referred to as "N-hydrocarbon-sulfamoyl group," and those groups in which $R^{a1}$ is a heterocyclic group are referred to as "N-heterocyclic ring-sulfamoyl group."

Among the groups represented by the formula (ω-14A), those groups in which both $R^{a1}$ and $R^{b1}$ are hydrocarbon groups are referred to as "N,N-di(hydrocarbon)-sulfamoyl group" whose examples include, for example, N,N-dimethylsulfamoyl group, those groups in which both $R^{a1}$ and $R^{b1}$ are heterocyclic groups are referred to as "N,N-di(heterocyclic ring)-sulfamoyl group," those groups in which $R^{a1}$ is a hydrocarbon group and $R^{b1}$ is a heterocyclic group are referred to as "N-hydrocarbon-N-heterocyclic ring-sulfamoyl group," and those groups in which $R^{a1}$ and $R^{b1}$ combine to each other, together with the nitrogen atom to which they bind, to form a cyclic amino group are referred to as "cyclic amino-sulfonyl group" whose examples include, for example 1-pyrrolylsulfonyl.

Among the groups represented by the formula (ω-15A), those groups in which $R^{a1}$ is a hydrocarbon group are referred to as "N-hydrocarbon-sulfinamoyl group," and those groups in which $R^{a1}$ is a heterocyclic group are referred to as "N-heterocyclic ring-sulfinamoyl group."

Among the groups represented by the formula (ω-16A), those groups in which both $R^{a1}$ and $R^{b1}$ are hydrocarbon groups are referred to as "N,N-di(hydrocarbon)-sulfinamoyl group," those groups in which both $R^{a1}$ and $R^{b1}$ are heterocyclic groups are referred to as "N,N-di(heterocyclic ring)-sulfinamoyl group," those groups in which $R^{a1}$ is a hydrocarbon group and $R^{b1}$ is a heterocyclic group are referred to as "N-hydrocarbon-N-heterocyclic ring-sulfinamoyl group," and those groups in which $R^{a1}$ and $R^{b1}$ combine to each other, together with the nitrogen atom to which they bind, to form a cyclic amino group are referred to as "cyclic amino-sulfinyl group."

Among the groups represented by the formula (ω-17A), those groups in which $R^{a1}$ is a hydrocarbon group are referred to as "hydrocarbon-oxy-sulfonyl group," and those groups in which $R^{a1}$ is a heterocyclic group are referred to as "heterocyclic ring-oxy-sulfonyl group."

Among the groups represented by the formula (ω-18A), those groups in which $R^{a1}$ is a hydrocarbon group are referred to as "hydrocarbon-oxy-sulfinyl group," and those groups in which $R^{a1}$ is a heterocyclic group are referred to as "heterocyclic ring-oxy-sulfinyl group."

Among the groups represented by the formula (ω-19A), those groups in which both $R^{a1}$ and $R^{b1}$ are hydrocarbon groups are referred to as "O,O'-di(hydrocarbon)-phosphono group," those groups in which both $R^{a1}$ and $R^{b1}$ are heterocyclic groups are referred to as "O,O'-di(heterocyclic ring)-phosphono group," and those groups in which $R^{a1}$ is a hydrocarbon group and $R^{b1}$ is a heterocyclic group are referred to as "O-hydrocarbon-O'-heterocyclic ring-phosphono group."

Among the groups represented by the formula (ω-20A), those groups in which $R^{a1}$ is a hydrocarbon group are referred to as "hydrocarbon-sulfonyl group" whose examples include, for example, methanesulfonyl and benzenesulfonyl, and those groups in which $R^{a1}$ is a heterocyclic group are referred to as "heterocyclic ring-sulfonyl group."

Among the groups represented by the formula (ω-21A), those groups in which $R^{a1}$ is a hydrocarbon group are referred to as "hydrocarbon-sulfinyl group" whose examples include, for example, methylsulfinyl and benzenesulfinyl, and those groups in which $R^{a1}$ is a heterocyclic group are referred to as "heterocyclic ring-sulfinyl group."

Examples of the hydrocarbon in the groups represented by the aforementioned formulas (ω-1A) through (ω-21A) include the similar groups to the aforementioned hydrocarbon group. Examples of the hydrocarbon-carbonyl group represented by the formula (ω-1A) include, for example, an alkyl-carbonyl group, an alkenyl-carbonyl group, an alkynyl-carbonyl group, a cycloalkyl-carbonyl group, a cycloalkenyl-carbonyl group, a cycloalkanedienyl-carbonyl group, a cycloalkyl-alkyl-carbonyl group, which are aliphatic hydrocarbon-carbonyl groups; an aryl-carbonyl group; an aralkyl-carbonyl group; a bridged cyclic hydrocarbon-carbonyl group; a spirocyclic hydrocarbon-carbonyl group; and a terpene family hydrocarbon-carbonyl group. In the following descriptions, groups represented by the formulas (ω-2A) through (ω-21A) are similar to those explained above.

Examples of the heterocyclic ring in the groups represented by the aforementioned formulas (ω-1A) through (ω-21A) include similar groups to the aforementioned heterocyclic group. Examples of the heterocyclic ring-carbonyl group represented by the formula (ω-1A) include, for example, a monocyclic heteroaryl-carbonyl group, a fused polycyclic heteroaryl-carbonyl group, a monocyclic non-aromatic heterocyclic ring-carbonyl group, and a fused polycyclic non-aromatic heterocyclic ring-carbonyl group. In the following descriptions, groups represented by the formulas (ω-2A) through (ω-21A) are similar to those explained above.

Examples of the cyclic amino in the groups represented by the aforementioned formulas (ω-10A) through (ω-16A) include similar groups to the aforementioned cyclic amino group.

In the present specification, when a certain functional group is defined as "which may be substituted," the definition means that the functional group may sometimes have one or more substituents at chemically substitutable positions, unless otherwise specifically mentioned. Kind of substituents, number of substituents, and the position of substituents existing in the functional groups are not particularly limited, and when two or more substituents exist, they may be the same or different. Examples of the substituent existing in the functional group include, for example, halogen atoms, oxo group, thioxo group, nitro group, nitroso group, cyano group, isocyano group, cyanato group, thiocyanato group, isocyanato group, isothiocyanato group, hydroxy group, sulfanyl group, carboxy group, sulfanylcarbonyl group, oxalo group, methooxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, hydrocarbon group, heterocyclic group, hydrocarbon-oxy group, heterocyclic ring-oxy group, hydrocarbon-sulfanyl group, heterocyclic ring-sulfanyl group, acyl group, amino group, hydrazino group, hydrazono group, diazenyl group, ureido group, thioureido group, guanidino group, carbamoimidoyl group (amidino group), azido group, imino group, hydroxyamino group, hydroxyimino group, aminooxy group, diazo group, semicarbazino group, semicarbazono group, allophanyl group, hydantoyl group, phosphano group, phosphoroso group, phospho group, boryl group, silyl group, stannyl group, selanyl group, oxido group and the like.

When two or more substituents exist according to the aforementioned definition of "which may be substituted," said two or more substituents may combine to each other, together with atom(s) to which they bind, to form a ring. One or more substituents may exist on said ring. The ring may be monocyclic or fused polycyclic, and aromatic or non-aromatic.

The above substituents according to the aforementioned definition of "which may be substituted" may further be substituted with the aforementioned substituents at the chemically substitutable positions on the substituent. Kind of substituents, number of substituents, and positions of substituents are not particularly limited, and when the substituents are substituted with two or more substituents, they may be the same or different. Examples of the substituent include, for example, a halogenated alkyl-carbonyl group whose examples include, for example, trifluoroacetyl, a halogenated alkyl-sulfonyl group whose examples include, for example, trifluoromethanesulfonyl, an acyl-oxy group, an acyl-sulfanyl group, an N-hydrocarbon-amino group, an N,N-di(hydrocarbon)-amino group, an N-heterocyclic ring-amino group, an N-hydrocarbon-N-heterocyclic ring-amino group, an acyl-amino group, and a di(acyl)-amino group. Moreover, one or more arbitrary substituents may further exist on the aforementioned substituent.

Examples of the acyl-oxy group include the groups in which hydrogen atom of hydroxy group is substituted with acyl group, and include, for example, formyloxy group, glyoxyloyloxy group, thioformyloxy group, and groups represented by the following formulas:

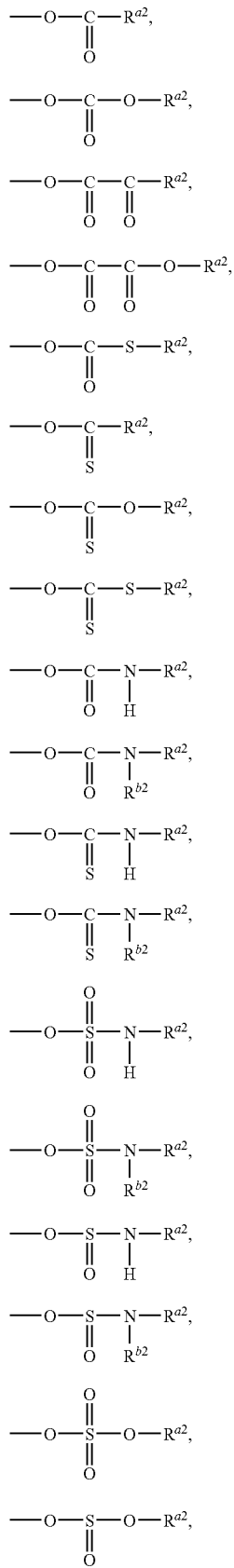
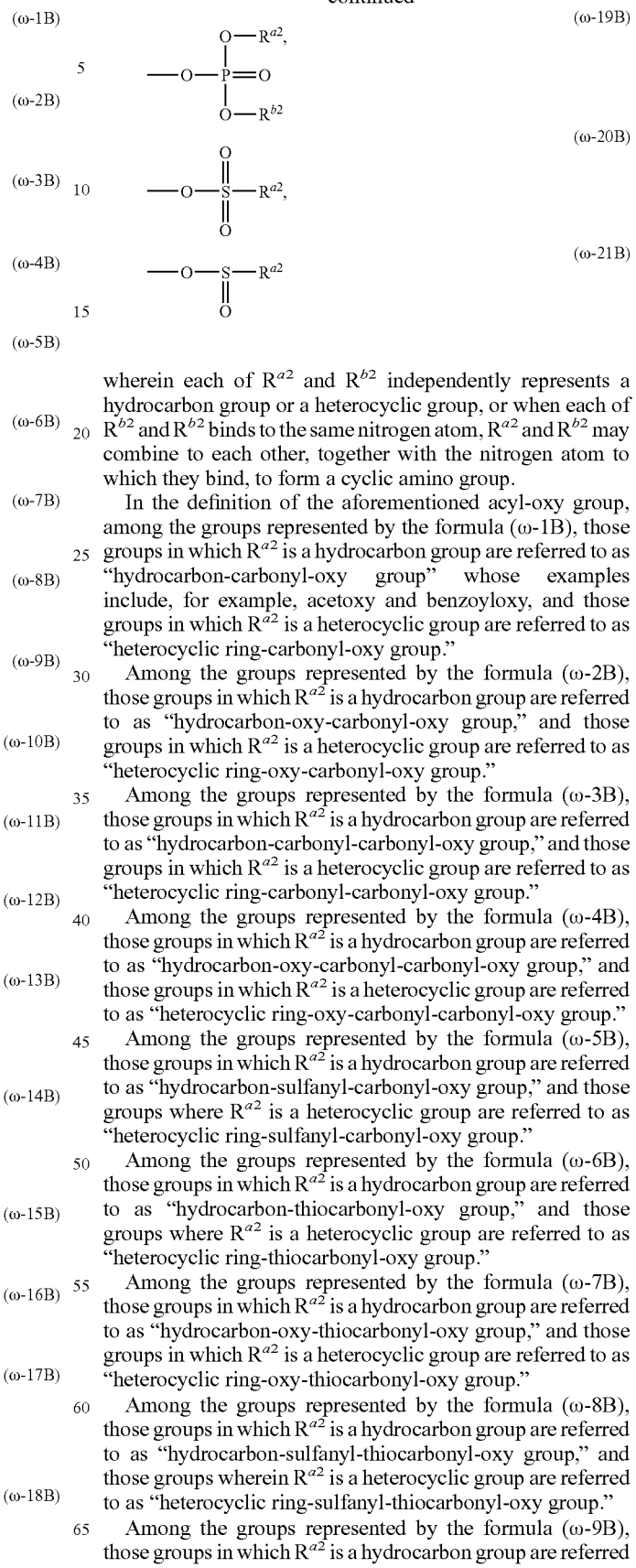

wherein each of $R^{a2}$ and $R^{b2}$ independently represents a hydrocarbon group or a heterocyclic group, or when each of $R^{b2}$ and $R^{b2}$ binds to the same nitrogen atom, $R^{a2}$ and $R^{b2}$ may combine to each other, together with the nitrogen atom to which they bind, to form a cyclic amino group.

In the definition of the aforementioned acyl-oxy group, among the groups represented by the formula (ω-1B), those groups in which $R^{a2}$ is a hydrocarbon group are referred to as "hydrocarbon-carbonyl-oxy group" whose examples include, for example, acetoxy and benzoyloxy, and those groups in which $R^{a2}$ is a heterocyclic group are referred to as "heterocyclic ring-carbonyl-oxy group."

Among the groups represented by the formula (ω-2B), those groups in which $R^{a2}$ is a hydrocarbon group are referred to as "hydrocarbon-oxy-carbonyl-oxy group," and those groups in which $R^{a2}$ is a heterocyclic group are referred to as "heterocyclic ring-oxy-carbonyl-oxy group."

Among the groups represented by the formula (ω-3B), those groups in which $R^{a2}$ is a hydrocarbon group are referred to as "hydrocarbon-carbonyl-carbonyl-oxy group," and those groups in which $R^{a2}$ is a heterocyclic group are referred to as "heterocyclic ring-carbonyl-carbonyl-oxy group."

Among the groups represented by the formula (ω-4B), those groups in which $R^{a2}$ is a hydrocarbon group are referred to as "hydrocarbon-oxy-carbonyl-carbonyl-oxy group," and those groups in which $R^{a2}$ is a heterocyclic group are referred to as "heterocyclic ring-oxy-carbonyl-carbonyl-oxy group."

Among the groups represented by the formula (ω-5B), those groups in which $R^{a2}$ is a hydrocarbon group are referred to as "hydrocarbon-sulfanyl-carbonyl-oxy group," and those groups where $R^{a2}$ is a heterocyclic group are referred to as "heterocyclic ring-sulfanyl-carbonyl-oxy group."

Among the groups represented by the formula (ω-6B), those groups in which $R^{a2}$ is a hydrocarbon group are referred to as "hydrocarbon-thiocarbonyl-oxy group," and those groups where $R^{a2}$ is a heterocyclic group are referred to as "heterocyclic ring-thiocarbonyl-oxy group."

Among the groups represented by the formula (ω-7B), those groups in which $R^{a2}$ is a hydrocarbon group are referred to as "hydrocarbon-oxy-thiocarbonyl-oxy group," and those groups in which $R^{a2}$ is a heterocyclic group are referred to as "heterocyclic ring-oxy-thiocarbonyl-oxy group."

Among the groups represented by the formula (ω-8B), those groups in which $R^{a2}$ is a hydrocarbon group are referred to as "hydrocarbon-sulfanyl-thiocarbonyl-oxy group," and those groups wherein $R^{a2}$ is a heterocyclic group are referred to as "heterocyclic ring-sulfanyl-thiocarbonyl-oxy group."

Among the groups represented by the formula (ω-9B), those groups in which $R^{a2}$ is a hydrocarbon group are referred to as "N-hydrocarbon-carbamoyl-oxy group," and those groups in which $R^{a2}$ is a heterocyclic group are referred to as "N-heterocyclic ring-carbamoyl-oxy group."

Among the groups represented by the formula (ω-10B), those groups in which both $R^{a2}$ and $R^{b2}$ are hydrocarbon groups are referred to as "N,N-di(hydrocarbon)-carbamoyl-oxy group," those groups in which both $R^{a2}$ and $R^{b2}$ are heterocyclic groups are referred to as "N,N-di(heterocyclic ring)-carbamoyl-oxy group," those groups in which $R^{a2}$ is a hydrocarbon group and $R^{b2}$ is a heterocyclic group are referred to as "N-hydrocarbon-N-heterocyclic ring-carbamoyl-oxy group," and those groups in which $R^{a2}$ and $R^{b2}$ combine to each other, together with the nitrogen atom to which they bind, to form a cyclic amino group are referred to as "cyclicamino-carbonyl-oxy group."

Among the groups represented by the formula (ω-11B), those groups in which $R^{a2}$ is a hydrocarbon group are referred to as "N-hydrocarbon-thiocarbamoyl-oxy group," and those groups in which $R^{a2}$ is a heterocyclic group are referred to as "N-heterocyclic ring-thiocarbamoyl-oxy group."

Among the groups represented by the formula (ω-12B), those groups in which both $R^{a2}$ and $R^{b2}$ are hydrocarbon groups are referred to as "N,N-di(hydrocarbon)-thiocarbamoyl-oxy group," those groups in which both $R^{a2}$ and $R^{b2}$ are heterocyclic groups are referred to as "N,N-di(heterocyclic ring)-thiocarbamoyl-oxy group," those groups in which $R^{a2}$ is a hydrocarbon group and $R^{b2}$ is a heterocyclic group are referred to as "N-hydrocarbon-N-heterocyclic ring-thiocarbamoyl-oxy group," and those groups in which $R^{a2}$ and $R^{b2}$ combine to each other, together with the nitrogen atom to which they bind, to form a cyclic amino group are referred to as "cyclicamino-thiocarbonyl-oxy group."

Among the groups represented by the formula (ω-13B), those groups in which $R^{a2}$ is a hydrocarbon group are referred to as "N-hydrocarbon-sulfamoyl-oxy group," and those groups in which $R^{a2}$ is a heterocyclic group are referred to as "N-heterocyclic ring-sulfamoyl-oxy group."

Among the groups represented by the formula (ω-14B), those groups in which both $R^{a2}$ and $R^{b2}$ are hydrocarbon groups are referred to as "N,N-di(hydrocarbon)-sulfamoyl-oxy group," those groups in which both $R^{a2}$ and $R^{b2}$ are heterocyclic groups are referred to as "N,N-di(heterocyclic ring)-sulfamoyl-oxy group," those groups in which $R^{a2}$ is a hydrocarbon group and $R^{b2}$ is a heterocyclic group are referred to as "N-hydrocarbon-N-heterocyclic ring-sulfamoyl-oxy group," and those groups in which $R^{a2}$ and $R^{b2}$ combine to each other, together with the nitrogen atom to which they bind, to form a cyclic amino group are referred to as "cyclic amino-sulfonyl-oxy group."

Among the groups represented by the formula (ω-15B), those groups in which $R^{a2}$ is a hydrocarbon group are referred to as "N-hydrocarbon-sulfinamoyl-oxy group," and those groups where $R^{a2}$ is a heterocyclic group are referred to as "N-heterocyclic ring-sulfinamoyl-oxy group."

Among the groups represented by the formula (ω-16B), those groups in which both $R^{a2}$ and $R^{b2}$ are hydrocarbon groups are referred to as "N,N-di(hydrocarbon)-sulfinamoyl-oxy group," those groups in which both $R^{a2}$ and $R^{b2}$ are heterocyclic groups are referred to as "N,N-di(heterocyclic ring)-sulfinamoyl-oxy group," those groups in which $R^{a2}$ is a hydrocarbon group and $R^{b2}$ is a heterocyclic group are referred to as "N-hydrocarbon-N-heterocyclic ring-sulfinamoyl-oxy group," and those groups in which $R^{a2}$ and $R^{b2}$ combine to each other, together with the nitrogen atom to which they bind, to form a cyclic amino group are referred to as "cyclic amino-sulfinyl-oxy group."

Among the groups represented by the formula (ω-17B), those groups in which $R^{a2}$ is a hydrocarbon group are referred to as "hydrocarbon-oxy-sulfonyl-oxy group," and those groups in which $R^{a2}$ is a heterocyclic group are referred to as "heterocyclic ring-oxy-sulfonyl-oxy group."

Among the groups represented by the formula (ω-18B), those groups in which $R^{a2}$ is a hydrocarbon group are referred to as "hydrocarbon-oxy-sulfinyl-oxy group," those groups in which $R^{a2}$ is a heterocyclic group are referred to as "heterocyclic ring-oxy-sulfinyl-oxy group."

Among the groups represented by the formula (ω-19B), those groups in which both $R^{a2}$ and $R^{b2}$ are hydrocarbon groups are referred to as "O,O'-di(hydrocarbon)-phosphono-oxy group," those groups in which both $R^{a2}$ and $R^{b2}$ are heterocyclic groups are referred to as "O,O'-di(heterocyclic ring)-phosphono-oxy group," and those groups in which $R^{a2}$ is a hydrocarbon group and $R^{b2}$ is a heterocyclic group are referred to as "O-hydrocarbon substituted-O'-heterocyclic ring substituted phosphono-oxy group."

Among the groups represented by the formula (ω-20B), those groups in which $R^{a2}$ is a hydrocarbon group are referred to as "hydrocarbon-sulfonyl-oxy group," and those groups in which $R^{a2}$ is a heterocyclic group referred to as "heterocyclic ring-sulfonyl-oxy group."

Among the groups represented by the formula (ω-21B), those groups in which $R^{a2}$ is a hydrocarbon group are referred to as "hydrocarbon-sulfinyl-oxy group," and those groups in which $R^{a2}$ is a heterocyclic group are referred to as "heterocyclic ring-sulfinyl-oxy group."

Examples of the hydrocarbon in the groups represented by the aforementioned formulas (ω-1B) through (ω-21B) include the similar groups to the aforementioned hydrocarbon group. Examples of the hydrocarbon-carbonyl-oxy group represented by the formula (ω-1B) include, for example, an alkyl-carbonyl-oxy group, an alkenyl-carbonyl-oxy group, an alkynyl-carbonyl-oxy group, a cycloalkyl-carbonyl-oxy group, a cycloalkenyl-carbonyl-oxy group, a cycloalkanedienyl-carbonyl-oxy group, and a cycloalkyl-alkyl-carbonyl-oxy group, which are aliphatic hydrocarbon-carbonyl-oxy groups; an aryl-carbonyl-oxy group; an aralkyl-carbonyl-oxy group; a bridged cyclic hydrocarbon-carbonyl-oxy group; a spirocyclic hydrocarbon-carbonyl-oxy group; and a terpene family hydrocarbon-carbonyl-oxy group. In the following descriptions, groups represented by the formulas (ω-2B) through (ω-21B) are similar to those explained above.

Examples of the heterocyclic ring in the groups represented by the aforementioned formulas (ω-1B) through (ω-21B) include similar groups to the aforementioned heterocyclic group. Examples of the heterocyclic ring-carbonyl group represented by the formula (ω-1B) include, for example, a monocyclic heteroaryl-carbonyl group, a fused polycyclic heteroaryl-carbonyl group, a monocyclic non-aromatic heterocyclic ring-carbonyl group, and a fused polycyclic non-aromatic heterocyclic ring-carbonyl group. In the following descriptions, groups represented by the formulas (ω-2B) through (ω-21B) are similar to those groups explained above.

Examples of the cyclic amino in the groups represented by the aforementioned formulas (ω-10B) through (ω-16B) include similar groups to the aforementioned cyclic amino group.

The aforementioned acyl-oxy group, hydrocarbon-oxy group, and heterocyclic-oxy group are generically referred to as "substituted oxy group." Moreover, these substituted oxy group and hydroxy group are generically referred to as "hydroxy group which may be substituted."

Examples of the acyl-sulfanyl group include the groups in which hydrogen atom of sulfanyl group is substituted with acyl group, and include, for example, formylsulfanyl group, glyoxyloylsulfanyl group, thioformylsulfanyl group, and groups represented by the following formulas:

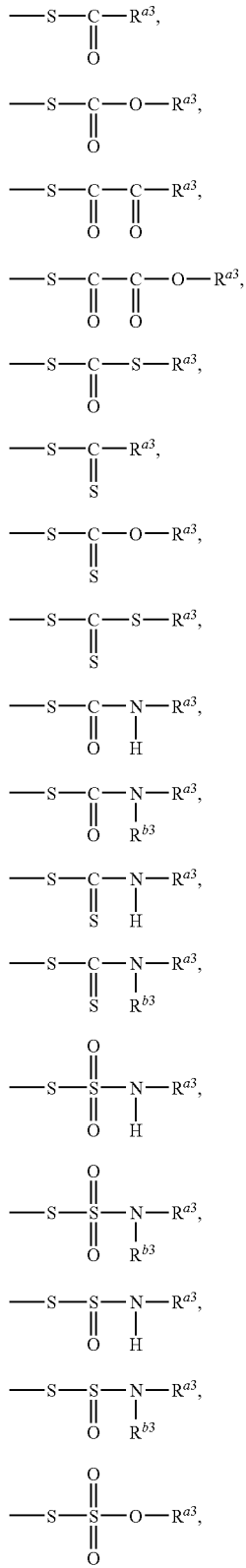

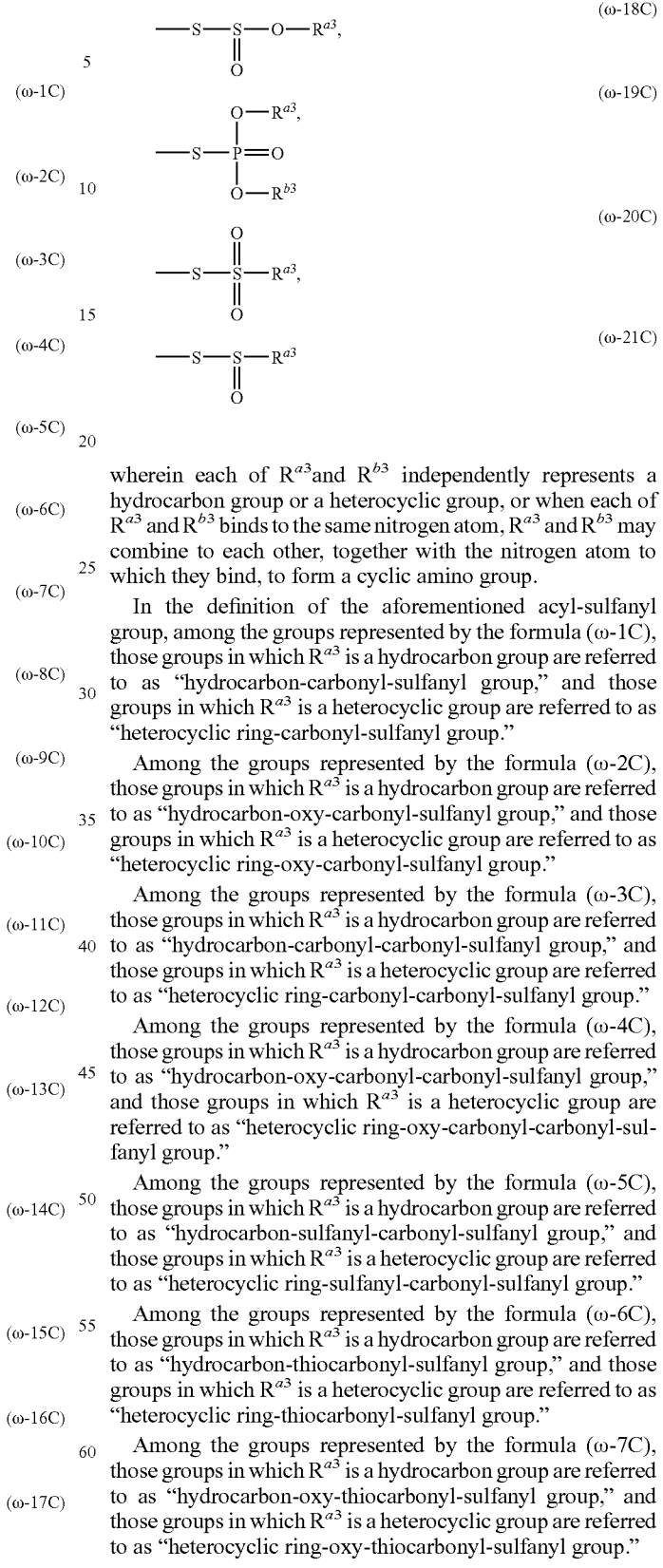

wherein each of $R^{a3}$ and $R^{b3}$ independently represents a hydrocarbon group or a heterocyclic group, or when each of $R^{a3}$ and $R^{b3}$ binds to the same nitrogen atom, $R^{a3}$ and $R^{b3}$ may combine to each other, together with the nitrogen atom to which they bind, to form a cyclic amino group.

In the definition of the aforementioned acyl-sulfanyl group, among the groups represented by the formula (ω-1C), those groups in which $R^{a3}$ is a hydrocarbon group are referred to as "hydrocarbon-carbonyl-sulfanyl group," and those groups in which $R^{a3}$ is a heterocyclic group are referred to as "heterocyclic ring-carbonyl-sulfanyl group."

Among the groups represented by the formula (ω-2C), those groups in which $R^{a3}$ is a hydrocarbon group are referred to as "hydrocarbon-oxy-carbonyl-sulfanyl group," and those groups in which $R^{a3}$ is a heterocyclic group are referred to as "heterocyclic ring-oxy-carbonyl-sulfanyl group."

Among the groups represented by the formula (ω-3C), those groups in which $R^{a3}$ is a hydrocarbon group are referred to as "hydrocarbon-carbonyl-carbonyl-sulfanyl group," and those groups in which $R^{a3}$ is a heterocyclic group are referred to as "heterocyclic ring-carbonyl-carbonyl-sulfanyl group."

Among the groups represented by the formula (ω-4C), those groups in which $R^{a3}$ is a hydrocarbon group are referred to as "hydrocarbon-oxy-carbonyl-carbonyl-sulfanyl group," and those groups in which $R^{a3}$ is a heterocyclic group are referred to as "heterocyclic ring-oxy-carbonyl-carbonyl-sulfanyl group."

Among the groups represented by the formula (ω-5C), those groups in which $R^{a3}$ is a hydrocarbon group are referred to as "hydrocarbon-sulfanyl-carbonyl-sulfanyl group," and those groups in which $R^{a3}$ is a heterocyclic group are referred to as "heterocyclic ring-sulfanyl-carbonyl-sulfanyl group."

Among the groups represented by the formula (ω-6C), those groups in which $R^{a3}$ is a hydrocarbon group are referred to as "hydrocarbon-thiocarbonyl-sulfanyl group," and those groups in which $R^{a3}$ is a heterocyclic group are referred to as "heterocyclic ring-thiocarbonyl-sulfanyl group."

Among the groups represented by the formula (ω-7C), those groups in which $R^{a3}$ is a hydrocarbon group are referred to as "hydrocarbon-oxy-thiocarbonyl-sulfanyl group," and those groups in which $R^{a3}$ is a heterocyclic group are referred to as "heterocyclic ring-oxy-thiocarbonyl-sulfanyl group."

Among the groups represented by the formula (ω-8C), those groups in which $R^{a3}$ is a hydrocarbon group are referred to as "hydrocarbon-sulfanyl-thiocarbonyl-sulfanyl group,"

and those groups in which $R^{a3}$ is a heterocyclic group are referred to as "heterocyclic ring-sulfanyl-thiocarbonyl-sulfanyl group."

Among the groups represented by the formula (ω-9C), those groups in which $R^{a3}$ is a hydrocarbon group are referred to as "N-hydrocarbon-carbamoyl-sulfanyl group," and those groups in which $R^{a3}$ is a heterocyclic group are referred to as "N-heterocyclic ring-carbamoyl-sulfanyl group."

Among the groups represented by the formula (ω-10C), those groups in which both $R^{a3}$ and $R^{b3}$ are a hydrocarbon groups are referred to as "N,N-di(hydrocarbon)-carbamoyl-sulfanyl group," those groups in which both $R^{a3}$ and $R^{b3}$ are heterocyclic groups are referred to as "N,N-di(heterocyclic ring)-carbamoyl-sulfanyl group," those groups in which $R^{a3}$ is a hydrocarbon group and $R^{b3}$ is a heterocyclic group are referred to as "N-hydrocarbon-N-heterocyclic ring-carbamoyl-sulfanyl group," and those groups in which $R^{a3}$ and $R^{b3}$ combine to each other, together with the nitrogen atom to which they bind, to form a cyclic amino group are referred to as "cyclicamino-carbonyl-sulfamoyl group."

Among the groups represented by the formula (ω-11C), those groups in which $R^{a3}$ is a hydrocarbon group are referred to as "N-hydrocarbon-thiocarbamoyl-sulfanyl group," and those groups in which $R^{a3}$ is a heterocyclic group are referred to as "N-heterocyclic ring-thiocarbamoyl-sulfanyl group."

Among the groups represented by the formula (ω-12C), those groups in which both $R^{a3}$ and $R^{b3}$ are hydrocarbon groups are referred to as "N,N-di(hydrocarbon)-thiocarbamoyl-sulfanyl group," those groups in which and $R^{a3}$ and $R^{b3}$ are heterocyclic groups are referred to as "N,N-di(heterocyclic ring)-thiocarbamoyl-sulfanyl group," those groups in which $R^{a3}$ is a hydrocarbon group and $R^{b3}$ is a heterocyclic group are referred to as "N-hydrocarbon-N-heterocyclic ring-thiocarbamoyl-sulfanyl group," and those groups in which $R^{a3}$ and $R^{b3}$ combine to each other, together with the nitrogen atom to which they bind, to form a cyclic amino group are referred to as "cyclicamino-thiocarbonyl-sulfamoyl group."

Among the groups represented by the formula (ω-13C), those groups in which $R^{a3}$ is a hydrocarbon group are referred to as "N-hydrocarbon-sulfamoyl-sulfanyl group," and those groups in which $R^{a3}$ is a heterocyclic group are referred to as "N-heterocyclic ring-sulfamoyl-sulfanyl group."

Among the groups represented by the formula (ω-14C), those groups in which both $R^{a3}$ and $R^{b3}$ are hydrocarbon groups are referred to as "N,N-di(hydrocarbon)-sulfamoyl-sulfanyl group," those groups in which both $R^{a3}$ and $R^{b3}$ are heterocyclic groups are referred to as "N,N-di(heterocyclic ring)-sulfamoyl-sulfinyl group," those groups in which $R^{a3}$ is a hydrocarbon group and $R^{b3}$ is a heterocyclic group are referred to as "N-hydrocarbon-N-heterocyclic ring-sulfamoyl-sulfanyl group," and those groups in which $R^{a3}$ and $R^{b3}$ combine to each other, together with the nitrogen atom to which they bind, to form a cyclic amino group are referred to as "cyclicamino-sulfonyl-sulfanyl group."

Among the groups represented by the formula (ω-15C), those groups in which $R^{a3}$ is a hydrocarbon group are referred to as "N-hydrocarbon-sulfinamoyl-sulfanyl group," and those groups in which $R^{a3}$ is a heterocyclic group are referred to as "N-heterocyclic ring-sulfinamoyl-sulfanyl group."

Among the groups represented by the formula (ω-16C), those groups in which both $R^{a3}$ and $R^{b3}$ are hydrocarbon groups are referred to as "N,N-di(hydrocarbon)-sulfinamoyl-sulfanyl group," those groups in which both $R^{a3}$ and $R^{b3}$ are heterocyclic groups are referred to as "N,N-di(heterocyclic ring)-sulfinamoyl-sulfanyl group," those groups in which $R^{a3}$ is a hydrocarbon group and $R^{b3}$ is a heterocyclic group are referred to as "N-hydrocarbon-N-heterocyclic ring-sulfinamoyl-sulfanyl group," and those groups in which $R^{a3}$ and $R^{b3}$ combine to each other, together with the nitrogen atom to which they bind, to form a cyclic amino group are referred to as "cyclicamino-sulfanyl-sulfanyl group."

Among the groups represented by the formula (ω-17C), those groups in which $R^{a3}$ is a hydrocarbon group are referred to as "hydrocarbon-oxy-sulfonyl-sulfanyl group," and those groups in which $R^{a3}$ is a heterocyclic group are referred to as "heterocyclic ring-oxy-sulfonyl-sulfanyl group."

Among the groups represented by the formula (ω-18C), those groups in which $R^{a3}$ is a hydrocarbon group are referred to as "hydrocarbon-oxy-sulfinyl-sulfanyl group," and those groups in which $R^{a3}$ is a heterocyclic group are referred to as "heterocyclic ring-oxy-sulfinyl-sulfanyl group."

Among the groups represented by the formula (ω-19C), those groups in which both $R^{a3}$ and $R^{b3}$ are hydrocarbon groups are referred to as "O,O'-di(hydrocarbon)-phosphono-sulfanyl group," those groups in which both $R^{a3}$ and $R^{b3}$ are heterocyclic groups are referred to as "O,O'-di(heterocyclic ring)-phosphono-sulfanyl group," and those groups in which $R^{a3}$ is a hydrocarbon group and $R^{b3}$ is a heterocyclic group are referred to as "O-hydrocarbon-O'-heterocyclic ring-phosphono-sulfanyl group."

Among the groups represented by the formula (ω-20C), those groups in which $R^{a3}$ is a hydrocarbon group are referred to as "hydrocarbon-sulfonyl-sulfanyl group," and those groups in which $R^{a3}$ is a heterocyclic group are referred to as "heterocyclic ring-sulfonyl-sulfanyl group."

Among the groups represented by the formula (ω-21C), those groups in which $R^{a3}$ is a hydrocarbon group are referred to as "hydrocarbon-sulfinyl-sulfanyl group," and those groups in which $R^{a3}$ is a heterocyclic group are referred to as "heterocyclic ring-sulfinyl-sulfanyl group."

Examples of the hydrocarbon in the groups represented by the aforementioned formulas (ω-1C) through (ω-21C) include similar groups to the aforementioned hydrocarbon group. Examples of the hydrocarbon-carbonyl-sulfanyl group represented by the formula (ω-1C) include, for example, an alkyl-carbonyl-sulfanyl group, an alkenyl-carbonyl-sulfanyl group, an alkynyl-carbonyl-sulfanyl group, a cycloalkyl-carbonyl-sulfanyl group, a cycloalkenyl-carbonyl-sulfanyl group, a cycloalkanedienyl-carbonyl-sulfanyl group, a cycloalkyl-alkyl-carbonyl-sulfanyl group which are aliphatic hydrocarbon-carbonyl-sulfanyl groups; an aryl-carbonyl-sulfanyl group; an aralkyl-carbonyl-sulfanyl group; a bridged cyclic hydrocarbon-carbonyl-sulfanyl group; a spiro cyclic hydrocarbon-carbonyl-sulfanyl group; and a terpene family hydrocarbon-carbonyl-sulfanyl group. In the following descriptions, groups represented by the formulas (ω-2C) through (ω-21C) are similar to those explained above.

Examples of the heterocyclic ring in the groups represented by the aforementioned formulas (ω-1C) through (ω-21C) include similar groups to the aforementioned heterocyclic group. Examples of the heterocyclic ring-carbonyl-sulfanyl group represented by the formula (ω-1C) include, for example, a monocyclic heteroaryl-carbonyl-sulfanyl group, a fused polycyclic heteroaryl-carbonyl-sulfanyl group, a monocyclic non-aromatic heterocyclic ring-carbonyl-sulfanyl group, and a fused polycyclic non-aromatic heterocyclic ring-carbonyl-sulfanyl group. In the following descriptions, groups represented by the formula (ω-2C) through (ω-21C) are similar to those groups explained above.

Examples of the cyclic amino in the groups represented by the aforementioned formulas (ω-10C) through (ω-16C) include similar groups to the aforementioned cyclic amino group.

The aforementioned acyl-sulfanyl group, hydrocarbon-sulfanyl group, and heterocyclic-sulfanyl group are generically referred to as "substituted sulfanyl group." Moreover, these substituted sulfanyl group and sulfanyl group are generically referred to as "sulfanyl group which may be substituted."

Examples of the N-hydrocarbon-amino group include the groups in which one hydrogen atom of amino group is substituted with a hydrocarbon group, and include, for example, an N-alkyl-amino group, an N-alkenyl-amino group, an N-alkynyl-amino group, an N-cycloalkyl-amino group, an N-cycloalkyl-alkyl-amino group, an N-aryl-amino group, and an N-aralkyl-amino group.

Examples of the N-alkyl-amino group include, for example, methylamino, ethylamino, n-propylamino, isopropylamino, n-butylamino, isobutylamino, sec-butylamino, tert-butylamino, n-pentylamino, isopentylamino, (2-methylbutyl)amino, (1-methylbutyl)amino, neopentylamino, (1,2-dimethylpropyl)amino, (1-ethylpropyl)amino, n-hexylamino, (4-methylpentyl)amino, (3-methylpentyl)amino, (2-methylpentyl)amino, (1-methylpentyl)amino, (3,3-dimethylbutyl)amino, (2,2-dimethylbutyl)amino, (1,1-dimethylbutyl)amino, (1,2-dimethylbutyl)amino, (1,3-dimethylbutyl)amino, (2,3-dimethylbutyl)amino, (2-ethylbutyl)amino, (1-ethylbutyl)amino, (1-ethyl-1-methylpropyl)amino, n-heptylamino, n-octylamino, n-nonylamino, n-decylamino, n-undecylamino, n-dodecylamino, n-tridecylamino, n-tetradecylamino, and n-pentadecylamino, which are $C_1$ to $C_{15}$ straight chain or branched chain N-alkyl amino groups.

Examples of the N-alkenyl-amino group include, for example, vinyl amino, (prop-1-en-1-yl)amino, allylamino, isopropenylamino, (but-1-en-1-yl)amino, (but-2-en-1-yl)amino, (but-3-en-1-yl)amino, (2-methylprop-2-en-1-yl)amino, (1-methylprop-2-en-1-yl)amino, (pent-1-en-1-yl)amino, (pent-2-en-1-yl)amino, (pent-3-en-1-yl)amino, (pent-4-en-1-yl)amino, (3-methylbut-2-en-1-yl)amino, (3-methylbut-3-en-1-yl)amino, (hex-1-en-1-yl)amino, (hex-2-en-1-yl)amino, (hex-3-en-1-yl)amino, (hex-4-en-1-yl)amino, (hex-5-en-1-yl)amino, (4-methylpent-3-en-1-yl)amino, (4-methylpent-3-en-1-yl)amino, (hept-1-en-1-yl)amino, (hept-6-en-1-yl)amino, (oct-1-en-1-yl)amino, (oct-7-en-1-yl)amino, (non-1-en-1-yl)amino, (non-8-en-1-yl)amino, (dec-1-en-1-yl)amino, (dec-9-en-1-yl)amino, (undec-1-en-1-yl)amino, (undec-10-en-1-yl)amino, (dodec-1-en-1-yl)amino, (dodec-11-en-1-yl)amino, (tridec-1-en-1-yl)amino, (tridec-12-en-1-yl)amino, (tetradec-1-en-1-yl)amino, (tetradec-13-en-1-yl)amino, (pentadec-1-en-1-yl)amino, and (pentadec-14-en-1-yl)amino, which are $C_2$ to $C_{15}$ straight chain or branched chain N-alkenyl amino groups.

Examples of the N-alkynyl-amino group include, for example, ethynylamino, (prop-1-yn-1-yl)amino, (prop-2-yn-1-yl)amino, (but-1-yn-1-yl)amino, (but-3-yn-1-yl)amino, (1-methylprop-2-yn-1-yl)amino, (pent-1-yn-1-yl)amino, (pent-4-yn-1-yl)amino, (hex-1-yn-1-yl)amino, (hex-5-yn-1-yl)amino, (hept-1-yn-1-yl)amino, (hept-6-yn-1-yl)amino, (oct-1-yn-1-yl)amino, (oct-7-yn-1-yl)amino, (non-1-yn-1-yl)amino, (non-8-yn-1-yl)amino, (dec-1-yn-1-yl)amino, (dec-9-yn-1-yl)amino, (undec-1-yn-1-yl)amino, (undec-10-yn-1-yl)amino, (dodec-1-yn-1-yl)amino, (dodec-11-yn-1-yl)amino, (tridec-1-yn-1-yl)amino, (tridec-12-yn-1-yl)amino, (tetradec-1-yn-1-yl)amino, (tetradec-13-yn-1-yl)amino, (pentadec-1-yn-1-yl)amino, and (pentadec-14-yn-1-yl)amino, which are $C_2$ to $C_{15}$ straight chain or branched chain N-alkynyl-amino groups.

Examples of the N-cycloalkyl-amino group include, for example, cyclopropylamino, cyclobutylamino, cyclopentylamino, cyclohexylamino, cycloheptylamino, and cyclooctylamino, which are $C_3$ to $C_8$ N-cycloalkyl-amino groups.

Examples of the N-cycloalkyl-alkyl-amino group include, for example, (cyclopropylmethyl)amino, (1-cyclopropylethyl)amino, (2-cyclopropylethyl)amino, (3-cyclopropylpropyl)amino, (4-cyclopropylbutyl)amino, (5-cyclopropylpentyl)amino, (6-cyclopropylhexyl)amino, (cyclobutylmethyl)amino, (cyclopentylmethyl)amino, (cyclobutylmethyl)amino, (cyclopentylmethyl)amino, (cyclohexylmethyl)amino, (2-cyclohexylethyl)amino, (3-cyclohexylpropyl)amino, (4-cyclohexylbutyl)amino, (cycloheptylmethyl)amino, (cyclooctylmethyl)amino, and (6-cyclooctylhexyl)amino, which are $C_4$ to $C_{14}$ N-cycloalkyl-alkyl-amino groups.

Examples of the N-aryl-amino group include, for example, phenylamino, 1-naphthylamino, 2-naphtylamino, anthrylamino, phenanthrylamino, and acenaphthylenylamino, which are $C_6$ to $C_{14}$ N-mono-arylamino groups.

Examples of the N-aralkyl-amino group include, for example, benzylamino, (1-naphthylmethyl)amino, (2-naphthylmethyl)amino, (anthracenylmethyl)amino, (phenanthrenylmethyl)amino, (acenaphthylenylmethyl)amino, (diphenylmethyl)amino, (1-phenethyl)amino, (2-phenethyl)amino, (1-(1-naphthyl)ethyl)amino, (1-(2-naphthyl)ethyl)amino, (2-(1-naphthyl)ethyl)amino, (2-(2-naphthyl)ethyl)amino, (3-phenylpropyl)amino, (3-(1-naphthyl)propyl)amino, (3-(2-naphthyl)propyl)amino, (4-phenylbutyl)amino, (4-(1-naphthyl)butyl)amino, (4-(2-naphthyl)butyl)amino, (5-phenylpentyl)amino, (5-(1-naphthyl)pentyl)amino, (5-(2-naphthyl)pentyl)amino, (6-phenylhexyl)amino, (6-(1-naphthyl)hexyl)amino, and (6-(2-naphthyl)hexyl)amino, which are $C_7$ to $C_{16}$ N-aralkyl-amino groups.

Examples of the N,N-di(hydrocarbon)-amino group include the groups in which two hydrogen atoms of amino group are substituted with hydrocarbon groups, and include, for example, N,N-dimethylamino, N,N-diethylamino, N-ethyl-N-methylamino, N,N-di-n-propylamino, N,N-diisopropylamino, N-allyl-N-methylamino, N-(prop-2-yn-1-yl)-N-methylamino, N,N-dicyclohexylamino, N-cyclohexyl-N-methylamino, N-cyclohexylmethylamino-N-methylamino, N,N-diphenylamino, N-methyl-N-phenylamino, N,N-dibenzylamino, and N-benzyl-N-methylamino.

Examples of the N-heterocyclic ring-amino group include the groups in which one hydrogen atom of amino group is substituted with a heterocyclic group, and include, for example, (3-pyrrolidinyl)amino, (4-piperidinyl)amino, (2-tetrahydropyranyl)amino, (3-indolinyl)amino, (4-chromanyl)amino, (3-thienyl)amino, (3-pyridyl)amino, (3-quinolyl)amino, and (5-indolyl)amino.

Examples of the N-hydrocarbon-N-heterocyclic ring-amino group include the groups in which two hydrogen atoms of amino group are substituted with hydrocarbon group and heterocyclic group respectively, and include, for example, N-methyl-N-(4-piperidinyl)amino, N-(4-chromanyl)-N-methylamino, N-methyl-N-(3-thienyl)amino, N-methyl-N-(3-pyridyl)amino, N-methyl-N-(3-quinolyl)amino.

Examples of the acyl-amino group include the groups in which one hydrogen atom of the amino group is substituted with an acyl group, and include, for example, formylamino group, glyoxyloylamino group, thioformylamino group, and groups represented by the following formulas:

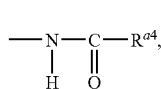

(ω-1D)

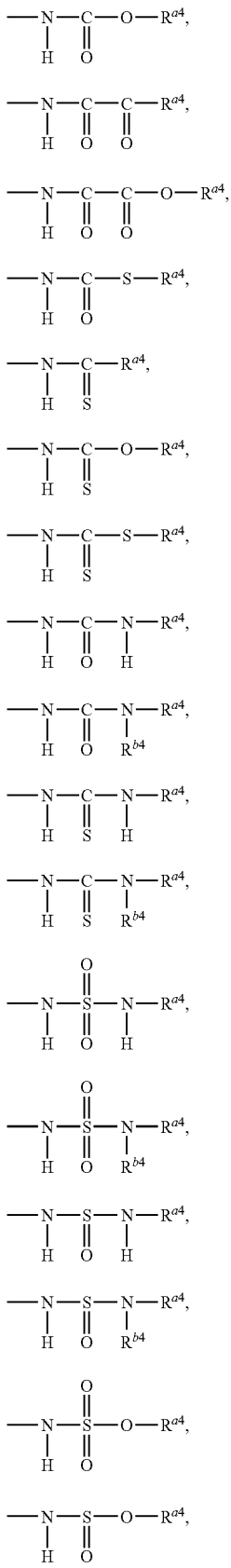
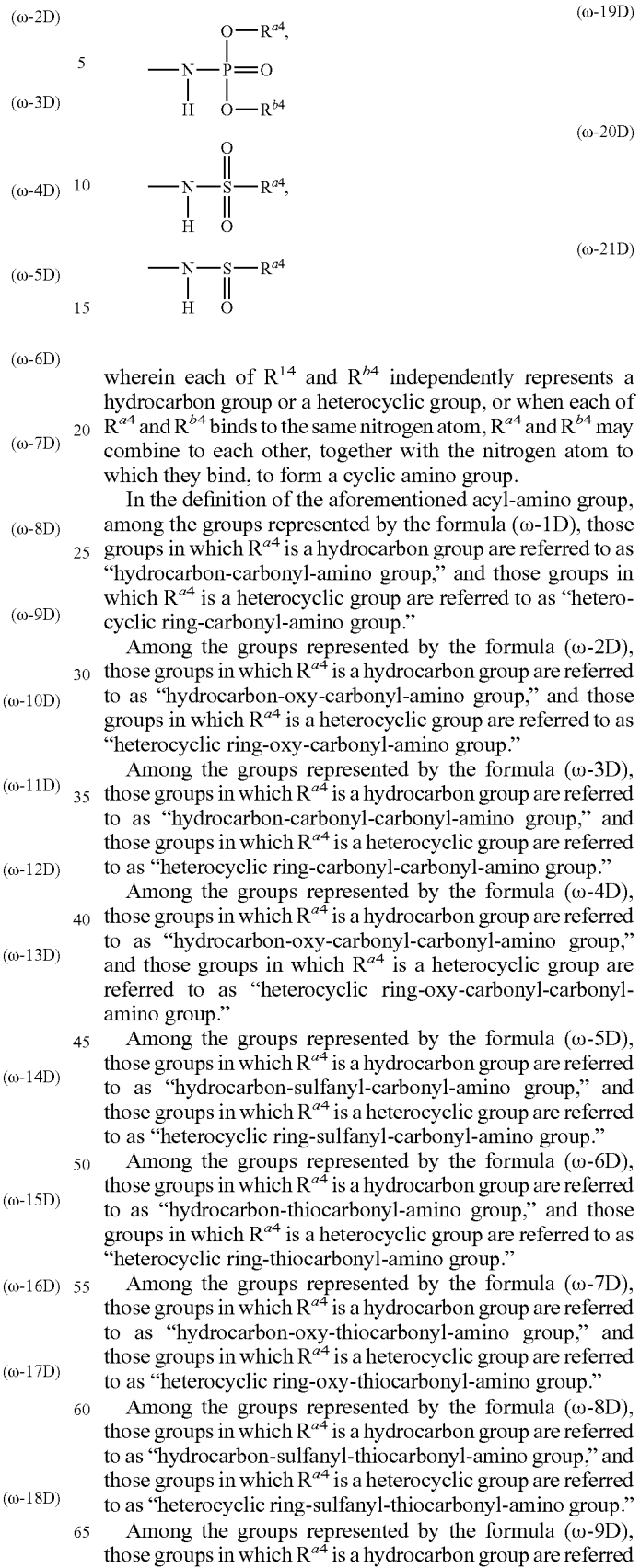

wherein each of $R^{a4}$ and $R^{b4}$ independently represents a hydrocarbon group or a heterocyclic group, or when each of $R^{a4}$ and $R^{b4}$ binds to the same nitrogen atom, $R^{a4}$ and $R^{b4}$ may combine to each other, together with the nitrogen atom to which they bind, to form a cyclic amino group.

In the definition of the aforementioned acyl-amino group, among the groups represented by the formula (ω-1D), those groups in which $R^{a4}$ is a hydrocarbon group are referred to as "hydrocarbon-carbonyl-amino group," and those groups in which $R^{a4}$ is a heterocyclic group are referred to as "heterocyclic ring-carbonyl-amino group."

Among the groups represented by the formula (ω-2D), those groups in which $R^{a4}$ is a hydrocarbon group are referred to as "hydrocarbon-oxy-carbonyl-amino group," and those groups in which $R^{a4}$ is a heterocyclic group are referred to as "heterocyclic ring-oxy-carbonyl-amino group."

Among the groups represented by the formula (ω-3D), those groups in which $R^{a4}$ is a hydrocarbon group are referred to as "hydrocarbon-carbonyl-carbonyl-amino group," and those groups in which $R^{a4}$ is a heterocyclic group are referred to as "heterocyclic ring-carbonyl-carbonyl-amino group."

Among the groups represented by the formula (ω-4D), those groups in which $R^{a4}$ is a hydrocarbon group are referred to as "hydrocarbon-oxy-carbonyl-carbonyl-amino group," and those groups in which $R^{a4}$ is a heterocyclic group are referred to as "heterocyclic ring-oxy-carbonyl-carbonyl-amino group."

Among the groups represented by the formula (ω-5D), those groups in which $R^{a4}$ is a hydrocarbon group are referred to as "hydrocarbon-sulfanyl-carbonyl-amino group," and those groups in which $R^{a4}$ is a heterocyclic group are referred to as "heterocyclic ring-sulfanyl-carbonyl-amino group."

Among the groups represented by the formula (ω-6D), those groups in which $R^{a4}$ is a hydrocarbon group are referred to as "hydrocarbon-thiocarbonyl-amino group," and those groups in which $R^{a4}$ is a heterocyclic group are referred to as "heterocyclic ring-thiocarbonyl-amino group."

Among the groups represented by the formula (ω-7D), those groups in which $R^{a4}$ is a hydrocarbon group are referred to as "hydrocarbon-oxy-thiocarbonyl-amino group," and those groups in which $R^{a4}$ is a heterocyclic group are referred to as "heterocyclic ring-oxy-thiocarbonyl-amino group."

Among the groups represented by the formula (ω-8D), those groups in which $R^{a4}$ is a hydrocarbon group are referred to as "hydrocarbon-sulfanyl-thiocarbonyl-amino group," and those groups in which $R^{a4}$ is a heterocyclic group are referred to as "heterocyclic ring-sulfanyl-thiocarbonyl-amino group."

Among the groups represented by the formula (ω-9D), those groups in which $R^{a4}$ is a hydrocarbon group are referred to as "N-hydrocarbon-carbamoyl group," and those groups in which $R^{a4}$ is a heterocyclic group are referred to as "N-heterocyclic ring-carbamoyl-amino group."

Among the groups represented by the formula (ω-10D), those groups in which both $R^{a4}$ and $R^{b4}$ are hydrocarbon groups are referred to as "N,N-di(hydrocarbon)-carbamoyl-amino group," those groups in which both $R^{a4}$ and $R^{b4}$ are heterocyclic groups are referred to as "N,N-di(heterocyclic ring)-carbamoyl-amino group," those groups in which $R^{a4}$ is a hydrocarbon group and $R^{b4}$ is a heterocyclic group are referred to as "N-hydrocarbon-N-heterocyclic ring-carbamoyl-amino group," and those groups in which $R^{a4}$ and $R^{b4}$ combine to each other, together with the nitrogen atom to which they bind, to form a cyclic amino group are referred to as "cyclic amino-carbonyl-amino group."

Among the groups represented by the formula (ω-11D), those groups in which $Ra^4$ is a hydrocarbon group are referred to as "N-hydrocarbon-thiocarbamoyl-amino group," and those groups in which $R^{a4}$ is a heterocyclic ring group are referred to as "N-heterocyclic-thiocarbamoyl-amino group."

Among the groups represented by the formula (ω-12D), those groups in which both $R^{a4}$ and $R^{b4}$ are hydrocarbon groups are referred to as "N,N-di(hydrocarbon)-thiocarbamoyl-amino group," those groups in which both $R^{a4}$ and $R^{b4}$ are heterocyclic groups are referred to as "N,N-di(heterocyclic ring)-thiocarbamoyl-amino group," those groups in which $R^{a4}$ is a hydrocarbon group and $R^{b4}$ is a heterocyclic group are referred to as "N-hydrocarbon-N-heterocyclic ring-thiocarbamoyl-amino group," and those groups in which $R^{a4}$ and $R^{b4}$ combine to each other, together with the nitrogen atom to which they bind, to form a cyclic amino group are referred to as "cyclic amino-thiocarbonyl-amino group."

Among the groups represented by the formula (ω-13D), those groups in which $R^{a4}$ is a hydrocarbon group are referred to as "N-hydrocarbon-sulfamoyl-amino group," and those groups in which $R^{a4}$ is a heterocyclic group are referred to as "N-heterocyclic ring-sulfamoyl-amino group."

Among the groups represented by the formula (ω-14D), those groups in which both $R^{a4}$ and $R^{b4}$ are hydrocarbon groups are referred to as "di(hydrocarbon)-sulfamoyl-amino group," those groups in which both $R^{a4}$ and $R^{b4}$ are heterocyclic groups are referred to as "N,N-di(heterocyclic ring)-sulfamoyl-amino group," those groups in which $R^{a4}$ is a hydrocarbon group and $R^{b4}$ is a heterocyclic group are referred to as "N-hydrocarbon-N-heterocyclic ring-sulfamoyl-amino group," and those groups in which $R^{a4}$ and $R^{b4}$ combine to each other, together with the nitrogen atom to which they bind, to form a cyclic amino group are referred to as "cyclic amino-sulfonyl-amino group."

Among the groups represented by the formula (ω-15D), those groups in which $R^{a4}$ is a hydrocarbon group are referred to as "N-hydrocarbon-sulfinamoyl-amino group," and those groups in which $R^{a4}$ is a heterocyclic group are referred to as "N-heterocyclic ring-sulfinamoyl-amino group."

Among the groups represented by the formula (ω-16D), those groups in which both $R^{a4}$ and $R^{b4}$ are hydrocarbon groups are referred to as "N,N-di(hydrocarbon)-sulfinamoyl-amino group," those groups in which both $R^{a4}$ and $R^{b4}$ are heterocyclic groups are referred to as "N,N-di(heterocyclic ring)-sulfinamoyl-amino group," groups in which $R^{a4}$ is a hydrocarbon group and $R^{b4}$ is a heterocyclic group are referred to as "N-hydrocarbon-N-heterocyclic ring-sulfinamoyl-amino group," and those groups in which $R^{a4}$ and $R^{b4}$ combine to each other, together with the nitrogen atom to which they bind, to form a cyclic amino group are referred to as "cyclic amino-sulfinyl-amino group."

Among the groups represented by the formula (ω-17D), those groups in which $R^{a4}$ is a hydrocarbon group are referred to as "hydrocarbon-oxy-sulfonyl-amino group," and those groups in which $R^{a4}$ is a heterocyclic group are referred to as "heterocyclic ring-oxy-sulfoyl-amino group."

Among the groups represented by the formula (ω-18D), those groups in which $R^{a4}$ is a hydrocarbon group are referred to as "hydrocarbon-oxy-sulfinyl-amino group," and those groups in which $R^{a4}$ is a heterocyclic group are referred to as "heterocyclic ring-oxy-sulfinyl-amino group."

Among the groups represented by the formula (ω-19D), those groups in which both $R^{a4}$ and $R^{b4}$ are hydrocarbon groups are referred to as "O,O'-di(hydrocarbon)-phosphono-amino group," those groups in which both $R^{a4}$ and $R^{b4}$ are heterocyclic groups are referred to as "O,O'-di(heterocyclic ring)-phosphono-amino group," and those groups in which $R^{a4}$ is a hydrocarbon group and $R^{b4}$ is a heterocyclic group are referred to as "O-hydrocarbon-O'-heterocyclic ring-phosphono-amino group."

Among the groups represented by the formula (ω-20D), those groups in which $R^{a4}$ is a hydrocarbon group are referred to as "hydrocarbon-sulfonyl-amino group," and those groups in which $R^{a4}$ is a heterocyclic group are referred to as "heterocyclic ring-sulfonyl-amino group."

Among the groups represented by the formula (ω-21D), those groups in which $R^{a4}$ is a hydrocarbon group are referred to as "hydrocarbon-sulfinyl-amino group," and those groups in which $R^{a4}$ is a heterocyclic group are referred to as "heterocyclic ring-sulfinyl-amino group."

Examples of the hydrocarbon in the groups represented by the aforementioned formulas (ω-1D) through (ω-21D) include the similar groups to the aforementioned hydrocarbon group. Examples of the hydrocarbon-carbonyl-amino groups represented by the formula (ω-1D) include, for example, an alkyl-carbonyl-amino group, an alkenyl-carbonyl-amino group, an alkynyl-carbonyl-amino group, a cycloalkyl-carbonyl-amino group, a cycloalkenyl-carbonyl-amino group, a cycloalkanedienyl-carbonyl-amino group, a cycloalkyl-alkyl-carbonyl-amino group which are aliphatic hydrocarbon-carbonyl-amino groups; an aryl-carbonyl-amino group; an aralkyl-carbonyl-amino group; a bridged cyclic hydrocarbon-carbonyl-amino group; a spiro cyclic hydrocarbon-carbonyl-amino group; and a terpene family hydrocarbon-carbonyl-amino group. In the following descriptions, groups represented by the formulas (ω-2D) through (ω-21D) are similar to those explained above.

Examples of the heterocyclic ring in the groups represented by the aforementioned formulas (ω-1D) through (ω-21D) include similar groups to the aforementioned heterocyclic group. Examples of the heterocyclic ring-carbonyl-amino group represented by the formula (ω-1D) include, for example, a monocyclic heteroaryl-carbonyl-amino group, a fused polycyclic heteroaryl-carbonyl-amino group, a monocyclic non-aromatic heterocyclic-carbonyl-amino group, and a fused polycyclic non-aromatic heterocyclic-carbonyl-amino group. In the following descriptions, groups represented by the formulas (ω-2D) through (ω-21D) are similar to those groups explained above.

Examples of the cyclic amino in the groups represented by the aforementioned formulas (ω-10D) through (ω-16D) include similar groups to the aforementioned cyclic amino group.

Examples of the di(acyl)-amino group include the groups in which two hydrogen atoms of amino group are substituted with acyl groups in the definitions of the aforementioned substituents according to "which may be substituted." Examples include, for example, di(formyl)-amino group, di(glyoxyloyl)-amino group, di(thioformyl)-amino group, and groups represented by the following formulas:

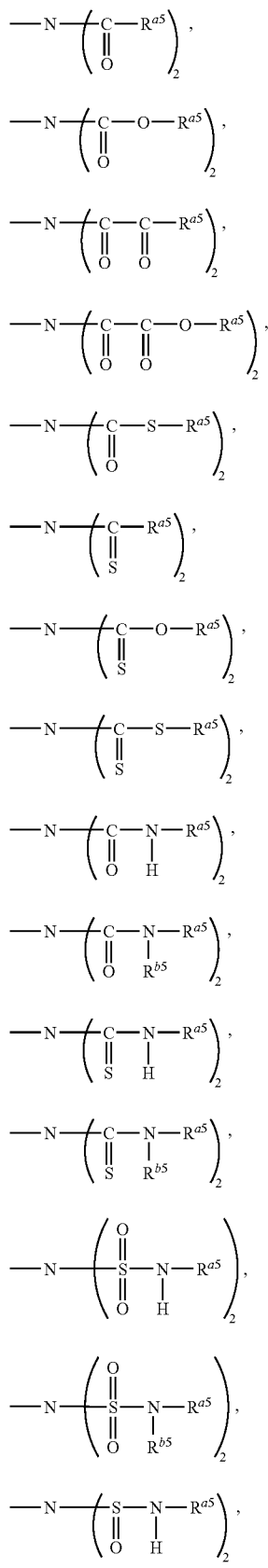

wherein each of $R^{a5}$ and $R^{b5}$ independently represents a hydrocarbon group or a heterocyclic group, or when each of $R^{a5}$ and $R^{b5}$ binds to the same nitrogen atom, $R^{a5}$ and $R^{b5}$ may combine to each other, together with the nitrogen atom to which they bind, to form a cyclic amino group.

In the definition of aforementioned di(acyl)-amino group, among the groups represented by the formula (ω-1E), those groups in which $R^{a5}$ is a hydrocarbon group are referred to as "bis(hydrocarbon-carbonyl)-amino group," and those groups in which $R^{a5}$ is a heterocyclic group are referred to as "bis(heterocyclic ring-carbonyl)-amino group."

Among the groups represented by the formula (ω-2E), those groups in which $R^{a5}$ is a hydrocarbon group are referred to as "bis(hydrocarbon-oxy-carbonyl)-amino group," and those groups in which $R^{a5}$ is a heterocyclic group are referred to as "bis(heterocyclic ring-oxy-carbonyl)-amino group."

Among the groups represented by the formula (ω-3E), those groups in which $R^{a5}$ is a hydrocarbon group are referred to as "bis(hydrocarbon-carbonyl-carbonyl)-amino group," and those groups in which $R^{a5}$ is a heterocyclic group are referred to as "bis(heterocyclic ring-carbonyl-carbonyl)-amino group."

Among the groups represented by the formula (ω-4E), those groups in which $R^{a5}$ is a hydrocarbon group are referred to as "bis(hydrocarbon-oxy-carbonyl-carbonyl)-amino group," and those groups in which $R^{a5}$ is a heterocyclic group are referred to as "bis(heterocyclic ring-oxy-carbonyl-carbonyl)-amino group."

Among the groups represented by the formula (ω-5E), those groups in which $R^{a5}$ is a hydrocarbon group are referred to as "bis(hydrocarbon-sulfanyl-carbonyl)-amino group," and those groups in which $R^{a5}$ is a heterocyclic group are referred to as "bis(heterocyclic ring-sulfanyl-carbonyl)-amino group."

Among the groups represented by the formula (ω-6E), those groups in which $R^{a5}$ is a hydrocarbon group are referred to as "bis(hydrocarbon-thiocarbonyl)-amino group," and those groups in which $R^{a5}$ is a heterocyclic group are referred to as "bis(heterocyclic ring-thiocarbonyl)-amino group."

Among the groups represented by the formula (ω-7E), those groups in which $R^{a5}$ is a hydrocarbon group are referred to as "bis(hydrocarbon-oxy-thiocarbonyl)-amino group," and those groups in which $R^{a5}$ is a heterocyclic group are referred to as "bis(heterocyclic ring-oxy-thiocarbonyl)-amino group."

Among the groups represented by the formula (ω-8E), those groups in which $R^{a5}$ is a hydrocarbon group are referred to as "bis(hydrocarbon-sulfanyl-thiocarbonyl)-amino group," and those groups in which $R^{a5}$ is a heterocyclic group are referred to as "bis(heterocyclic ring-sulfanyl-thiocarbonyl)-amino group."

Among the groups represented by the formula (ω-9E), those groups in which $R^{a5}$ is a hydrocarbon group are referred to as "bis(N-hydrocarbon-carbamoyl)-amino group," and those groups in which $R^{a5}$ is a heterocyclic group are referred to as "bis(N-heterocyclic ring-carbamoyl)-amino group."

Among the groups represented by the formula (ω-10E), those groups in which both $R^{a5}$ and $R^{b5}$ are hydrocarbon groups are referred to as "bis[N,N-di(hydrocarbon)-carbamoyl]-amino group," those groups in which both $R^{a5}$ and $R^{b5}$ are heterocyclic groups are referred to as "bis[N,N-di(heterocyclic ring)-carbamoyl]-amino group," groups in which $R^{a5}$ is a hydrocarbon group and $R^{b5}$ is a heterocyclic group are referred to as "bis(N-hydrocarbon-N-heterocyclic ring-carbamoyl)-amino group," and those groups in which $R^{a5}$ and $R^{b5}$ combine to each other, together with the nitrogen atom to which they bind, to form a cyclic amino groups are referred to as "bis(cyclic amino-carbonyl)amino group."

Among the groups represented by the formula (ω-11E), those groups in which $R^{a5}$ is a hydrocarbon group are referred to as "bis(N-hydrocarbon-thiocarbamoyl)-amino group," and those groups in which $R^{a5}$ is a heterocyclic group are referred to as "bis(N-heterocyclic ring-thiocarbamoyl)-amino group."

Among the groups represented by the formula (ω-12E), those groups in which both $R^{a5}$ and $R^{b5}$ are hydrocarbon groups are referred to as "bis[N,N-di(hydrocarbon)-thiocarbamoyl]-amino group," those groups in which both $R^{a5}$ and $R^{b5}$ are heterocyclic groups are referred to as "bis[N,N-di(heterocyclic ring)-thiocarbamoyl]-amino group," those groups in which $R^{a5}$ is a hydrocarbon group and $R^{b5}$ is a heterocyclic group are referred to as "bis(N-hydrocarbon-N-heterocyclic ring-thiocarbamoyl)-amino group," and those groups in which $R^{a5}$ and $R^{b5}$ combine to each other, together with the nitrogen atom to which they bind, to form a cyclic amino group are referred to as "bis(cyclic amino-thiocarbonyl)-amino group."

Among the groups represented by the formula (ω-13E), those groups in which $R^{a5}$ is a hydrocarbon group are referred to as "bis(N-hydrocarbon-sulfamoyl)-amino group," and those groups in which $R^{a5}$ is a heterocyclic group are referred to as "bis(N-heterocyclic ring-sulfamoyl)-amino group."

Among the groups represented by the formula (ω-14E), those groups in which both $R^{a5}$ and $R^{b5}$ are hydrocarbon groups are referred to as "bis[N,N-di(hydrocarbon)-sulfamoyl]-amino group," those groups in which both $R^{a5}$ and $R^{b5}$ are heterocyclic groups are referred to as "bis[N,N-di(heterocyclic ring)-sulfamoyl]-amino group," those groups in which $R^{a5}$ is a hydrocarbon group and $R^{b5}$ is a heterocyclic group are referred to as "bis(N-hydrocarbon-N-heterocyclic ring-sulfamoyl)-amino group," and those groups in which $R^{a5}$ and $R^{b5}$ combine to each other, together with the nitrogen atom to which they bind, to form a cyclic amino group are referred to as "bis(cyclic amino-sulfonyl)amino group."

Among the groups represented by the formula (ω-15E), those groups in which $R^{a5}$ is a hydrocarbon group are referred to as "bis(N-hydrocarbon-sulfinamoyl)-amino group," and those groups in which $R^{a5}$ is a heterocyclic group are referred to as "bis(N-heterocyclic ring-sulfinamoyl)-amino group."

Among the groups represented by the formula (ω-16E), those groups in which $R^{a5}$ and $R^{b5}$ are hydrocarbon groups are referred to as "bis[N,N-di(hydrocarbon)-sulfinamoyl]-amino group," those groups in which $R^{a5}$ and $R^{b5}$ are heterocyclic groups are referred to as "bis[N,N-di(heterocyclic ring)-sulfinamoyl]-amino group," those groups in which $R^{a5}$ is a hydrocarbon group and $R^{b5}$ is a heterocyclic group are referred to as "bis(N-hydrocarbon-N-heterocyclic ring-sulfinamoyl)-amino group," and those groups in which $R^{a5}$ and $R^{b5}$ combine to each other, together with the nitrogen atom to which they bind, to form a cyclic amino group are referred to as "bis(cyclic amino-sulfinyl)amino group."

Among the groups represented by the formula (ω-17E), those groups in which $R^{a5}$ is a hydrocarbon group are referred to as "bis(hydrocarbon-oxy-sulfonyl)-amino group," and those groups in which $R^{a5}$ is a heterocyclic group are referred to as "bis(heterocyclic ring-oxy-sulfonyl)-amino group."

Among the groups represented by the formula (ω-18E), those groups in which $R^{a5}$ is a hydrocarbon group are referred to as "bis(hydrocarbon-oxy-sulfinyl)-amino group," and those groups in which $R^{a5}$ is a heterocyclic group are referred to as "bis(heterocyclic ring-oxy-sulfinyl)-amino group."

Among the groups represented by the formula (ω-19E), those groups in which both $R^{a5}$ and $R^{b5}$ are hydrocarbon groups are referred to as "bis[O,O'-di(hydrocarbon)-phosphono]-amino group," those groups in which both $R^{a5}$ and $R^{b5}$ are heterocyclic groups are referred to as "bis[O,O'-di(heterocyclic ring)-phosphono]-amino group," and those groups in which $R^{a5}$ is a hydrocarbon group and $R^{b5}$ is a heterocyclic group are referred to as "bis(O-hydrocarbon-O'-heterocyclic ring-phosphono)-amino group."

Among the groups represented by the formula (ω-20E), those groups in which $R^{a5}$ is a hydrocarbon group are referred to as "bis(hydrocarbon-sulfonyl)-amino group," and those groups in which $R^{a5}$ is a heterocyclic group are referred to as "bis( heterocyclic ring-sulfonyl)-amino group."

Among the groups represented by the formula (ω-21E), those groups in which $R^{a5}$ is a hydrocarbon group are referred to as "bis(hydrocarbon-sulfinyl)-amino group," and those groups in which $R^{a5}$ is a heterocyclic group are referred to as "bis(heterocyclic ring-sulfinyl)-amino group."

Examples of the hydrocarbon in the groups represented by the aforementioned formulas (ω-1E) through (ω-21E) include the similar groups to the aforementioned hydrocarbon group. Examples of the bis(hydrocarbon-carbonyl)-amino groups represented by the formula (ω-1E) include, for example, a bis(alkyl-carbonyl)-amino group, a bis(alkenyl-carbonyl)-amino group, a bis(alkynyl-carbonyl)-amino group, a bis(cycloalkyl-carbonyl)-amino group, a bis(cycloalkenyl-carbonyl)-amino group, a bis(cycloalkanedienyl-carbonyl)-amino group, a bis(cycloalkyl-alkyl-carbonyl)-amino group which are bis(aliphatic hydrocarbon-carbonyl)-amino groups; a bis(aryl-carbonyl)-amino group; a bis(aralkyl-carbonyl)-amino group; a bis(bridged cyclic hydrocarbon-carbonyl)-amino group; a bis(spiro cyclic hydrocarbon-carbonyl)-amino group; and a bis(terpene family hydrocarbon-carbonyl)-amino group. In the following descriptions, groups represented by the formulas (ω-2E) through (ω-21E) are similar to those explained above.

Examples of the heterocyclic ring in the groups represented by the aforementioned formulas (ω-1E) through (ω-21E) include similar groups to the aforementioned heterocyclic group. Examples of the bis(heterocyclic ring-carbonyl)-amino group represented by the formula (ω-1E) include, for example, a bis(monocyclic heteroaryl-carbonyl)-amino group, a bis(fused polycyclic heteroaryl-carbonyl)-amino group, a bis(monocyclic non-aromatic heterocyclic-carbonyl)-amino group, and a bis(fused polycyclic non-aromatic heterocyclic-carbonyl)-amino group. In the following descriptions, groups represented by the formulas (ω-2E) through (ω-21E) are similar to those groups explained above.

Examples of the cyclic amino in the groups represented by the aforementioned formulas (ω-1E) through (ω-16E) include similar groups to the aforementioned cyclic amino group.

The aforementioned acyl-amino group and di(acyl)-amino group are generically referred to as "acyl substituted amino group." Furthermore, the aforementioned N-hydrocarbon-amino group, N,N-di(hydrocarbon)-amino group, N-heterocyclic-amino group, N-hydrocarbon-N-heterocyclic-amino group, cyclic amino group, acyl-amino group, and di(acyl)-amino group are generically referred to as "substituted amino group." Furthermore, these substituted amino group and amino group are generically referred to as "amino group which may be substituted."

In the following descriptions, compounds represented by the aforementioned general formula (I) are explained in details.

Examples of the "acyl group" in the definition of A include similar groups to the "acyl group" in the aforementioned definition.

A represents hydrogen atom or an acyl group. Hydrogen atom, "hydrocarbon-carbonyl group," and "hydrocarbon-sulfonyl group" are preferred, and hydrogen atom, acetyl group, and para-toluenesulfonyl group are more preferred.

X represents oxygen atom or NH.

One of $R^1$ and $R^2$ represents hydrogen atom and the other represents the formula —X-A. The compounds wherein $R^1$ is the formula —X-A and $R^2$ is hydrogen atom are preferred. The compounds wherein $R^1$ is the formula —O-A and $R^2$ is hydrogen atom are more preferred, and the compounds wherein A is hydrogen atom, acetyl group or para-toluenesulfonyl group are particularly preferred.

Y represents a sulfonyl group (—SO$_2$—) or a carbonyl group (—CO—). Sulfonyl group is preferred.

Examples of the "cyclic group" of "cyclic group which may be substituted" in the definition of $R^5$ include similar groups to the "cyclic group" in the aforementioned definition. Aromatic ring group, and cycloalkyl group are preferred, and phenyl group, naphthyl group, furyl group, pyridyl group, benzimidazolyl group, and cyclohexyl group are more preferred, and phenyl group is most preferred.

Examples of the "substituent" in the definition of "cyclic group which may be substituted" in the definition of $R^5$ include similar groups to the "substituent" explained for the aforementioned definition "which may be substituted." Halogen atom such as chlorine atom and fluorine atom; nitro group; alkyl group such as methyl group and tert-butyl group; halogenated alkyl group such as trifluoromethyl group; hydroxy group; alkoxy group such as methoxy group; alkylenedioxy group such as methylenedioxy group; amino group; N,N-di(hydrocarbon)-amino group such as dimethylamino group; and hydrocarbon-sulfonyl group such as methanesulfonyl group are preferred.

$R^5$ represents a cyclic group which may be substituted. Phenyl group, 2,6-difluorophenyl group, 2,4-dichlorophenyl group, 3-nitrophenyl group, 4-nitrophenyl group, 2-methylphenyl group, 4-(tert-butyl)phenyl group, 2-(trifluoromethyl)phenyl group, 4-(trifluoromethyl)phenyl group, 3,4-dihydroxyphenyl group, 2-methoxyphenyl group, 3-methoxyphenyl group, 2,3-dimethoxyphenyl group, 3,5-dimethoxyphenyl group, 3,4-methylenedioxyphenyl group, 3-aminophenyl group, 4-(dimethylamino)phenyl group, 4-methanesulfonylphenyl group, 1-naphthyl group, 5-methylfuran-2-yl group, pyridin-2-yl group, benzimidazol-2-yl group, and cyclohexyl group are preferred, and phenyl group, 4-(tert-butyl)phenyl group, and 2,3-dimethoxyphenyl group are more preferred.

Examples of the "substituent" in the definition of "$C_1$ to $C_4$ alkylene group which may be substituted" in the definition of Z include similar groups to the "substituent" explained for the aforementioned definition "which may be substituted."

Examples of the "$C_1$ to $C_4$ alkylene group" of "$C_1$ to $C_4$ alkylene group which may be substituted" in the definition of Z include straight chain or branched chain $C_1$ to $C_4$ alkylene groups such as methylene group, ethylene group, ethane-1,1-diyl group, propane-1,3-diyl group, propane-1,2-diyl group, propane-2,2-diyl group, or butane-1,4-diyl group.

Z represents a single bond or a $C_1$ to $C_4$ alkylene group which may be substituted. A single bond, methylene group, ethylene group, and ethane-1,1-diyl group are preferred, and methylene group is more preferred.

When Z is substituted, said substituent may bind to $R^5$ to form a cyclic group. Specific examples of these compounds include, for example, the compounds wherein the formula -Z-$R^5$ is 1,2,3,4-tetrahydroisoquinolin-2-yl group or the like.

Examples of the "substituent" in the definition of "$C_1$ to $C_6$ alkyl group which may be substituted" in the definition of $R^6$ include similar groups to the "substituent" explained for the aforementioned definition "which may be substituted."

Examples of the "$C_1$ to $C_6$ alkyl group" of "$C_1$ to $C_6$ alkyl group which may be substituted" in the definition of $R^6$ include a straight chain or a branched chain $C_1$ to $C_6$ alkyl group such as methyl group, ethyl group, n-propyl group, isopropyl group, n-butyl group, isobutyl group, sec-butyl group, tert-butyl group, n-pentyl group, n-hexyl group and the like.

$R^6$ represents hydrogen atom or a $C_1$ to $C_6$ alkyl group which may be substituted. Hydrogen atom and methyl group are preferred, and hydrogen atom is more preferred.

$R^6$ may bind to Z or $R^5$ to form a cyclic group. Specific examples of these compounds include, for example, the compounds wherein the following formula:

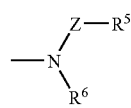

is 1,2,3,4-tetrahydroisoquinolin-2-yl group, 3-phenylpiperidin-1-yl group or the like.

One of $R^3$ and $R^4$ represents hydrogen atom and the other represents the following formula.

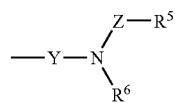

The compounds wherein R³ is the following formula:

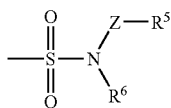

and R⁴ is hydrogen atom;

wherein R³ is hydrogen atom and R⁴ is the following formula;

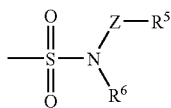

and wherein R³ is the following formula:

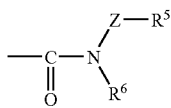

and R⁴ is hydrogen atom are preferred.

The compounds wherein R³ is the following formula:

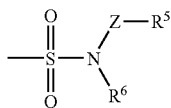

and R⁴ is hydrogen atom; and wherein R³ is hydrogen atom and R⁴ is the following formula:

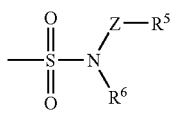

are more preferred.

The following compounds are preferred as the compound represented by the general formula (I). The compound numbers correspond to those in the table shown below.

N-Benzyl-5-{[(4-methylphenyl)sulfonyl]oxy}naphthalene-1-sulfonamide (Compound No. 1-1);
N-(2,6-Difluorobenzyl)-5-{[(4-methylphenyl)sulfonyl]oxy}naphthalene-1-sulfonamide (Compound No. 1-2);
N-(2,4-Dichlorobenzyl)-5-{[(4-methylphenyl)sulfonyl]oxy}naphthalene-1-sulfonamide (Compound No. 1-3);
N-(3-Nitrobenzyl)-5-{[(4-methylphenyl)sulfonyl]oxy}naphthalene-1-sulfonamide (Compound No. 1-4);
N-(4-Nitrobenzyl)-5-{[(4-methylphenyl)sulfonyl]oxy}naphthalene-1-sulfonamide (Compound No. 1-5);
N-(2-Methylbenzyl)-5-{[(4-methylphenyl)sulfonyl]oxy}naphthalene-1-sulfonamide (Compound No. 1-6);
N-[4-(tert-Butyl)benzyl]-5-{[(4-methylphenyl)sulfonyl]oxy}naphthalene-1-sulfonamide (Compound No. 1-7);
N-[2-(Trifluoromethyl)benzyl]-5-{[(4-methylphenyl)sulfonyl]oxy}naphthalene-1-sulfonamide (Compound No. 1-8);
N-[4-(Trifluoromethyl)benzyl]-5-{[(4-methylphenyl)sulfonyl]oxy}naphthalene-1-sulfonamide (Compound No. 1-9);
N-(3,4-Dihydroxybenzyl)-5-{[(4-methylphenyl)sulfonyl]oxy}naphthalene-1-sulfonamide (Compound No. 1-10);
N-(2-Methoxybenzyl)-5-{[(4-methylphenyl)sulfonyl]oxy}naphthalene-1-sulfonamide (Compound No. 1-11);
N-(3-Methoxybenzyl)-5-{[(4-methylphenyl)sulfonyl]oxy}naphthalene-1-sulfonamide (Compound No. 1-12);
N-(2,3-Dimethoxybenzyl)-5-{[(4-methylphenyl)sulfonyl]oxy}naphthalene-1-sulfonamide (Compound No. 1-13);
N-(3,5-Dimethoxybenzyl)-5-{[(4-methylphenyl)sulfonyl]oxy}naphthalene-1-sulfonamide (Compound No. 1-14);
N-(3,4-Methylenedioxybenzyl)-5-{[(4-methylphenyl)sulfonyl]oxy}naphthalene-1-sulfonamide (Compound No. 1-15);
N-(3-Aminobenzyl)-5-{[(4-methylphenyl)sulfonyl]oxy}naphthalene-1-sulfonamide (Compound No. 1-16);
N-[4-(Dimethylamino)benzyl]-5-{[(4-methylphenyl)sulfonyl]oxy}naphthalene-1-sulfonamide (Compound No. 1-17);
N-[4-(Methanesulfonyl)benzyl]-5-{[(4-methylphenyl)sulfonyl]oxy}naphthalene-1-sulfonamide (Compound No. 1-18);
N-(1-Naphthylmethyl)-5-{[(4-methylphenyl)sulfonyl]oxy}naphthalene-1-sulfonamide (Compound No. 1-19);
N-[(5-Methylfuran-2-yl)methyl]-5-{[(4-methylphenyl)sulfonyl]oxy}naphthalene-1-sulfonamide (Compound No. 1-20);
N-[(Pyridin-2-yl)methyl]-5-{[(4-methylphenyl)sulfonyl]oxy}naphthalene-1-sulfonamide (Compound No. 1-21);
N-[(Benzimidazol-2-yl)methyl]-5-{[(4-methylphenyl)sulfonyl]oxy}naphthalene-1-sulfonamide (Compound No. 1-22);
N-Cyclohexylmethyl-5-{[(4-methylphenyl)sulfonyl]oxy}naphthalene-1-sulfonamide (Compound No. 1-23);
N-Phenyl-5-{[(4-methylphenyl)sulfonyl]oxy}naphthalene-1-sulfonamide (Compound No. 1-24);
N-(2-Phenethyl)-5-{[(4-methylphenyl)sulfonyl]oxy}naphthalene-1-sulfonamide (Compound No. 1-25);
N-(1-Phenethyl)-5-{[(4-methylphenyl)sulfonyl]oxy}naphthalene-1-sulfonamide (Compound No. 1-26);
N-Benzyl-N-methyl-5-{[(4-methylphenyl)sulfonyl]oxy}naphthalene-1-sulfonamide (Compound No. 1-27);
N-Benzyl-5-hydroxynaphthalene-1-sulfonamide (Compound No. 2-1);
N-(2,6-Difluorobenzyl)-5-hydroxynaphthalene-1-sulfonamide (Compound No. 2-2);
N-(2,4-Dichlorobenzyl)-5-hydroxynaphthalene-1-sulfonamide (Compound No. 2-3);

N-(3-Nitrobenzyl)-5-hydroxynaphthalene-1-sulfonamide (Compound No. 2-4);
N-(4-Nitrobenzyl)-5-hydroxynaphthalene-1-sulfonamide (Compound No. 2-5);
N-(2-Methylbenzyl)-5-hydroxynaphthalene-1-sulfonamide (Compound No. 2-6);
N-[4-(tert-Butyl)benzyl]-5-hydroxynaphthalene-i-sulfonamide (Compound No. 2-7);
N-[2-(Trifluoromethyl)benzyl]-5-hydroxynaphthalene-1-sulfonamide (Compound No. 2-8);
N-[4-(Trifluoromethyl)benzyl]-5-hydroxynaphthalene-1-sulfonamide (Compound No. 2-9);
N-(3,4-Dihydroxylbenzyl)-5-hydroxynaphthalene-1-sulfonamide (Compound No. 2-10);
N-(2-Methoxylbenzyl)-5-hydroxynaphthalene-1-sulfonamide (Compound No. 2-11);
N-(3-Methoxylbenzyl)-5-hydroxynaphthalene-1-sulfonamide (Compound No. 2-12);
N-(2,3-Dimethoxylbenzyl)-5-hydroxynaphthalene-1-sulfonamide (Compound No. 2-13);
N-(3,5-Dimethoxylbenzyl)-5-hydroxynaphthalene-1-sulfonamide (Compound No. 2-14);
N-(3,4-Methylenedioxylbenzyl)-5-hydroxynaphthalene-1-sulfonamide (Compound No. 2-15);
N-(3-Aminobenzyl)-5-hydroxynaphthalene-1-sulfonamide (Compound No. 2-16);
N-[4-(Dimethylamino)benzyl]-5-hydroxynaphthalene-1-sulfonamide (Compound No. 2-17);
N-[4-(Methanesulfonyl)benzyl]-5-hydroxynaphthalene-1-sulfonamide (Compound No. 2-18);
N-(1-Naphthylmethyl)-5-hydroxynaphthalene-1-sulfonamide (Compound No. 2-19);
N-[(5-Methylfuran-2-yl)methyl]-5-hydroxynaphthalene-1-sulfonamide (Compound No. 2-20);
N-[(Pyridin-2-yl)methyl]-5-hydroxynaphthalene-1-sulfonamide (Compound No. 2-21);
N-[(Benzimidazol-2-yl)methyl]-5-hydroxynaphthalene-1-sulfonamide (Compound No. 2-22);
N-Cyclohexylmethyl-5-hydroxynaphthalene-1-sulfonamide (Compound No. 2-23);
N-Phenyl-5-hydroxynaphthalene-1-sulfonamide (Compound No. 2-24);
N-(2-Phenethyl)-5-hydroxynaphthalene-1-sulfonamide (Compound No. 2-25);
N-(1-Phenethyl)-5-hydroxynaphthalene-1-sulfonamide (Compound No. 2-26);
N-Benzyl-N-methyl-5-hydroxynaphthalene-1-sulfonamide (Compound No. 2-27);
5-Acetyloxy-N-benzylnaphthalene-2-sulfonamide (Compound No. 3-1);
5-Acetyloxy-N-(2,4-dichlorobenzyl)naphthalene-2-sulfonamide (Compound No. 3-2);
5-Acetyloxy-N-(3-nitrobenzyl)naphthalene-2-sulfonamide (Compound No. 3-3);
5-Acetyloxy-N-[4-(tert-butyl)benzyl]naphthalene-2-sulfonamide (Compound No. 3-4);
5-Acetyloxy-N-[4-(trifluoromethyl)benzyl]naphthalene-2-sulfonamide (Compound No. 3-5);
5-Acetyloxy-N-(2,3-dimethoxybenzyl)naphthalene-2-sulfonamide (Compound No. 3-6);
5-Acetyloxy-N-(3-aminobenzyl)naphthalene-2-sulfonamide (Compound No. 3-7);
5-Acetyloxy-N-(1-naphthylmethyl)naphthalene-2-sulfonamide (Compound No. 3-8);
5-Acetyloxy-N-[(5-methylfuran-2-yl)methyl]naphthalene-2-sulfonamide (Compound No. 3-9);
5-Acetyloxy-N-[(pyridin-2-yl)methyl]naphthalene-2-sulfonamide (Compound No. 3-10);
5-Acetyloxy-N-(cyclohexylmethyl)naphthalene-2-sulfonamide (Compound No. 3-11);
5-Acetyloxy-N-phenylnaphthalene-2-sulfonamide (Compound No. 3-12);
5-Acetyloxy-N-(2-phenethyl)naphthalene-2-sulfonamide (Compound No. 3-13);
5-Acetyloxy-N-(1-phenethyl)naphthalene-2-sulfonamide (Compound No. 3-14);
5-Acetyloxy-N-benzyl-N-methylnaphthalene-2-sulfonamide (Compound No. 3-15);
N-Benzyl-5-hydroxynaphthalene-2-sulfonamide (Compound No. 4-1);
N-(2,4-Dichlorobenzyl)-5-hydroxynaphthalene-2-sulfonamide (Compound No. 4-2);
N-(3-Nitrobenzyl)-5-hydroxynaphthalene-2-sulfonamide (Compound No. 4-3);
N-[4-(tert-Butyl)benzyl]-5-hydroxynaphthalene-2-sulfonamide (Compound No. 4-4);
N-[4-(Trifluoromethyl)benzyl]-5-hydroxynaphthalene-2-sulfonamide (Compound No. 4-5);
N-(2,3-Dimethoxybenzyl)-5-hydroxynaphthalene-2-sulfonamide (Compound No. 4-6);
N-(3-Aminobenzyl)-5-hydroxynaphthalene-2-sulfonamide (Compound No. 4-7);
N-(1-Naphthylmethyl)-5-hydroxynaphthalene-2-sulfonamide (Compound No. 4-8);
N-[(5-Methylfuran-2-yl)methyl]-5-hydroxynaphthalene-2-sulfonamide (Compound No. 4-9);
N-[(Pyridin-2-yl)methyl]-5-hydroxynaphthalene-2-sulfonamide (Compound No. 4-10);
N-(Cyclohexylmethyl)-5-hydroxynaphthalene-2-sulfonamide (Compound No. 4-11);
N-Phenyl-5-hydroxynaphthalene-2-sulfonamide (Compound No. 4-12);
N-(2-Phenethyl)-5-hydroxynaphthalene-2-sulfonamide (Compound No. 4-13);
N-(1-Phenethyl)-5-hydroxynaphthalene-2-sulfonamide (Compound No. 4-14);
N-Benzyl-N-methyl-5-hydroxynaphthalene-2-sulfonamide (Compound No. 4-15);
5-Acetylamino-N-benzylnaphthalene-2-sulfonamide (Compound No. 5-1);
5-Acetylamino-N-[4-(tert-butyl)benzyl]naphthalene-2-sulfonamide (Compound No. 5-2);
5-Acetylamino-N-(2,3-dimethoxybenzyl)naphthalene-2-sulfonamide (Compound No. 5-3);
5-Acetylamino-N-benzyl-N-methylnaphthalene-2-sulfonamide (Compound No. 5-4);
5-Amino-N-benzylnaphthalene-2-sulfonamide (Compound No. 6-1; This compound is represented as a hydrochloride in the following examples.);
5-Amino-N-[4-(tert-butyl)benzyl]naphthalene-2-sulfonamide (Compound No. 6-2; This compound is represented as a hydrochloride in the following examples.);
5-Amino-N-(2,3-dimethoxybenzyl)naphthalene-2-sulfonamide (Compound No. 6-3; This compound is represented as a hydrochloride in the following examples.);
5-Amino-N-benzyl-N-methylnaphthalene-2-sulfonamide (Compound No. 6-4; This compound is represented as a hydrochloride in the following examples.);
6-Acetylamino-N-benzylnaphthalene-1-sulfonamide (Compound No. 7-1);
6-Acetylamino-N-[4-(tert-butyl)benzyl]naphthalene-1-sulfonamide (Compound No. 7-2);

6-Acetylamino-N-(2,3-dimethoxybenzyl)naphthalene-1-sulfonamide (Compound No. 7-3);
6-Amino-N-benzylnaphthalene-1-sulfonamide (Compound No. 8-1; This compound is represented as a hydrochloride in the following examples.);
6-Amino-N-[4-(tert-butyl)benzyl]naphthalene-1-sulfonamide (Compound No. 8-2; This compound is represented as a hydrochloride in the following examples.);
6-Amino-N-(2,3-dimethoxybenzyl)naphthalene-1-sulfonamide (Compound No. 8-3; This compound is represented as a hydrochloride in the following examples.);
6-Acetylamino-N-benzylnaphthalene-2-sulfonamide (Compound No. 9-1);
6-Acetylamino-N-[4-(tert-butyl)benzyl]naphthalene-2-sulfonamide (Compound No. 9-2);
6-Acetylamino-N-(2,3-dimethoxybenzyl)naphthalene-2-sulfonamide (Compound No. 9-3);
6-Amino-N-benzylnaphthalene-2-sulfonamide (Compound No. 10-1; This compound is represented as a hydrochloride in the following examples.);
6-Amino-N-[4-(tert-butyl)benzyl]naphthalene-2-sulfonamide (Compound No. 10-2; This compound is represented as a hydrochloride in the following examples.);
6-Amino-N-(2,3-dimethoxybenzyl)naphthalene-2-sulfonamide (Compound No. 10-3; This compound is represented as a hydrochloride in the following examples.);
5-Amino-N-benzylnaphthalene-1-carboxamide (Compound No. 11-1);
5-Amino-N-[4-(tert-butyl)benzyl]naphthalene-1-carboxamide (Compound No. 11-2);
5-Amino-N-(2,3-dimethoxybenzyl)naphthalene-1-carboxamide (Compound No. 11-3).

The compounds represented by the general formula (I) may form salts. Kinds of salts are not particularly limited. When acidic groups exist, examples include metal salts such as lithium salt, sodium salt, potassium salt, magnesium salt, and calcium salt; or ammonium salts such as ammonium salt, methylammonium salt, dimethylammonium salt, trimethylammonium salt, and dicyclohexylammonium salt, and when basic groups exist, examples include mineral acid salts such as hydrochloride, hydrobromide, sulfate, nitrate, and phosphate, or organic acid salts such as methane sulfonate, benzene sulfonate, para-toluene sulfonate, acetate, propionate, tartrate, fumarate, maleate, malate, oxalate, succinate, citrate, benzoate, mandelate, cinnamate, and lactate. Salts may sometimes be formed with amino acids such as glycine. As active ingredients of the medicaments of the present invention, pharmacologically acceptable salts are suitable.

The compounds or salts thereof represented by the general formula (I) may exist as hydrates or solvates. Furthermore, the compounds represented by the general formula (I) may sometimes have one or more asymmetric carbons, and may exist as stereoisomers such as optically active isomers and diastereomers. As active ingredients of the medicaments of the present invention, a pure form of a stereoisomer, any mixture of enantiomers or diastereomers, a racemate or the like may be used.

Furthermore, when the compounds represented by the general formula (I) have an olefinic double bond, its configuration may be in either E or Z. As an active ingredient of the medicament of the present invention, a geometrical isomer in either of the configurations or a mixture thereof may be used.

Examples of the compounds encompassed within the general formula (I), which are for active ingredients of the medicaments of the present invention, are shown below. However, the active ingredients of the medicaments of the present invention are not limited to the following compounds.

The abbreviations used in the following tables have the following meanings.

Me: methyl group.

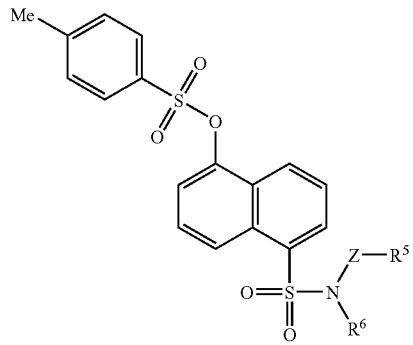

| Compound Number | Z | $R^5$ | $R^6$ |
|---|---|---|---|
| 1-1 | —$CH_2$— | phenyl | H |
| 1-2 | —$CH_2$— | 2,6-difluorophenyl | H |
| 1-3 | —$CH_2$— | 2,4-dichiorophenyl | H |
| 1-4 | —$CH_2$— | 3-nitrophenyl | H |
| 1-5 | —$CH_2$— | 4-nitrophenyl | H |
| 1-6 | —$CH_2$— | 2-methylphenyl | H |
| 1-7 | —$CH_2$— | 4-(tert-butyl)phenyl | H |
| 1-8 | —$CH_2$— | 2-(trifluoromethyl)phenyl | H |
| 1-9 | —$CH_2$— | 4-(trifluoromethyl)phenyl | H |
| 1-10 | —$CH_2$— | 3,4-dihydroxyphenyl | H |
| 1-11 | —$CH_2$— | 2-methoxyphenyl | H |
| 1-12 | —$CH_2$— | 3-methoxyphenyl | H |
| 1-13 | —$CH_2$— | 2,3-dimethoxyphenyl | H |
| 1-14 | —$CH_2$— | 3,5-dimethoxyphenyl | H |
| 1-15 | —$CH_2$— | 3,4-methylenedioxyphenyl | H |
| 1-16 | —$CH_2$— | 3-aminophenyl | H |
| 1-17 | —$CH_2$— | 4-(dimethylamino)phenyl | H |
| 1-18 | —$CH_2$— | 4-methanesulfonylphenyl | H |
| 1-19 | —$CH_2$— | 1-naphthyl | H |
| 1-20 | —$CH_2$— | 5-methylfuran-2-yl | H |
| 1-21 | —$CH_2$— | Pyridin-2-yl | H |
| 1-22 | —$CH_2$— | Benzimidazol-2-yl | H |
| 1-23 | —$CH_2$— | cyclohexyl | H |
| 1-24 | single bond | phenyl | H |
| 1-25 | —$CH_2CH_2$— | phenyl | H |
| 1-26 | —$CH(CH_3)$— | phenyl | H |
| 1-27 | —$CH_2$— | phenyl | Me |

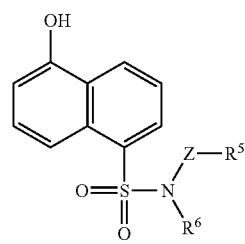

| Compound Number | Z | $R^5$ | $R^6$ |
|---|---|---|---|
| 2-1 | —$CH_2$— | phenyl | H |
| 2-2 | —$CH_2$— | 2,6-difluorophenyl | H |
| 2-3 | —$CH_2$— | 2,4-dichlorophenyl | H |
| 2-4 | —$CH_2$— | 3-nitrophenyl | H |
| 2-5 | —$CH_2$— | 4-nitrophenyl | H |
| 2-6 | —$CH_2$— | 2-methyiphenyl | H |
| 2-7 | —$CH_2$— | 4-(tert-butyl)phenyl | H |

-continued

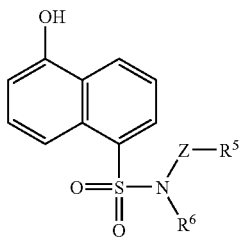

| Compound Number | Z | R⁵ | R⁶ |
|---|---|---|---|
| 2-8 | —CH₂— | 2-(trifluoromethyl)phenyl | H |
| 2-9 | —CH₂— | 4-(trifluoromethyl)phenyl | H |
| 2-10 | —CH₂— | 3,4-dihydroxyphenyl | H |
| 2-11 | —CH₂— | 2-methoxyphenyl | H |
| 2-12 | —CH₂— | 3-methoxyphenyl | H |
| 2-13 | —CH₂— | 2,3-dimethoxyphenyl | H |
| 2-14 | —CH₂— | 3,5-dimethoxyphenyl | H |
| 2-15 | —CH₂— | 3,4-methylenedioxyphenyl | H |
| 2-16 | —CH₂— | 3-aminophenyl | H |
| 2-17 | —CH₂— | 4-(dimethylamino)phenyl | H |
| 2-18 | —CH₂— | 4-methanesulfonylphenyl | H |
| 2-19 | —CH₂— | 1-naphthyl | H |
| 2-20 | —CH₂— | 5-methylfuran-2-yl | H |
| 2-21 | —CH₂— | Pyridin-2-yl | H |
| 2-22 | —CH₂— | Benzimidazol-2-yl | H |
| 2-23 | —CH₂— | cyclohexyl | H |
| 2-24 | single bond | phenyl | H |
| 2-25 | —CH₂CH₂— | phenyl | H |
| 2-26 | —CH(CH₃)— | phenyl | H |
| 2-27 | —CH₂— | phenyl | Me |

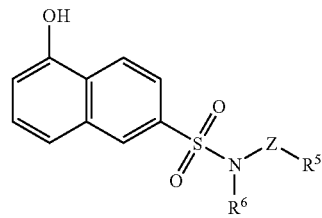

| Compound Number | Z | R⁵ | R⁶ |
|---|---|---|---|
| 4-1 | —CH₂— | phenyl | H |
| 4-2 | —CH₂— | 2,4-dichlorophenyl | H |
| 4-3 | —CH₂— | 3-nitrophenyl | H |
| 4-4 | —CH₂— | 4-(tert-butyl)phenyl | H |
| 4-5 | —CH₂— | 4-(trifluoromethyl)phenyl | H |
| 4-6 | —CH₂— | 2,3-dimethoxyphenyl | H |
| 4-7 | —CH₂— | 3-aminophenyl | H |
| 4-8 | —CH₂— | 1-naphthyl | H |
| 4-9 | —CH₂— | 5-methylfuran-2-yl | H |
| 4-10 | —CH₂— | Pyridin-2-yl | H |
| 4-11 | —CH₂— | cyclohexyl | H |
| 4-12 | single bond | phenyl | H |
| 4-13 | —CH₂CH₂— | phenyl | H |
| 4-14 | —CH(CH₃)— | phenyl | H |
| 4-15 | —CH₂— | phenyl | Me |

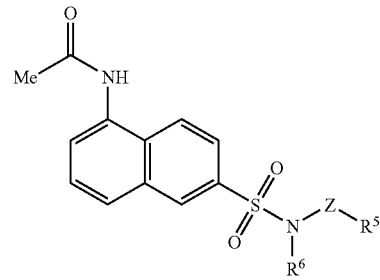

| Compound Number | Z | R⁵ | R⁶ |
|---|---|---|---|
| 5-1 | —CH₂— | phenyl | H |
| 5-2 | —CH₂— | 4-(tert-butyl)phenyl | H |
| 5-3 | —CH₂— | 2,3-dimethoxyphenyl | H |
| 5-4 | —CH₂— | phenyl | Me |

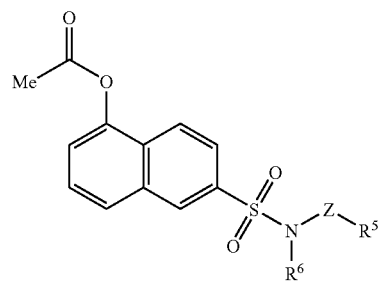

| Compound Number | Z | R⁵ | R⁶ |
|---|---|---|---|
| 3-1 | —CH₂— | phenyl | H |
| 3-2 | —CH₂— | 2,4-dichlorophenyl | H |
| 3-3 | —CH₂— | 3-nitrophenyl | H |
| 3-4 | —CH₂— | 4-(tert-butyl)phenyl | H |
| 3-5 | —CH₂— | 4-(trifluoromethyl)phenyl | H |
| 3-6 | —CH₂— | 2,3-dimethoxyphenyl | H |
| 3-7 | —CH₂— | 3-aminophenyl | H |
| 3-8 | —CH₂— | 1-naphthyl | H |
| 3-9 | —CH₂— | 5-methylfuran-2-yl | H |
| 3-10 | —CH₂— | Pyridin-2-yl | H |
| 3-11 | —CH₂— | cyclohexyl | H |
| 3-12 | single bond | phenyl | H |
| 3-13 | —CH₂CH₂— | phenyl | H |
| 3-14 | —CH(CH₃)— | phenyl | H |
| 3-15 | —CH₂— | phenyl | Me |

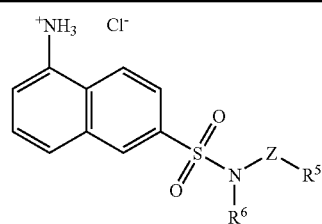

| Compound Number | Z | R⁵ | R⁶ |
|---|---|---|---|
| 6-1 | —CH₂— | phenyl | H |
| 6-2 | —CH₂— | 4-(tert-butyl)phenyl | H |
| 6-3 | —CH₂— | 2,3-dimethoxyphenyl | H |
| 6-4 | —CH₂— | phenyl | Me |

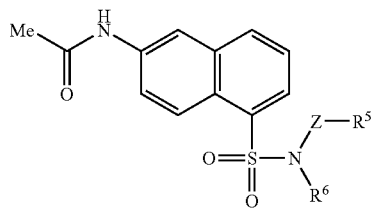

| Compound Number | Z | $R^5$ | $R^6$ |
|---|---|---|---|
| 7-1 | —CH$_2$— | phenyl | H |
| 7-2 | —CH$_2$— | 4-(tert-butyl)phenyl | H |
| 7-3 | —CH$_2$— | 2,3-dimethoxyphenyl | H |

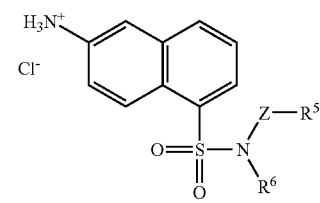

| Compound Number | Z | $R^5$ | $R^6$ |
|---|---|---|---|
| 8-1 | —CH$_2$— | phenyl | H |
| 8-2 | —CH$_2$— | 4-(tert-butyl)phenyl | H |
| 8-3 | —CH$_2$— | 2,3-dimethoxyphenyl | H |

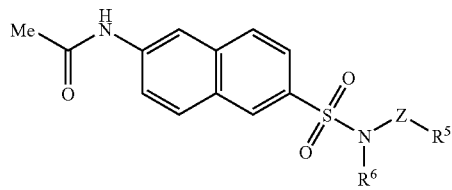

| Compound Number | Z | $R^5$ | $R^6$ |
|---|---|---|---|
| 9-1 | —CH$_2$— | phenyl | H |
| 9-2 | —CH$_2$— | 4-(tert-butyl)phenyl | H |
| 9-3 | —CH$_2$— | 2,3-dimethoxyphenyl | H |

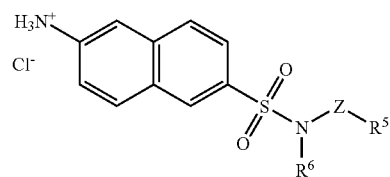

| Compound Number | Z | $R^5$ | $R^6$ |
|---|---|---|---|
| 10-1 | —CH$_2$— | phenyl | H |
| 10-2 | —CH$_2$— | 4-(tert-butyl)phenyl | H |
| 10-3 | —CH$_2$— | 2,3-dimethoxyphenyl | H |

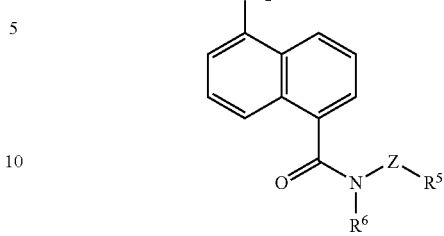

| Compound Number | Z | $R^5$ | $R^6$ |
|---|---|---|---|
| 11-1 | —CH$_2$— | phenyl | H |
| 11-2 | —CH$_2$— | 4-(tert-butyl)phenyl | H |
| 11-3 | —CH$_2$— | 2,3-dimethoxyphenyl | H |

The compounds represented by the general formula (I) of the present invention can be prepared, for example, by methods shown below.

<<Preparation Method 1>>

In the compounds represented by the general formula (I) of the present invention, the compounds wherein $R^1$ is a group represented by the formula —O-A wherein A represents hydrogen atom or an acyl group, $R^2$ is hydrogen atom, $R^3$ is a group represented by the following formula:

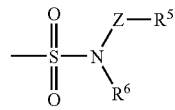

wherein $R^5$ represents a cyclic group which may be substituted, Z represents a single bond or a $C_1$ to $C_4$ alkylene group which may be substituted; or when Z is substituted, said substituent may bind to $R^5$ to form a cyclic group, $R^6$ represents hydrogen atom or a $C_1$ to $C_6$ alkyl group which may be substituted; or $R^6$ may bind to Z or $R^5$ to form a cyclic group, $R^4$ is hydrogen atom can be prepared, for example, by a method described in the reaction scheme 1.

<Reaction Scheme 1>

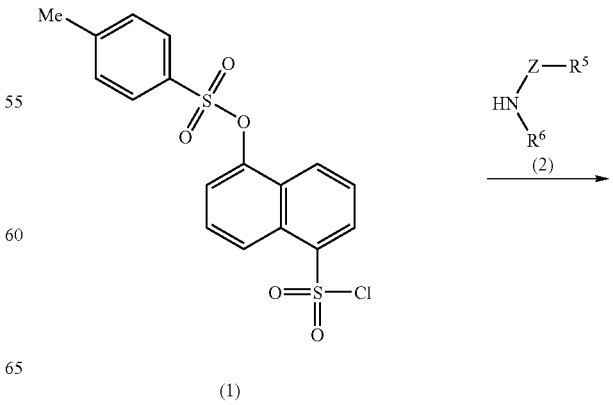

-continued

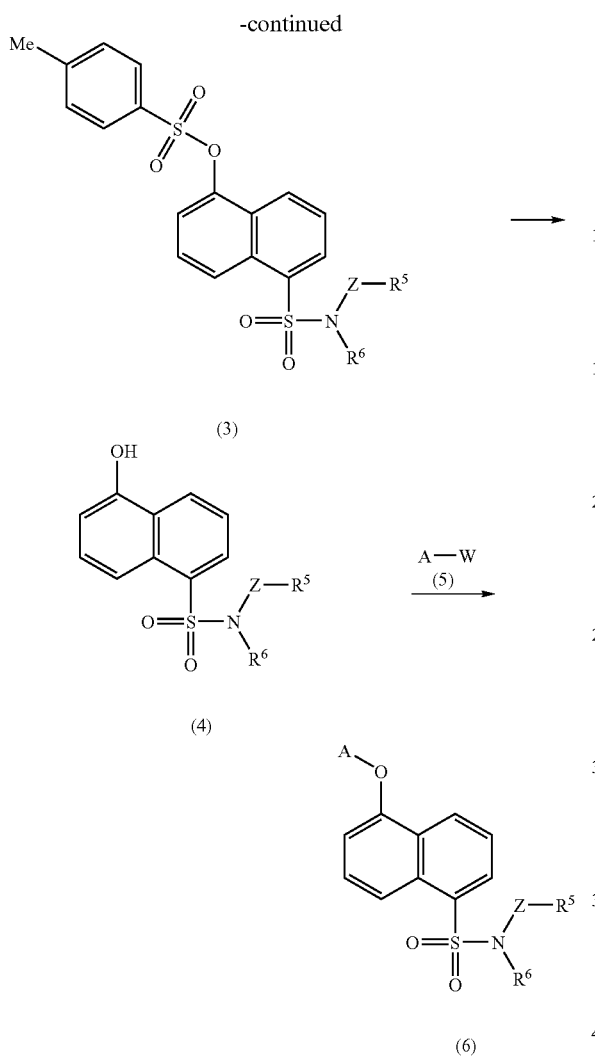

5-{[(4-Methylphenyl)sulfonyl]oxy}naphthalene-1-sulfonyl chloride (1) can be prepared, for example, by the method disclosed in the U.S. Pat. No. 5,378,715. As for the amine (2) wherein $R^5$, $R^6$, and Z have the same meanings as those defined in the general formula (I), most of the amines in the free form or acid addition salts are widely available in the market, and commercial products can be obtained and directly used. Furthermore, the amine (2) wherein $R^5$, $R^6$, and Z have the same meanings as those defined in the general formula (I) can also prepared by methods readily understandable by those skilled in the art (for example, reduction of a corresponding nitro compound, reduction of a cyano compound, reduction of a carbamoyl compound and the like), and it is also understandable that the resulting amine can be used for preparation of the compounds of the present invention.

By reacting 5-{[(4-methylphenyl)sulfonyl]oxy}naphthalene-1-sulfonyl chloride (1) with the amine (2) wherein $R^5$, $R^6$, and Z have the same meanings as those defined in the general formula (I), the compound of the formula (3) wherein $R^5$, $R^6$, and Z have the same meanings as those defined in the general formula (I) can be obtained. The compound of the formula (3) is encompassed within the general formula (I). This reaction is carried out in the presence or absence of a base and/or a catalyst, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the catalysts include 4-dimethylaminopyridine and tetrabutylammonium bromide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

The tosyl group of the resulting compound of the formula (3) wherein $R^5$, $R^6$, and Z have the same meanings as those defined in the general formula (I) is then hydrolyzed to prepare the compounds represented by the formula (4). The compound of the formula (4) is encompassed within the general formula (I). This reaction is carried out in the presence of an acid or a base, with or without a solvent, at a reaction temperature of from 0° C. to a refluxing temperature of a solvent (at a reaction temperature of from 0° C. to 150° C., when the reaction is carried out without a solvent).

Examples of the acids include mineral acids such as hydrochloric acid and sulfuric acid; organic acids such as formic acid, acetic acid, methanesulfonic acid, and p-toluenesulfonic acid; and Lewis acids such as alminium chloride and triethyloxonium tetrafluoroborate. Examples of the bases include inorganic bases such as sodium hydroxide, potassium hydroxide, potassium carbonate, and sodium hydrogencarbonate; and organic bases such as hydrazine. Any solvent can be used as long as it does not inhibit the reaction, and examples include ethers such as tetrahydrofuran, 1,2-dimethoxyethane, and 1,4-dioxane; alcohols such as methanol, ethanol, 1-propanol, and 2-propanol; and water. These solvents can be used alone or as a mixture, or as two phase solvents.

The compound of the formula (4) wherein $R^5$, $R^6$, and Z have the same meanings as those defined in the general formula (I) is then reacted with the acylating agent (5) wherein A represents an acyl group, W represents halogen atom; acyloxy group such as acetoxy group, benzoyloxy group, methanesulfonyl group, and tosyl group; imidoxy group such as (2,5-dioxopyrrolidin-1-yl group; 1-imidazolyl group; and hydroxy group, to prepare the compounds represented by the formula (6), which are encompassed within the general formula (I), wherein A, $R^5$, $R^6$, and Z have the same meanings as those defined in the general formula (I). This reaction is carried out in the presence or absence of a base and/or an adjuvant for acylation, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the adjuvants for acylation include catalysts such as 4-dimethylaminopyridine and tetrabutylammonium bromide; halogenating agents such as thionyl chloride, phosphorus oxychloride, phosphorus trichloride, ethyl chloroformate, and 4-nitrobenzenesulfonyl chloride; carbodiimides such as N,N'-dicyclohexyl-carbodiimide and 1-[3-(dimethylamino)propyl]-3-ethylcarbodiimide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

<<Preparation Method 2>>

In the compounds represented by the general formula (I) of the present invention, the compounds wherein $R^1$ is a group represented by the formula —O-A wherein A represents hydrogen atom or an acyl group, $R^2$ is hydrogen atom, $R^3$ is hydrogen atom, $R^4$ is a group represented by the following formula:

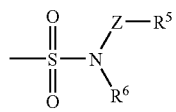

wherein $R^5$ represents a cyclic group which may be substituted, Z represents a single bond or a $C_1$ to $C_4$ alkylene group which may be substituted; or when Z is substituted, said substituent may bind to $R^5$ to form a ring group, $R^6$ represents hydrogen atom or a $C_1$ to $C_6$ alkyl group which may be substituted; or $R^6$ may bind to Z or $R^5$ to form a ring group can be prepared, for example, by a method described in the reaction scheme 2.

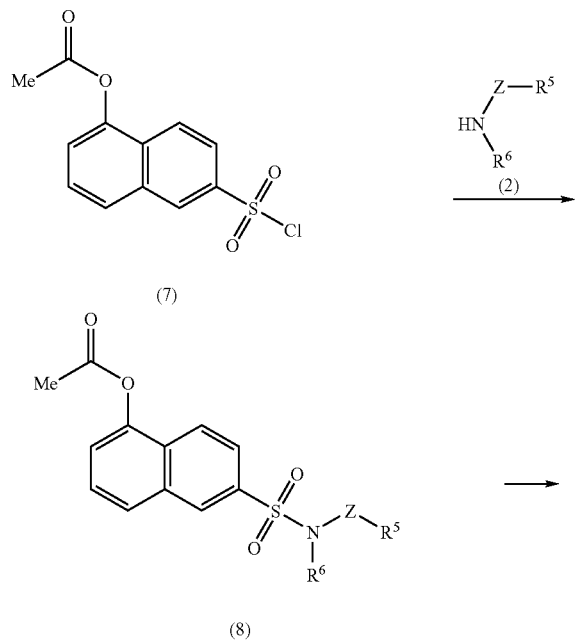

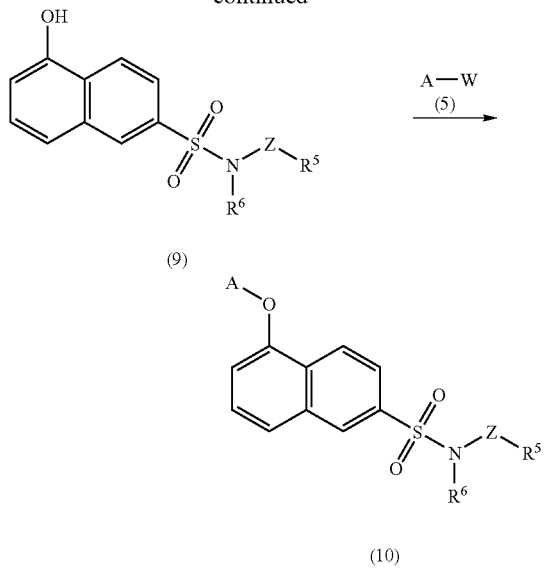

5-(Acetyloxy)naphthalene-2-sulfonyl chloride (7) can be prepared, for example, by the method disclosed in Tetrahedron, volume 48, No. 42, pp. 9207-9216(published in 1992) and Japanese Patent Kokoku Sho 60-140240. The amine (2) wherein $R^5$, $R^6$, and Z have the same meanings as those defined in the general formula (I) can be obtained by methods described in the preparation method 1.

By reacting 5-(acetyloxy)naphthalene-2-sulfonyl chloride (7) with the amine (2) wherein $R^5$, $R^6$, and Z have the same meanings as those defined in the general formula (I), the compound of the formula (8) wherein $R^5$, $R^6$, and Z have the same meanings as those defined in the general formula (I) can be obtained. The compound of the formula (8) is encompassed within the general formula (I). This reaction is carried out in the presence or absence of a base and/or a catalyst, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the catalysts include 4-dimethylaminopyridine and tetrabutylammonium bromide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

The acetyl group of the resulting compound of the formula (8) wherein $R^5$, $R^6$, and Z have the same meanings as those defined in the general formula (I) is then hydrolyzed to prepare the compounds represented by the formula (9). The compound of the formula (9) is encompassed within the general formula (I). This reaction is carried out in the presence of an acid or a base, with or without a solvent, at a reaction temperature of from 0° C. to a refluxing temperature of a solvent (at a reaction temperature of from 0° C. to 150° C., when the reaction is carried out without a solvent).

Examples of the acids include mineral acids such as hydrochloric acid and sulfuric acid; organic acids such as formic acid, acetic acid, methanesulfonic acid, and p-toluenesulfonic acid; and Lewis acids such as alminium chloride and triethyloxonium tetrafluoroborate. Examples of the bases include inorganic bases such as sodium hydroxide, potassium hydroxide, potassium carbonate, and sodium hydrogencarbonate; and organic bases such as hydrazine. Any solvent can be used as long as it does not inhibit the reaction, and examples include ethers such as tetrahydrofuran, 1,2-dimethoxyethane, and 1,4-dioxane; alcohols such as methanol, ethanol, 1-propanol, and 2-propanol; and water. These solvents can be used alone or as a mixture, or as two phase solvents.

The compound of the formula (9) wherein $R^5$, $R^6$, and Z have the same meanings as those defined in the general formula (I) is then reacted with the acylating agent (5) wherein A represents an acyl group, W represents halogen atom; acyloxy group such as acetoxy group, benzoyloxy group, methanesulfonyl group, and tosyl group; imidoxy group such as (2,5-dioxopyrrolidin-1-yl group; 1-imidazolyl group; and hydroxy group, to prepare the compounds represented by the formula (10), which are encompassed within the general formula (I), wherein A, $R^5$, $R^6$, and Z have the same meanings as those defined in the general formula (I). This reaction is carried out in the presence or absence of a base and/or an adjuvant for acylation, with or without a solvent, at a reaction temperature of from –30° C. to a refluxing temperature of a solvent (at a reaction temperature of from –30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the adjuvants for acylation include catalysts such as 4-dimethylaminopyridine and tetrabutylammonium bromide; halogenating agents such as thionyl chloride, phosphorus oxychloride, phosphorus trichloride, ethyl chloroformate, and 4-nitrobenzenesulfonyl chloride; carbodiimides such as N,N'-dicyclohexylcarbodiimide and 1-[3-(dimethylamino)propyl]-3-ethylcarbodiimide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

<<Preparation Method 3>>

In the compounds represented by the general formula (I) of the present invention, the compounds wherein $R^1$ is a group represented by the formula —NH-A wherein A represents hydrogen atom or an acyl group, $R^2$ is hydrogen atom, $R^3$ is hydrogen atom, $R^4$ is a group represented by the following formula:

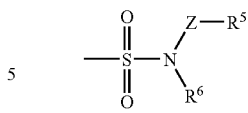

wherein $R^5$ represents a cyclic group which may be substituted, Z represents a single bond or a $C_1$ to $C_4$ alkylene group which may be substituted; or when Z is substituted, said substituent may bind to $R^5$ to form a ring group, $R^6$ represents hydrogen atom or a $C_1$ to $C_6$ alkyl group which may be substituted; or $R^6$ may bind to Z or $R^5$ to form a ring group can be prepared, for example, by a method described in the reaction scheme 3.

<Reaction Scheme 3>

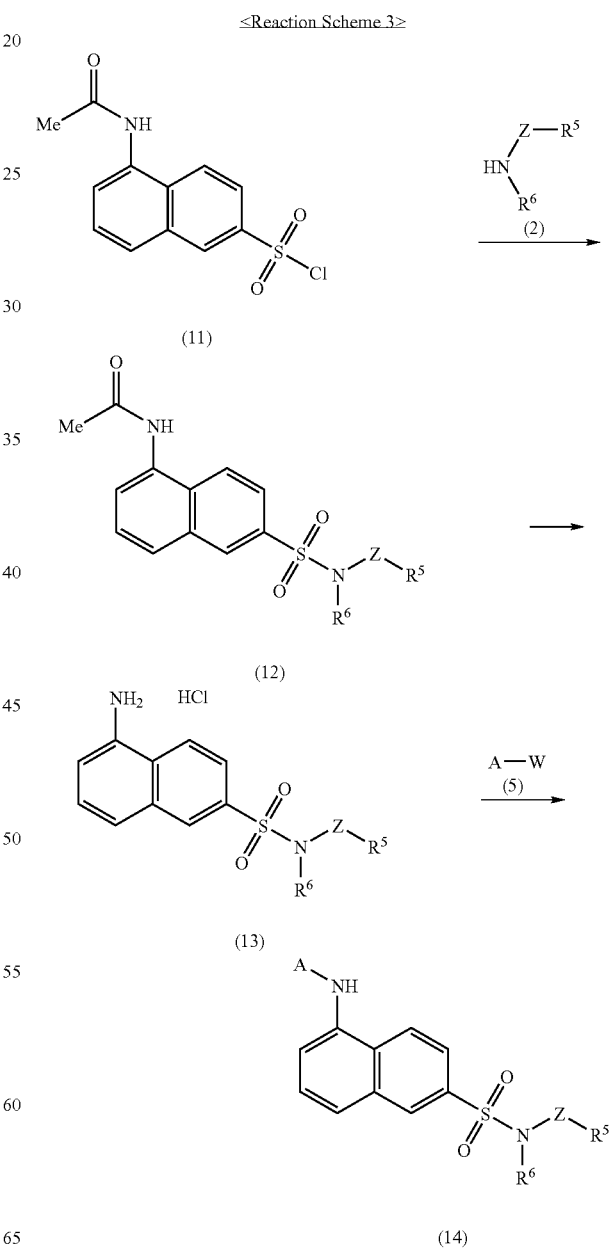

5-(Acetylamino)naphthalene-2-sulfonyl chloride (11) can be prepared, for example, by the method disclosed in the U.S. Pat. No. 5,378,715. The amine (2) wherein $R^5$, $R^6$, and Z have the same meanings as those defined in the general formula (I) can be obtained by methods described in the preparation method 1.

By reacting 5-(acetylamino)naphthalene-2-sulfonyl chloride (11) with the amine (2) wherein $R^5$, $R^6$, and Z have the same meanings as those defined in the general formula (I), the compound of the formula (12) wherein $R^5$, $R^6$, and Z have the same meanings as those defined in the general formula (I) can be obtained. The compound of the formula (12) is encompassed within the general formula (I). This reaction is carried out in the presence or absence of a base and/or a catalyst, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the catalysts include 4-dimethylaminopyridine and tetrabutylammonium bromide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

The acetyl group of the resulting compound of the formula (12) wherein $R^5$, $R^6$, and Z have the same meanings as those defined in the general formula (I) is then hydrolyzed to prepare the compounds represented by the formula (13). The compound of the formula (13) is encompassed within the general formula (I). This reaction is carried out in the presence of an acid or a base, with or without a solvent, at a reaction temperature of from 0° C. to a refluxing temperature of a solvent (at a reaction temperature of from 0° C. to 150° C., when the reaction is carried out without a solvent).

Examples of the acids include mineral acids such as hydrochloric acid and sulfuric acid; and Lewis acids such as triethyloxonium tetrafluoroborate. Examples of the bases include inorganic bases such as sodium hydroxide, potassium hydroxide, and metallic sodium; and organic bases such as hydrazine. Any solvent can be used as long as it does not inhibit the reaction, and examples include ethers such as tetrahydrofuran, 1,2-dimethoxyethane, and 1,4-dioxane; alcohols such as methanol, ethanol, 1-propanol, and 2-propanol; and water. These solvents can be used alone or as a mixture, or as two phase solvents.

The compound of the formula (13) wherein $R^5$, $R^6$, and Z have the same meanings as those defined in the general formula (I) is then reacted with the acylating agent (5) wherein A represents an acyl group, W represents halogen atom; acyloxy group such as acetoxy group, benzoyloxy group, methanesulfonyl group, and tosyl group; imidoxy group such as (2,5-dioxopyrrolidin-1-yl group; 1-imidazolyl group; and hydroxy group, to prepare the compounds represented by the formula (14), which are encompassed within the general formula (I), wherein A, $R^5$, $R^6$, and Z have the same meanings as those defined in the general formula (I). This reaction is carried out in the presence or absence of a base and/or an adjuvant for acylation, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the adjuvants for acylation include catalysts such as 4-dimethylaminopyridine and tetrabutylammonium bromide; halogenating agents such as thionyl chloride, phosphorus oxychloride, phosphorus trichloride, ethyl chloroformate, and 4-nitrobenzenesulfonyl chloride; carbodiimides such as N,N'-dicyclohexylcarbodiimide and 1-[3-(dimethylamino)propyl]-3-ethylcarbodiimide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

<<Preparation Method 4>>

In the compounds represented by the general formula (I) of the present invention, the compounds wherein $R^1$ is hydrogen atom, $R^2$ is a group represented by the formula —NH-A wherein A represents hydrogen atom or an acyl group, $R^3$ is a group represented by the following formula:

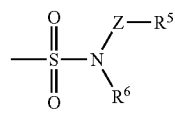

wherein $R^5$ represents a cyclic group which may be substituted, Z represents a single bond or a $C_1$ to $C_4$ alkylene group which may be substituted; or when Z is substituted, said substituent may bind to $R^5$ to form a ring group, $R^6$ represents hydrogen atom or a $C_1$ to $C_6$ alkyl group which may be substituted; or $R^6$ may bind to Z or $R^5$ to form a ring group, $R^4$ is hydrogen atom can be prepared, for example, by a method described in the reaction scheme 4.

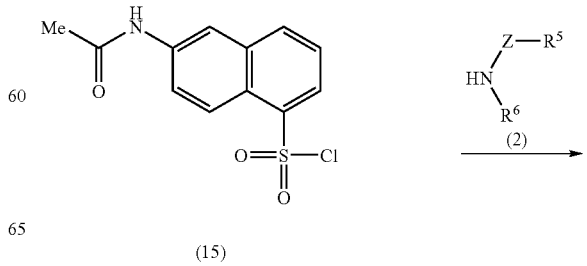

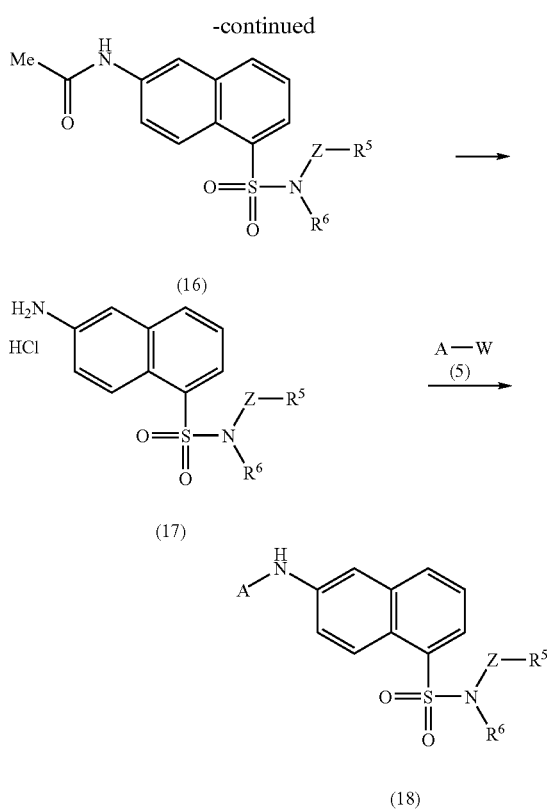

6-(Acetylamino)naphthalene-1-sulfonyl chloride (15) can be prepared, for example, by the method disclosed in the U.S. Pat. No. 5,378,715. The amine (2) wherein $R^5$, $R^6$, and Z have the same meanings as those defined in the general formula (I) can be obtained by methods described in the preparation method 1.

By reacting 6-(acetylamino)naphthalene-1-sulfonyl chloride (15) with the amine (2) wherein $R^5$, $R^6$, and Z have the same meanings as those defined in the general formula (I), the compound of the formula (16) wherein $R^5$, $R^6$, and Z have the same meanings as those defined in the general formula (I) can be obtained. The compound of the formula (16) is encompassed within the general formula (I). This reaction is carried out in the presence or absence of a base and/or a catalyst, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the catalysts include 4-dimethylaminopyridine and tetrabutylammonium bromide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

The acetyl group of the resulting compound of the formula (16) wherein $R^5$, $R^6$, and Z have the same meanings as those defined in the general formula (I) is then hydrolyzed to prepare the compounds represented by the formula (17). The compound of the formula (17) is encompassed within the general formula (I). This reaction is carried out in the presence of an acid or a base, with or without a solvent, at a reaction temperature of from 0° C. to a refluxing temperature of a solvent (at a reaction temperature of from 0° C. to 150° C., when the reaction is carried out without a solvent).

Examples of the acids include mineral acids such as hydrochloric acid and sulfuric acid; and Lewis acids such as triethyloxonium tetrafluoroborate. Examples of the bases include inorganic bases such as sodium hydroxide, potassium hydroxide, and metallic sodium; and organic bases such as hydrazine. Any solvent can be used as long as it does not inhibit the reaction, and examples include ethers such as tetrahydrofuran, 1,2-dimethoxyethane, and 1,4-dioxane; alcohols such as methanol, ethanol, 1-propanol, and 2-propanol; and water. These solvents can be used alone or as a mixture, or as two phase solvents.

The compound of the formula (17) wherein $R^5$, $R^6$, and Z have the same meanings as those defined in the general formula (I) is then reacted with the acylating agent (5) wherein A represents an acyl group, W represents halogen atom; acyloxy group such as acetoxy group, benzoyloxy group, methanesulfonyl group, and tosyl group; imidoxy group such as (2,5-dioxopyrrolidin-1-yl group; 1-imidazolyl group; and hydroxy group, to prepare the compounds represented by the formula (18), which are encompassed within the general formula (I), wherein A, $R^5$, $R^6$, and Z have the same meanings as those defined in the general formula (I). This reaction is carried out in the presence or absence of a base and/or an adjuvant for acylation, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the adjuvants for acylation include catalysts such as 4-dimethylaminopyridine and tetrabutylammonium bromide; halogenating agents such as thionyl chloride, phosphorus oxychloride, phosphorus trichloride, ethyl chloroformate, and 4-nitrobenzenesulfonyl chloride; carbodiimides such as N,N'-dicyclohexylcarbodiimide and 1-[3-(dimethylamino)propyl]-3-ethylcarbodiimide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

<<Preparation Method 5>>

In the compounds represented by the general formula (I) of the present invention, the compounds wherein $R^1$ is hydrogen atom, $R^2$ is a group represented by the formula —NH-A wherein A represents hydrogen atom or an acyl group, $R^3$ is hydrogen atom, $R^4$ is a group represented by the following formula:

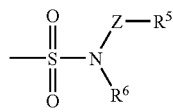

wherein $R^5$ represents a cyclic group which may be substituted, Z represents a single bond or a $C_1$ to $C_4$ alkylene group which may be substituted; or when Z is substituted, said substituent may bind to $R^5$ to form a ring group, $R^6$ represents hydrogen atom or a $C_1$ to $C_6$ alkyl group which may be substituted; or $R^6$ may bind to Z or $R^5$ to form a ring group can be prepared, for example, by a method described in the reaction scheme 5.

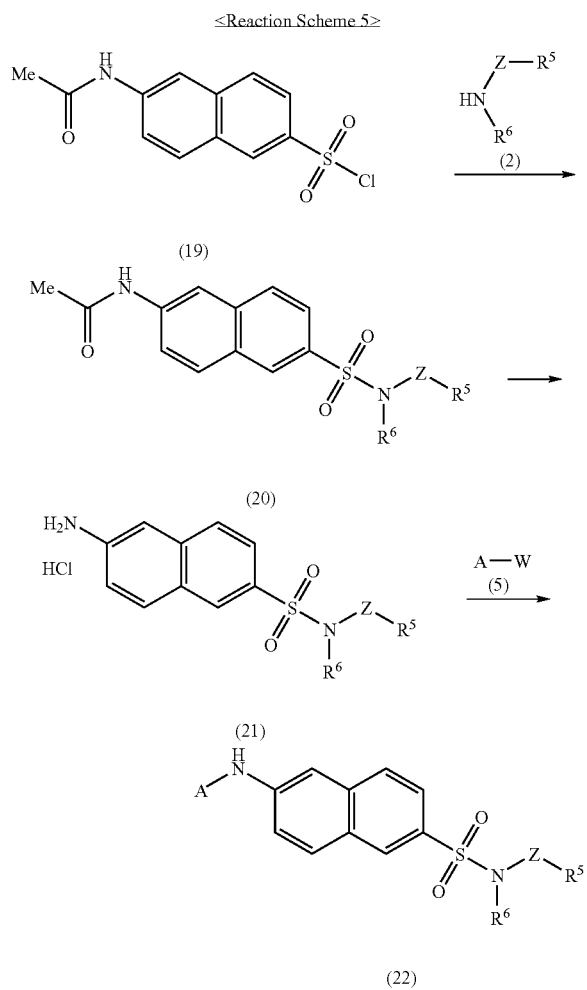

6-(Acetylamino)naphthalene-2-sulfonyl chloride (19) can be prepared, for example, by the method disclosed in the U.S. Pat. No. 5,378,715. The amine (2) wherein $R^5$, $R^6$, and Z have the same meanings as those defined in the general formula (I) can be obtained by methods described in the preparation method 1.

By reacting 6-(acetylamino)naphthalene-2-sulfonyl chloride (19) with the amine (2) wherein $R^5$, $R^6$, and Z have the same meanings as those defined in the general formula (I), the compound of the formula (20) wherein $R^5$, $R^6$, and Z have the same meanings as those defined in the general formula (I) can be obtained. The compound of the formula (20) is encompassed within the general formula (I). This reaction is carried out in the presence or absence of a base and/or a catalyst, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the catalysts include 4-dimethylaminopyridine and tetrabutylammonium bromide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

The acetyl group of the resulting compound of the formula (20) wherein $R^5$, $R^6$, and Z have the same meanings as those defined in the general formula (I) is then hydrolyzed to prepare the compounds represented by the formula (21). The compound of the formula (21) is encompassed within the general formula (I). This reaction is carried out in the presence of an acid or a base, with or without a solvent, at a reaction temperature of from 0° C. to a refluxing temperature of a solvent (at a reaction temperature of from 0° C. to 150° C., when the reaction is carried out without a solvent).

Examples of the acids include mineral acids such as hydrochloric acid and sulfuric acid; and Lewis acids such as triethyloxonium tetrafluoroborate. Examples of the bases include inorganic bases such as sodium hydroxide, potassium hydroxide, and metallic sodium; and organic bases such as hydrazine. Any solvent can be used as long as it does not inhibit the reaction, and examples include ethers such as tetrahydrofuran, 1,2-dimethoxyethane, and 1,4-dioxane; alcohols such as methanol, ethanol, 1-propanol, and 2-propanol; and water. These solvents can be used alone or as a mixture, or as two phase solvents.

The compound of the formula (21) wherein $R^5$, $R^6$, and Z have the same meanings as those defined in the general formula (I) is then reacted with the acylating agent (5) wherein A represents an acyl group, W represents halogen atom; acyloxy group such as acetoxy group, benzoyloxy group, methanesulfonyl group, and tosyl group; imidoxy group such as (2,5-dioxopyrrolidin-1-yl group; 1-imidazolyl group; and hydroxy group, to prepare the compounds represented by the formula (22), which are encompassed within the general formula (I), wherein A, $R^5$, $R^6$, and Z have the same meanings as those defined in the general formula (I). This reaction is carried out in the presence or absence of a base and/or an adjuvant for acylation, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the adjuvants for acylation include catalysts such as 4-dimethylaminopyridine and tetrabutylammonium bromide; halogenating agents such as thionyl chloride, phosphorus oxychloride, phosphorus trichloride, ethyl chloroformate, and 4-nitrobenzenesulfonyl chloride; carbodiimides such as N,N'-dicyclohexylcarbodiimide and 1-[3-(dimethylamino)propyl]-3-ethylcarbodiimide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

<<Preparation Method 6>>

In the compounds represented by the general formula (I) of the present invention, the compounds wherein $R^1$ is a group represented by the formula —NH-A wherein A represents hydrogen atom or an acyl group, $R^2$ is hydrogen atom, $R^3$ is a group represented by the following formula:

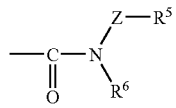

wherein $R^5$ represents a cyclic group which may be substituted, Z represents a single bond or a $C_1$ to $C_4$ alkylene group which may be substituted; or when Z is substituted, said substituent may bind to $R^5$ to form a ring group, $R^6$ represents hydrogen atom or a $C_1$ to $C_6$ alkyl group which may be substituted; or $R^6$ may bind to Z or $R^5$ to form a ring group, $R^4$ is hydrogen atom can be prepared, for example, by a method described in the reaction scheme 6.

<Reaction Scheme 6>

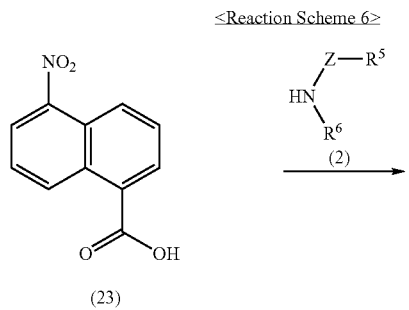

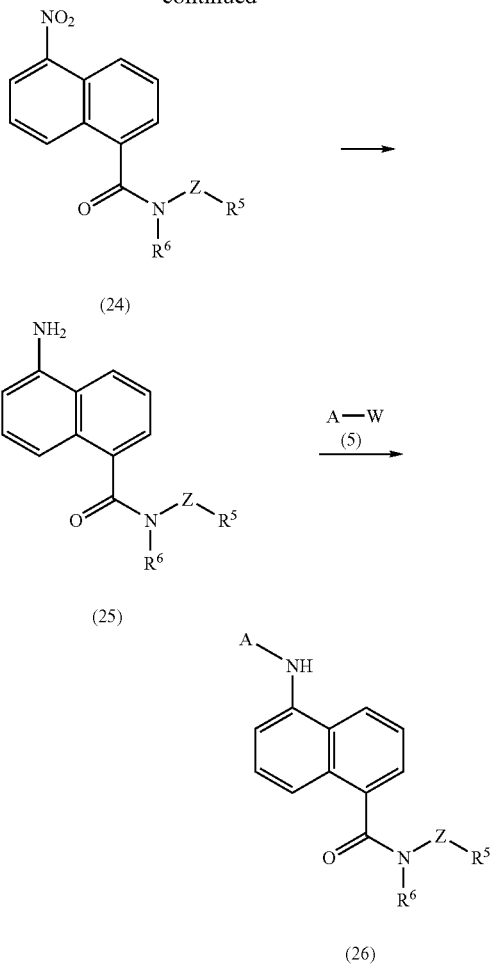

5-Nitronaphthalene-1-carboxylic acid (23) can be prepared, for example, by the method disclosed in Tetrahedron, volume 49, No. 17, pp. 3655-3663(published in 1993). The amine (2) wherein $R^5$, $R^6$, and Z have the same meanings as those defined in the general formula (I) can be obtained by methods described in the preparation method 1.

By reacting 5-nitronaphthalene-1-carboxylic acid (23) with the amine (2) wherein $R^5$, $R^6$, and Z have the same meanings as those defined in the general formula (I), the compound of the formula (24) wherein $R^5$, $R^6$, and Z have the same meanings as those defined in the general formula (I) can be obtained. This reaction is carried out in the presence of an adjuvant for acylation and/or a base, with or without a solvent, at a reaction temperature of from −30° C. to a refluxing temperature of a solvent (at a reaction temperature of from −30° C. to 150° C., when the reaction is carried out without a solvent).

Examples of the adjuvants for acylation include halogenating agents such as thionyl chloride, phosphorus oxychloride, phosphorus trichloride, ethyl chloroformate, and 4-nitrobenzenesulfonyl chloride; carbodiimides such as N,N'-dicyclohexylcarbodiimide and 1-[3-(dimethylamino)propyl]-3-ethylcarbodiimide; and carbonyldiimidazole. Examples of the bases include organic bases such as pyridine, triethylamine, ethyldiisopropylamine, N,N-diethylaniline, and 4-dimethylaminopyridine. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

The nitro group of the resulting compound of the formula (24) wherein $R^5$, $R^6$, and Z have the same meanings as those defined in the general formula (I) is then reduced to prepare the compounds represented by the formula (25). The compound of the formula (25) is encompassed within the general formula (I). This reaction is carried out in the presence or absence of a reducing agent, and an acid or a base, with or without a solvent, at a reaction temperature of from 0° C. to a refluxing temperature of a solvent (at a reaction temperature of from 0° C. to 150° C., when the reaction is carried out without a solvent).

Examples of the reducing agents include noble metals such as palladium on carbon, palladium black, platinium oxide, and Raney nickel; simple metals such as sodium, lithium, aluminium, iron, tin, and zinc; and metal salts such as tin(IV) chloride. Examples of the acids include mineral acids such as hydrochloric acid and sulfuric acid; and organic acids such as formic acid and acetic acid. Examples of the bases include organic bases such as triethylamine, pyridine, and quinoline. Any solvent can be used as long as it does not inhibit the reaction, and examples include esters such as ethyl formate, methyl acetate, ethyl acetate, and butyl acetate; ethers such as tetrahydrofuran, 1,2-dimethoxyethane, and 1,4-dioxane; alcohols such as methanol, ethanol, 1-propanol, and 2-propanol; ketones such as acetone and methyl ethyl ketone; and water. These solvents can be used alone or as a mixture, or as two phase solvents.

The compound of the formula (25) wherein $R^5$, $R^6$, and Z have the same meanings as those defined in the general formula (I) is then reacted with the acylating agent (5) wherein A represents an acyl group, W represents halogen atom; acyloxy group such as acetoxy group, benzoyloxy group, methanesulfonyl group, and tosyl group; imidoxy group such as (2,5-dioxopyrrolidin-1-yl group; 1-imidazolyl group; and hydroxy group, to prepare the compounds represented by the formula (26), which are encompassed within the general formula (I), wherein A, $R^5$, $R^6$, and Z have the same meanings as those defined in the general formula (I). This reaction is carried out in the presence or absence of a base and/or an adjuvant for acylation, with or without a solvent, at a reaction temperature of from −30° C. to a refluxing temperature of a solvent (at a reaction temperature of from −30° C. to 150° C., when the reaction is carried out without a solvent).

Examples of the bases include inorganic bases such as sodium hydroxide, potassium hydroxide, sodium carbonate, potassium carbonate, and sodium hydrogencarbonate; and organic bases such as pyridine, triethylamine, ethyldiisopropylamine, and N,N-diethylaniline. Examples of the adjuvants for acylation include catalysts such as 4-dimethylaminopyridine and tetrabutylammonium bromide; halogenating agents such as thionyl chloride, phosphorus oxychloride, phosphorus trichloride, ethyl chloroformate, and 4-nitrobenzenesulfonyl chloride; carbodiimides such as N,N'-dicyclohexylcarbodiimide and 1-[3-(dimethylamino)propyl]-3-ethylcarbodiimide. Any solvent can be used as long as it does not inhibit the reaction, and examples include esters such as ethyl formate, methyl acetate, ethyl acetate, and butyl acetate; halides such as dichloromethane, dichloroethane, and chloroform; ethers such as tetrahydrofuran, 1,2-dimethoxyethane, and 1,4-dioxane; substituted or unsubstituted benzenes such as benzene, toluene, monochlorobenzene, and 1,2-dichlorobenzene; amides such as N,N-dimethylformamide and N-methylpyrrolidone; alcohols such as methanol, ethanol, 1-propanol, and 2-propanol; ketones such as acetone and methyl ethyl ketone; and water. These solvents can be used alone or as a mixture, or as two phase solvents.

Examples of preparation methods of the salts of the compounds represented by the general formula (I) include a direct preparation of salts by a hydrolysis of the compounds of the aforementioned formulas (3), (8), (12), (16), or (20), or a reduction of the compounds of the aforementioned formula (24); and a preparation wherein the free form of the compounds represented by the general formula (I) is first prepared by the above hydrolysis or reduction, and then the free form is converted to salts. These methods are easily understood by those skilled in the art.

In the examples of the specification, methods for preparation of typical compounds falling within the general formula (I) are explained in detail. Accordingly, those skilled in the art can prepare any compound encompassed within the general formula (I) by referring to the general explanations of the aforementioned preparation methods and specific explanations of the preparation methods of the examples, and by choosing appropriate starting materials, reagents, and reaction conditions and by adding appropriate modification and alteration to these methods, if necessary.

Medicaments of the present invention can be used to enhance the effect of cancer therapy based on the mode of action of DNA injury, including cancer chemotherapies by using anticancer agents and radiation therapies of cancer that induce DNA injury. Typical examples of anticancer agents that induces DNA injury include bleomycin, adriamycin, cisplatin, cyclophosphamide, and mitomycinC. Besides these derivatives, any of anticancer agents involving the mode of action of DNA injury can be targets of the medicaments of the present invention. The medicaments of the present invention may be used where either of a cancer chemotherapy using anticancer agents or a radiation therapy of cancer that induce DNA injury is solely carried out, or in a cancer therapy where a combination of these therapies is carried out.

As the active ingredient of the medicament of the present invention, a hydrate or a solvate of the compounds represented by the aforementioned general formulas (I) or pharmacologically acceptable salts thereof may be used. Furthermore, when the compound contains one or more asymmetric carbon atoms, any of a pure form of optically active compound or any mixture of optically active compounds, or a racemate may be used. As the active ingredient of the medicament of the present invention, one or more kinds of substances selected from the group consisting of the aforementioned compound and a pharmacologically acceptable salt thereof, and a hydrate thereof and a solvate thereof may be used.

As the medicament of the present invention, the aforementioned substance, per se, may be administered. Preferably, the medicament may be administered as a pharmaceutical composition for oral or parenteral administration that may be prepared by methods well known to those skilled in the art. Examples of pharmaceutical compositions suitable for oral administration include tablets, capsules, powders, subtilized granules, granules, solution, and syrup, and examples of pharmaceutical compositions suitable for parenteral administration include injections, suppositories, inhalants, instillations, nasal drops, ointments, percutaneous absorbents, transmucosal absorptions, cream, and plaster.

The aforementioned pharmaceutical compositions can be prepared by adding pharmacologically and pharmaceutically acceptable additives. Examples of pharmacologically and pharmaceutically acceptable additives include excipients, disintegrators or disintegration aids, binders, lubricants, coating agents, colorants, diluents, base materials, dissolving aids or dissolution adjuvants, isotonizing agents, pH modifiers, stabilizers, propellants, and adhesives. One or more kinds of anticancer agents based on the mode of action of DNA injury may be added to the aforementioned pharmaceutical compositions.

A dose of the medicament of the present invention is not particularly limited. The dose may be selected appropriately depending on a kind of the active ingredient and a kind of a cancer therapy. Further, the dose may be appropriately increased or decreased depending on various factors that should be generally considered such as the weight and age of a patient, a kind and symptom of a disorder, and an administration route. Generally, for an oral administration, the medicament may be used in a range of 0.01 to 1,000 mg for an adult per day.

EXAMPLES

The present invention will be explained more specifically with reference to the following examples. However the scope of the present invention is not limited to the following examples.

Example 1

Preparation of N-benzyl-5-{[(4-methylphenyl)sulfonyl]oxy}naphthalene-1-sulfonamide (Compound No. 1-1)

(1) Preparation of 5-{[(4-methylphenyl)sulfonyl]oxy}naphthalene-1-sulfonyl chloride This compound was prepared by the preparation method disclosed in the U.S. Pat. No. 5,378,715.

$^1$H-NMR(CDCl$_3$): δ 2.46(3H, s), 7.33-7.35(3H, m), 7.59 (1H, dd, J=8.4, 7.8 Hz), 7.70(1H, dd, J=8.4, 7.8 Hz), 7.79(2H, d, J=8.4 Hz), 8.38(1H, dd, J=7.8, 1.2 Hz), 8.40(1H, dd, J=8.4, 0.9 Hz), 8.70(1H, d, J=8.7 Hz).

(2) Preparation of N-benzyl-5-{[(4-methylphenyl)sulfonyl]oxy}naphthalene-1-sulfonamide Triethylamine (0.17 ml, 1.2 mmol) was added to benzylamine (117.9 mg, 1.1 mmol) dissolved in tetrahydrofuran (5 ml). After the solution was cooled in the ice bath, 5-{[(4-methylphenyl)sulfonyl]oxy}naphthalene-1-sulfonyl chloride (396.9 mg, 1.2 mmol) was added, and the mixture was stirred at room temperature for 1 hour. The reaction mixture was poured into diluted hydrochloric acid and extracted with ethyl acetate. After the organic layer was washed with saturated brine, dried over anhydrous sodium sulfate, the residue obtained by evaporation of the solvent under reduced pressure was purified by column chromatography on silica gel (eluent; n-hexane : ethyl acetate=2:1) and crystallized (ethyl acetate/hexane) to give the title compound as a white crystal (398.8 mg, 85.3%).

$^1$H-NMR(DMSO-d$_6$): δ 2.41(3H, s), 4.04(2H, d, J=6.0 Hz), 7.06-7.14(5H, m), 7.35(1H, d, J=7.5 Hz), 7.47(2H, d, J=8.4 Hz), 7.61(1H, dd, J=8.4, 7.2 Hz), 7.69(1H, dd, J=8.4, 8.1 Hz), 7.85(2H, d, J=8.4 Hz), 8.10(1H, d, J=8.7 Hz), 8.13 (1H, d, J=7.5 Hz), 8.61(1H, d, J=8.7 Hz), 8.64(1H, t, J=6.0 Hz).

Example 2 to Example 27

The following compounds were prepared in the same manner as the method of Example 1(2).

Example 2

(Compound 1-2); Yield: 89.0%

(DMSO-d$_6$): δ 2.41(3H, s), 4.07(2H, d, J=5.7 Hz), 6.74 (2H, t, J=7.8 Hz), 7.10-7.20(1H, m), 7.31(1H, dd, J=7.8, 0.9 Hz), 7.48(2H, d, J=8.4 Hz), 7.59(1H, dd, J=8.4, 7.2 Hz), 7.64(1H, dd, J=8.7, 7.8 Hz), 7.84(2H, d, J=8.4 Hz), 8.08(1H, ddd, J=8.7, 7.5, 1.2 Hz), 8.53(1H, d, J=9.0 Hz), 8.66(1H, t, J=5.7 Hz).

Example 3

(Compound 1-3); Yield: 86.9%

(DMSO-d$_6$): δ 2.41(3H, s), 4.11(2H, d, J=5.7 Hz), 7.18 (1H, dd, J=8.4, 2.1 Hz), 7.27(1H, d, J=8.7 Hz), 7.34-7.37(2H, m), 7.47(2H, d, J=8.4 Hz), 7.59(1H, dd, J=8.4, 7.5 Hz), 7.69 (1H, dd, J=8.4, 8.1 Hz), 7.84(2H, d, J=8.4 Hz), 8.08(1H, d, J=3.0 Hz), 8.11(1H, s), 8.58(1H, d, J=8.1 Hz), 8.73(1H, t, J=5.7 Hz).

Example 4

(Compound 1-4); Yield: 98.5

(DMSO-d$_6$): δ 2.42(3H, s), 4.03(2H, d, J=7.2 Hz), 7.28 (1H, d, J=7.5 Hz), 7.33(1H, dd, J=8.7, 7.5 Hz), 7.46-7.49(3H, m), 7.57(1H, dd, J=8.4, 7.5 Hz), 7.68(1H, dd, J=8.7, 7.5 Hz), 7.85(2H, d, J=8.4 Hz), 7.89-7.91(2H, m), 8.05(1H, d, J=8.7 Hz), 8.12(1H, dd, J=7.2, 1.2 Hz), 8.56(1H, d, J=8.7 Hz), 8.86(1H, t, J=6.3 Hz).

Example 5

(Compound 1-5); Yield: 90.9%

(DMSO-d$_6$): δ 2.42(3H, s), 4.19(2H, d, J=6.3 Hz), 7.32 (1H, dd, J=7.8, 0.9 Hz), 7.37(2H, d, J=9.0 Hz), 7.48(2H, dd, J=8.7, 0.9 Hz), 7.62(1H, dd, J=8.4, 7.2 Hz), 7.70(1H, dd, J=8.4, 7.8 Hz), 7.85(2H, d, J=8.1 Hz), 7.99(2H, d, J=8.7 Hz), 8.10(1H, dt, J=8.7, 0.9 Hz), 8.14(1H, dd, J=7.5, 1.2 Hz), 8.58(1H, d, J=8.7 Hz), 8.85(1H, t, J=6.3 Hz).

Example 6

(Compound 1-6); Yield: 83.3%

(DMSO-d$_6$): δ 2.03(3H, s), 2.41(3H, s), 4.00(2H, d, J=5.7 Hz), 6.94-7.00(2H, m), 7.06(2H, t, J=6.3 Hz), 7.37(1H, d, J=7.2 Hz), 7.47(2H, d, J=8.4 Hz), 7.61(1H, dd, J=8.7, 7.2 Hz), 7.69(1H, dd, J=8.7, 7.8 Hz), 7.85(2H, d, J=8.1 Hz), 8.10(1H, d, J=8.7 Hz), 8.12(1H, dd, J=6.3, 1.2 Hz), 8.46(1H, t, J=6.0 Hz), 8.64(1H, d, J=8.4 Hz).

Example 7

(Compound 1-7); Yield: 77.3%

(DMSO-d$_6$): δ 1.19(9H, s), 2.40(3H, s), 3.98(2H, d, J=6.0 Hz), 6.97(2H, d, J=8.5 Hz), 7.12(2H, d, J=8.4 Hz), 7.34(1H, d, J=7.8 Hz), 7.46(2H, d, J=8.1 Hz), 7.59(1H, dd, J=8.4, 7.5 Hz), 7.68(1H, dd, J=8.7, 7.8 Hz), 7.84(2H, d, J=8.7 Hz), 8.08(1H, d, J=7.8 Hz), 8.11(1H, d, J=7.2 Hz), 8.57(1H, t, J=6.0 Hz), 8.60(1H, d, J=8.7 Hz).

Example 8

(Compound 1-8); Yield: 86.1%

(CDCl$_3$): δ 2.44(3H, s), 4.28(2H, d, J=6.6 Hz), 5.00(1H, t, J=6.6 Hz), 7.29-7.34(6H, m), 7.48(1H, dd, J=8.4, 7.5 Hz), 7.50-7.53(1H, m), 7.55(1H, dd, J=9.0, 7.5 Hz), 7.76(2H, d, J=8.4Hz), 8.19(1H, dt, J=8.7, 1.2 Hz), 8.25(1H, dd, J=7.5, 1.2 Hz), 8.51(1H, dt, J=9.0, 0.9 Hz).

Example 9

(Compound 1-9); Yield: 93.3%

(DMSO-d$_6$): δ 2.41(3H, s), 4.14(2H, d, J=6.0 Hz), 7.30 (2H, d, J=8.4 Hz), 7.34(1H, dd, J=7.5, 0.6 Hz), 7.47(4H, d, J=8.7 Hz), 7.60(1H, dd, J=8.7, 7.5 Hz), 7.70(1H, dd, J=8.7, 7.5 Hz), 7.84(2H, d, J=8.1 Hz), 8.09(1H, d, J=8.4 Hz), 8.12 (1H, dd, J=7.5, 1.2 Hz d, J=8.7 Hz), 8.77(1H, t, J=6.3 Hz).

Example 10

(Compound 1-10); Yield: 36.9

(CDCl$_3$): δ 2.47(3H, s), 3.97(2H, d, J=5.7 Hz), 5.03(1H, t, J=6.0 Hz), 5.49(2H, s), 6.24(1H, d, J=2.4 Hz), 6.34(1H, dd, J=8.1, 2.1 Hz), 6.54(1H, d, J=7.8 Hz), 7.24(1H, dd, J=7.2, 1.2 Hz), 7.37(2H, dd, 8.7, 0.9 Hz), 7.49-7.54(2H, m), 7.884(2H, dt, J=8.4, 1.8 Hz), 8.22-8.26(2H, m), 8.52(1H, d, J=8.7 Hz).

Example 11

(Compound 1-11); Yield: 88.1%

(CDCl$_3$): δ 2.44(3H, s), 3.35(3H, s), 4.12(2H, d, J=6.9 Hz), 5.45(1H, t, J=6.6 Hz), 6.33(1H, d, J=8.1 Hz), 6.59(1H, td, J=7.5, 0.9 Hz), 6.79(1H, dd, J=7.5, 1.8 Hz), 6.97(1H, td, J=7.8, 1.8 Hz), 7.28-7.35(4H, m), 7.51(1H, t, J=8.4 Hz), 7.77(2H, d, J=8.1 Hz), 8.02(1H, dd, J=8.4, 0.9 Hz), 8.06(1H, dd, J=7.5, 1.2 Hz), 8.45(1H, d, J=9.0 Hz).

Example 12

(Compound 1-12); Yield: 86.6%

(DMSO-d$_6$): δ 2.41(3H, s), 3.53(3H, s), 4.02(2H, d, J=6.3 Hz), 6.60-6.67(3H, m), 7.02(1H, t, J=8.1 Hz), 7.34(1H, dd, J=7.8, 1.2 Hz), 7.47(2H, d, J=8.4 Hz), 7.60(1H, dd, J=8.7, 7.5 Hz), 7.69(1H, dd, J=8.7, 8.1 Hz), 7.85(2H, d, J=8.4 Hz), 8.09(1H, d, J=8.4 Hz), 8.12(1H, dd, J=7.2, 0.9 Hz), 8.61(1H, d, J=8.7 Hz), 8.64(1H, t, J=6.0 Hz).

Example 13

(Compound 1-13); Yield: 89.7%

(DMSO-d$_6$): δ 2.41(3H, s), 3.52(3H, s), 3.73(3H, s), 4.03 (2H, d, J=6.0 Hz), 6.71(1H, dd, J=6.9, 2.1 Hz), 6.79-6.86(2H, m), 7.35(1H, d, J=8.1 Hz), 7.47(2H, d, J=8.1 Hz), 7.63(1H, dd, J=8.4, 7.5 Hz), 7.69(1H, dd, J=8.4, 8.1 Hz), 7.85(2H, d, J=8.4 Hz), 8.11(1H, d, J=8.4 Hz), 8.15(1H, d, J=7.2 Hz), 8.48(1H, t, J=6.0 Hz), 8.63(1H, d, J=8.7 Hz).

Example 14

(Compound 1-14); Yield: 94.2%

(CDCl$_3$): δ 2.44(3H, s), 3.60(6H, s), 4.04(2H, d, J=6.3 Hz), 4.93(1H, t, J=5.4 Hz), 6.14(2H, d, J=2.1 Hz), 6.24(1H, t, J=2.1 Hz), 7.29-7.33(3H, m), 7.48(1H, dd, J=8.4, 7.5 Hz), 7.56(1H, t, J=8.4 Hz), 7.78(2H, d, J=8.7 Hz), 8.19(1H, d, J=8.7 Hz), 8.26(1H, d, J=7.5 Hz), 8.57(1H, d, J=8.7 Hz).

Example 15

(Compound 1-15); Yield: 94.4%

(DMSO-d$_6$): δ 2.41(3H, s), 3.94(2H, d, J=6.3 Hz), 5.89 (2H, s), 6.50(1H, dd, J=8.1, 1.5 Hz), 6.57(1H, d, J=1.2 Hz), 6.62(1H, d, J=8.1 Hz), 7.33(1H, dd, J=7.8, 0.9 Hz), 7.47(2H, d, J=7.8 Hz), 7.61(1H, dd, J=8.7, 7.2 Hz), 7.68(1H, dd, J=8.7, 7.8 Hz), 7.84(2H, d, J=8.4 Hz), 8.09(1H, d, J=8.7 Hz), 8.11 (1H, dd, J=7.5, 1.2 Hz), 8.55(1H, t, J=6.3 Hz), 8.58(1H, d, J=9.0 Hz).

Example 16

(Compound 1-16); Yield: 85.4%

(DMSO-d$_6$): δ 2.41(3H, s), 3.84(2H, d, J=6.0 Hz), 5.02 (2H, s), 6.23(1H, d, J=7.8 Hz), 6.37(1H, d, J=7.5 Hz), 6.42 (1H, s), 6.81(1H, t, J=7.8 Hz), 7.35(1H, d, J=7.8 Hz), 7.47 (2H, d, J=8.4 Hz), 7.64(1H, t, J=7.5 Hz), 7.69(1H, t, J=7.8 Hz), 7.85(2H, d, J=8.4 Hz), 8.11-8.15(2H, m), 8.50(1H, t, J=6.0 Hz), 8.63(1H, d, J=8.7 Hz).

Example 17

(Compound 1-17); Yield: 88.3%

(DMSO-d$_6$): δ 2.40(3H, s), 2.80(6H, s), 3.89(2H, d, J=6.0 Hz), 6.47(2H, d, J=8.7 Hz), 6.86(2H, d, J=8.7 Hz), 7.34(1H, dd, J=7.8, 0.9 Hz), 7.46(2H, d, J=8.1 Hz), 7.61(1H, dd, J=8.7, 7.2 Hz), 7.68(1H, dd, J=8.7, 7.5 Hz), 7.84(2H, d, J=8.4 Hz), 8.08-8.14(2H, m), 8.42(1H, t, J=6.0 Hz), 8.60(1H, d, J=8.7 Hz).

Example 18

(Compound 1-18); Yield: 86.9%

(DMSO-d$_6$): δ 2.41(3H, s), 3.14(3H, s), 4.16(2H, d, J=6.3 Hz), 7.35(1H, d, J=7.2 Hz), 7.37(2H, d, J=8.1 Hz), 7.48(2H, d, J=8.4 Hz), 7.62(1H, dd, J=8.7, 7.5 Hz), 7.70(2H, d, J=8.1 Hz), 7.76(1H, t, J=4.8 Hz), 7.85(2H, d, J=8.4 Hz), 8.11-8.14 (2H, m), 8.60(1H, d, J=8.7 Hz), 8.81(1H, t, J=6.3 Hz).

Example 19

(Compound 1-19); Yield: 87.1%

(DMSO-d$_6$): δ 2.40(3H, s), 4.47(2H, d, J=5.7 Hz), 7.28-7.34(4H, m), 7.42(1H, d J=7.5 Hz), 7.47(2H, d, J=8.1 Hz), 7.58(1H, dd, J=8.4, 7.2 Hz), 7.64(1H, dd, J=8.7, 7.8 Hz), 7.76(1H, dd, J=7.5, 1.8 Hz), 7.83-7.89(4H, m), 8.08(1H, d, J=8.4 Hz), 8.13(1H, dd, J=7.2, 0.9 Hz), 8.62(1H, d, J=8.7 Hz), 8.65(1H, t, J=5.4 Hz).

Example 20

(Compound 1-20); Yield: 87.9%

(DMSO-$d_6$): δ 1.82(3H, s), 2.42(3H, s), 4.01(2H, d, J=6.0 Hz), 5.65(1H, dd, J=3.0, 1.2 Hz), 5.79(1H, d, J=3.0 Hz), 7.33(1H, dd, J=7.5, 0.9 Hz), 7.48(2H, d, J=8.7 Hz), 7.61(1H, dd, J=8.7, 7.8 Hz), 7.67(1H, dd, J=8.7, 7.8 Hz), 7.86(2H, d, J=8.7 Hz), 8.09(1H, t, J=7.8 Hz), 8.10(1H, t, J=7.8 Hz), 8.55-8.61(2H, m).

Example 21

(Compound 1-21); Yield: 91.9%

(DMSO-$d_6$): δ 2.41(3H, s), 4.14(2H, d, J=6.3 Hz), 7.08-7.16(2H, m), 7.35(1H, d, J=7.2 Hz), 7.48(2H, d, J=8.1 Hz), 7.50-7.55(1H, m), 7.59(1H, dd, J=8.7, 7.5 Hz), 7.70(1H, t, J=8.1 Hz), 7.85(2H, d, J=8.7 Hz), 8.09(1H, d, J=8.4 Hz), 8.12(1H, dd, J=7.5, 1.2 Hz), 8.23-8.26(1H, m), 8.62(1H, d, J=8.7 Hz), 8.76(1H, t, J=6.3 Hz).

Example 22

(Compound 1-22); Yield: 93.7%

(DMSO-$d_6$): δ 2.41(3H, s), 4.22(2H, d, J=5.7 Hz), 7.12(1H, d, J=2.7 Hz), 7.14(1H, d, J=3.0 Hz), 7.34(1H, d, J=7.2 Hz), 7.42(1H, d, J=3.6 Hz), 7.44(1H, d, J=3.6 Hz), 7.47(2H, d, J=8.4 Hz), 7.62(1H, dd, J=8.7, 7.5 Hz), 7.70(1H, dd, J=8.7, 7.8 Hz), 7.84(2H, d, J=8.7 Hz), 8.10(1H, d, J=8.7 Hz), 8.19(1H, dd, J=7.2, 0.9 Hz), 8.64(1H, d, J=8.7 Hz), 8.83(1H, t, J=5.7 Hz).

Example 23

(Compound 1-23); Yield: 88.7%

(DMSO-$d_6$): δ 0.61-0.72(2H, m), 0.95-1.04(3H, m), 1.19(1H, bs), 1.49-1.52(5H, m), 2.40(3H, s), 2.61(2H, t, J=6.3 Hz), 7.46(1H, d, J=7.8 Hz), 7.46(2H, d, J=8.4 Hz), 7.66(1H, t, J=7.8 Hz), 7.70(1H, dd, J=8.7, 7.8 Hz), 7.84(2H, d, J=8.4 Hz), 8.04(1H, t, J=6.0 Hz), 8.14(2H, d, J=7.8 Hz), 8.62(1H, d, J=9.0 Hz).

Example 24

(Compound 1-24); Yield: 87.8%

(CDCl$_3$): δ 2.42(3H, s), 6.67(1H, s), 6.88-6.91(2H, m), 7.07-7.19(2H, m), 7.25-7.27(3H, m), 7.33-7.38(2H, m), 7.57(1H, dd, J=8.7, 7.8 Hz), 7.72(2H, d, J=8.4 Hz), 8.12(1H, dt, J=7.8, 0.9 Hz), 8.16(1H, dd, J=7.5, 1.2 Hz), 8.58(1H, d, J=8.7 Hz).

Example 25

(Compound 1-25); Yield: 98.3%

(DMSO-$d_6$): δ 2.36(3H, s), 2.57(2H, t, J=7.2 Hz), 3.00-3.06(2H, m), 7.00(2H, dd, J=8.1, 2.1 Hz), 7.10-7.18(3H, m), 7.37(2H, d, J=7.5 Hz), 7.43(2H, d, J=8.7 Hz), 7.63(1H, dd, J=8.4, 7.2 Hz), 7.68(1H, t, J=8.4 Hz), 7.83(2H, d, J=8.4 Hz), 8.12(1H, d, J=8.7 Hz), 8.13(1H, d, J=7.5 Hz), 8.18(1H, t, J=6.0 Hz), 8.57(1H, d, J=8.7 Hz).

Example 26

(Compound 1-26); Yield: 81.5%

(DMSO-$d_6$): δ 1.15(3H, d, J=6.9 Hz), 2.40(3H, s), 4.26-4.36(1H, m), 6.90-6.97(5H, m), 7.34(1H, d, J=7.2 Hz), 7.45(2H, d, J=8.4 Hz), 7.48(1H, dd, J=8.7, 7.5 Hz), 7.67(1H, t, J=8.1 Hz), 7.82(2H, d, J=8.1 Hz), 7.99(1H, d, J=8.7 Hz), 8.01(1H, d, J=7.5 Hz), 8.58(1H, d, J=3.0 Hz), 8.60(1H, d, J=2.7 Hz).

Example 27

(Compound 1-27); Yield: 53.6%

(CDCl$_3$): δ 2.43(3H, s), 2.70(3H, s), 4.33(2H, s), 7.19-7.22(2H, m), 7.27-7.34(6H, m), 7.52(1H, dd, J=8.7, 7.8 Hz), 7.57(1H, dd, J=8.7, 7.8 Hz), 7.78(2H, d, J=8.4 Hz), 8.21-8.25(2H, m), 8.72(1H, d, J=8.4 Hz).

Example 28

Preparation of
N-benzyl-5-hydroxynaphthalene-1-sulfonamide
(Compound No. 2-1)

Methanol (5 ml) and 5N aqueous sodium hydroxide (0.65 ml) were added to 5-{[(4-methylphenyl)sulfonyl]oxy}naphthalene-1-sulfonamide (Compound No. 1-1; 298.8 mg, 0.64 mmol), and the mixture was stirred at 65° C. for 1 hour. After cooling to room temperature, the reaction mixture was poured into diluted hydrochloric acid and extracted with ethyl acetate. After the organic layer was washed with saturated brine, dried over anhydrous sodium sulfate, the residue obtained by evaporation of the solvent under reduced pressure was purified by column chromatography on silica gel (eluent; n-hexane : ethyl acetate=3:2→1:1) to give the title compound as a light brown white crystal (152.8 mg, 76.2%).
$^1$H-NMR(DMSO-$d_6$): δ 4.00(2H, d, J=6.0 Hz), 7.00(1H, d, J=7.5 Hz), 7.14-7.22(5H, m), 7.49(1H, dd, J=8.7, 7.5 Hz), 7.52(1H, dd, J=8.1, 7.5 Hz), 8.08-8.11(2H, m), 8.42(1H, d, J=8.1 Hz), 8.43(1H, t, J=6.0 Hz), 10.49(1H, s).

Example 29 to Example 53

The following compounds were prepared in the same manner as the method of Example 28. The compounds prepared in Example 2 to Example 9, and Example 11 to Example 27 were used as the law materials.

Example 29

(Compound 2-2); Yield: 76.2%

(DMSO-$d_6$): δ 4.05(2H, d, J=6.0 Hz), 6.83(2H, t, J=7.8 Hz), 6.97(1H, d, J=7.8 Hz), 7.16-7.27(1H, m), 7.43(1H, t, J=8.7 Hz), 7.49(1H, dd, J=8.1, 7.5 Hz), 8.01(1H, d, J=9.0 Hz), 8.06(1H, dd, J=7.2, 1.2 Hz), 8.38(1H, d, J=8.1 Hz), 8.41(1H, t, J=5.7 Hz), 10.43(1H, s).

Example 30

(Compound 2-3); Yield: 76.1%

(DMSO-$d_6$): δ 4.08(2H, d, J=6.0 Hz), 7.00(1H, d, J=7.8 Hz), 7.21(1H, dd, J=8.4, 2.4 Hz), 7.33(1H, d, J=8.7 Hz), 7.41(1H, d, J=1.8 Hz), 7.45-7.53(2H, m), 8.04(1H, d, J=8.1 Hz), 8.07(1H, dd, J=7.2, 1.2 Hz), 8.40(1H, d, J=8.4 Hz), 8.53(1H, t, J=6.0 Hz), 10.49(1H, s).

Example 31

(Compound 2-4); Yield: 69.4%

(DMSO-d$_6$): δ 4.17(2H, d, J=6.3 Hz), 6.95(1H, d, J=7.2 Hz), 7.37(1H, t, J=7.8 Hz), 7.43-7.52(3H, m), 7.89-7.94(2H, m), 8.02(1H, d, J=8.7 Hz), 8.06(1H, dd, J=7.5, 1.2 Hz), 8.34 (1H, d, J=8.7 Hz), 8.63(1H, t, J=6.3 Hz), 10.45(1H, s).

Example 32

(Compound 2-5); Yield: 48.5%

(DMSO-d$_6$): δ 4.15(2H, d, J=6.3 Hz), 6.99(1H, d, J=7.2 Hz), 7.39(2H, d, J=8.7 Hz), 7.46-7.52(2H, m), 7.99(2H, d, J=8.7 Hz), 8.04(1H, d, J=9.0 Hz), 8.07(1H, dd, H=7.2, 1.2 Hz), 8.38(1H, d, J=8.7 Hz), 8.63(1H, t, J=6.3 Hz), 10.61(1H, s).

Example 33

(Compound 2-6); Yield: 73.6%

(DMSO-d$_6$): δ 2.09(3H, s), 3.97(2H, d, J=6.0 Hz), 6.99-7.12(4H, m), 7.15(1H, d, J=7.2 Hz), 7.48(1H, dd, J=8.4, 7.8 Hz), 7.52(1H, dd, J=8.7, 7.5 Hz), 8.09(1H, dd, J=7.2, 1.2 Hz), 8.11(1H, d, J=8.1 Hz), 8.52(1H, t, J=6.0 Hz), 8.42(1H, dt, J=8.4, 1.2 Hz), 10.48(1H, s).

Example 34

(Compound 2-7); Yield: 62.8%

(DMSO-d$_6$): δ 1.20(9H, s), 3.95(2H, d, J=6.0 Hz), 6.99 (1H, dd, J=7.8, 0.6 Hz), 7.03(2H, d, J=8.7 Hz), 7.15(2H, d, J=8.4 Hz), 7.44-7.52(2H, m), 8.05-8.08(2H, m), 8.35(1H, t, J=6.0 Hz), 8.39(1H, dd, J=8.4, 1.2 Hz), 10.46(1H, s).

Example 35

(Compound 2-8); Yield: 40.7%

(DMSO-d$_6$): δ 4.19(2H, d, J=5.7 Hz), 7.01(1H, d, J=7.8 Hz), 7.38(1H, t, J=7.8 Hz), 7.45-7.61(4H, m), 8.05-8.11(2H, m), 8.41(1H, d, J=8.4 Hz), 8.61(1H, t, J=6.0 Hz), 10.50(1H, s).

Example 36

(Compound 2-9); Yield: 79.6%

(DMSO-d$_6$): δ 4.10(2H, d, J=6.3 Hz), 7.00(1H, d, J=6.9 Hz), 7.36(2H, d, J=7.8 Hz), 7.46-7.52(4H, m), 8.05(1H, d, J=8.7 Hz), 8.07(1H, dd, J=7.5, 1.2 Hz), 8.40(1H, d, J=8.1 Hz), 8.55(1H, t, J=6.3 Hz), 10.60(1H, s).

Example 37

(Compound 2-11); Yield: 72.2%

(DMSO-d$_6$): δ 3.64(3H, s), 3.98(2H, d, J=6.3 Hz), 6.73-6.79(2H, m), 6.99(1H, d, J=7.2 Hz), 7.10-7.19(2H, m), 7.48 (1H, t, J=8.7 Hz), 7.50(1H, t, J=7.8 Hz), 8.06(1H, dd, J=7.5, 1.2 Hz), 8.09(1H, d, J=8.7 Hz), 8.17(1H, t, J=6.3 Hz), 8.40 (1H, d, J=8.4 Hz), 10.46(1H, s).

Example 38

(Compound 2-12); Yield: 74.9%

(DMSO-d$_6$): δ 3.54(3H, s), 4.00(2H, d, J=6.3 Hz), 6.64-6.73(3H, m), 7.00(1H, d, J=7.8 Hz), 7.08(1H, t, J=7.8 Hz), 7.46-7.53(2H, m), 8.08(1H, dd, J=7.2, 1.5 Hz), d, J=8.4 Hz), 8.41(1H, d, J=7.2 Hz), 8.42(1H, t, J=5.7 Hz), 10.47(1H, s).

Example 39

(Compound 2-13); Yield: 63.1%

(DMSO-d$_6$): δ 3.56(3H, s), 3.74(3H, s), 4.00(2H, d, J=6.0 Hz), 6.81(1H, dd, J=6.0, 3.3 Hz), 6.86-6.90(2H, m), 7.00(1H, dd, J=7.5, 0.3 Hz), 7.48(1H, dd, J=8.7, 7.5 Hz), 7.53(1H, dd, J=8.4, 7.5 Hz), 8.08-8.11(2H, m), 8.27(1H, t, J=6.0 Hz), 8.42(1H, d, J=8.4 Hz), 10.49(1H, s).

Example 40

(Compound 2-14); Yield: 60.8%

(DMSO-d$_6$): δ 3.52(6H, s), 3.98(2H, d, J=6.3 Hz), 6.21-6.24(3H, m), 7.00(1H, d, J=7.8 Hz), 7.48(1H, t, J=8.7, 4.5 Hz), 7.51(1H, dd, J=7.5, 3.9 Hz), 8.08(1H, d, J=5.7, 1.2 Hz), 8.10(1H, d, J=5, 7 Hz), 8.40(1H, d, J=7.2 Hz), 8.42(1H, t, J=6.0 Hz), 10.48(1H, s).

Example 41

(Compound 2-15); Yield: 70.3%

(DMSO-d$_6$): δ 3.91(2H, d, J=6.3 Hz), 5.90(2H, s), 6.57 (1H, dd, J=7.8, 1.8 Hz), 6.61(1H, d, J=1.8 Hz), 6.67(1H, d, J=8.1 Hz), 6.99(1H, d, J=7.2 Hz), 7.48(1H, dd, J=9.0, 7.5 Hz), 7.50(1H, dd, J=8.7, 7.5 Hz), 8.04-8.07(2H, m), 8.34(1H, t, J=6.3 Hz), 8.40(1H, d, J=8.4 Hz), 10.46(1H, s).

Example 42

(Compound 2-16); Yield: 79.5%

(DMSO-d$_6$): δ 3.82(2H, d, J=6.3 Hz), 5.04(2H, s), 6.31 (1H, d, J=7.2 Hz), 6.40(1H, dd, J=8.1, 1.5 Hz), 6.47(1H, d, J=1.5 Hz), 6.86(1H, t, J=7.8 Hz), 7.00(1H, d, J=7.2 Hz), 7.48(1H, dd, J=8.4, 7.2 Hz), 7.54(1H, dd, J=8.4, 7.5 Hz), 8.09(1H, dd, J=7.2, 1.2 Hz), 8.10(1H, d, J=8.7 Hz), 8.29(1H, t, J=6.3 Hz), 8.43(1H, d, J=8.4 Hz), 10.48(1H, s).

Example 43

(Compound 2-17); Yield: 53.5%

(DMSO-d$_6$): δ 2.81(6H, s), 3.86(2H, d, J=6.0 Hz), 6.52 (2H, d, J=8.7 Hz), 6.93(2H, d, J=8.7 Hz), 6.99(1H, d, J=7.5 Hz), 7.47(1H, dd, J=8.7, 7.8 Hz), 7.52(1H, dd, J=8.4, 7.5 Hz), 8.06(1H, d, J=0.9 Hz), 8.09(1H, t, J=1.2 Hz), 8.20(1H, t, J=6.0 Hz), 8.40(1H, d, J=8.7 HZ).

Example 44

(Compound 2-18); Yield: 57.9%

(DMSO-d$_6$): δ 3.13(3H, s), 4.12(2H, d, J=6.3 Hz), 7.00 (1H, d, J=7.8 Hz), 7.37(2H, d, J=8.7 Hz), 7.47-7.52(2H, m), 7.67(2H, d, J=8.4 Hz), 8.05(1H, d, J=8.7 Hz), 8.07(1H, dd, J=7.2, 1.2 Hz), 8.39(1H, d, J=8.1 Hz), 8.59(1H, t, J=6.3 Hz), 10.50(1H, s).

Example 45

(Compound 2-19); Yield: 73.6%

(DMSO-$d_6$): δ 4.43(2H, d, J=5.7 Hz), 7.00(1H, d, J=7.8 Hz), 7.33-7.41(3H, m), 7.43-7.50(2H, m), 7.52(1H, dd, J=8.4, 7.2 Hz), 7.80(1H, dd, J=7.2, 1.8 Hz), 7.88(1H, d, J=7.5 Hz), 7.93(1H, d, J=8.4 Hz), 8.12(1H, d, J=8.7 Hz), 8.14(1H, dd, J=7.2, 1.2 Hz), 8.43(1H, d, =8.1 Hz), 8.44(1H, t, J=5.4 Hz), 10.48(1H, s).

Example 46

(Compound 2-20); Yield: 55.0%

(DMSO-$d_6$): δ 1.93(3H, s), 3.98(2H, d, J=5.7 Hz), 5.73 (1H, dd, J=2.7, 1.2 Hz), 5.85(1H, d, J=2.7 Hz), 6.98(1H, d, J=7.2 Hz), 7.43-7.52(2H, m), 8.01(1H, d, J=1.2 Hz), 8.04-8.05(1H, m), 8.35(1H, t, J=6.0 Hz), 8.40(1H, d, J=8.4 Hz), 10.44(1H, s).

Example 47

(Compound 2-21); Yield: 51.7%

(DMSO-$d_6$): δ 4.10(2H, d, J=6.0 Hz), 7.00(1H, d, J=7.5 Hz), 7.16(1H, t, J=6.0 Hz), 7.25(1H, d, J=7.8 Hz), 7.46-7.53 (2H, m), 7.60(1H, t, J=7.5 Hz), 8.08(2H, d, J=7.8 Hz), 8.34 (1H, d, J=3.9 Hz), 8.40(1H, d, J=8.4 Hz), 8.53(1H, t, J=6.0 Hz), 10.48(1H, s).

Example 48

(Compound 2-22); Yield: 57.6%

(DMSO-$d_6$): δ 4.17(2H, d, J=6.0 Hz), 7.01(1H, d, J=7.5 Hz), 7.13(1H, d, J=3.0 Hz), 7.15(1H, d, J=3.0 Hz), 7.46-7.52 (3H, m), 7.55(1H, dd, J=8.4, 7.2 Hz), 8.10(1H, d, J=8.7 Hz), 8.15(1H, dd, J=7.5, 1.2 Hz), 8.44(1H, d, J=8.4 Hz), 8.60(1H, t, J=6.0 Hz), 10.52(1H, s), 12.30(1H, s).

Example 49

(Compound 2-23); Yield: 67.0%

(CDCl$_3$): δ 0.68-0.81(2H, m), 1.01-1.11(3H, m), 1.26-1.34 (1H, m), 1.55-1.60(5H, m), 2.70(2H, t, J=6.6 Hz), 4.61(1H, t, J=6.6 Hz), 5.72(1H, s), 6.93(1H, dd, J=7.5, 6.0 Hz), 7.48(1H, dd, J=8.7, 7.5 Hz), 7.53(1H, dd, J=8.4, 7.8 Hz), 8.17(1H, d, J=8.7 Hz), 8.27(1H, dd, J=7.2, 1.2 Hz), 8.52(1H, dd, J=8.4, 1.2 Hz).

Example 50

(Compound 2-24); Yield: 51.8%

(CDCl$_3$): δ 6.92-7.02(4H, m), 7.06-7.12(2H, m), 7.37(1H, dd, J=8.7, 7.5 Hz), 7.46(1H, dd, J=8.7, 7.8 Hz), 8.16-8.23(2H, m), 8.49(1H, d, J=8.4 Hz), 8.74(1H, s), 9.41(1H, bs).

Example 51

(Compound 2-25); Yield: 63.9%

(DMSO-$d_6$): δ 2.36(3H, s), 2.57(2H, t, J=7.2 Hz), 3.00-3.06(2H, m), 7.00(2H, dd, J=8.1, 2.1 Hz), 7.10-7.18(3H, m), 7.37(2H, d, J=7.5 Hz), 7.43(2H, d, J=8.7 Hz), 7.63(1H, dd, J=8.4, 7.2 Hz), 7.68(1H, t, J=8.4 Hz), 7.83(2H, d, J=8.4 Hz), 8.12(1H, d, J=8.7 Hz), 8.13(1H, d, J=7.5 Hz), 8.18(1H, t, J=6.0 Hz), 8.57(1H, d, J=8.7 Hz).

Example 52

(Compound 2-26); Yield: 57.8%

(CDCl$_3$): δ 1.33(3H, d, J=6.9 Hz), 4.38-4.47(1H, m), 4.98 (1H, d, J=7.2 Hz), 6.45(1H, bs), 6.87-6.92(3H, m), 6.95-7.03 (3H, m), 7.36(1H, dd, J=8.4, 7.2 Hz), 7.42(1H, dd, J=8.7, 7.5 Hz), 8.07-8.13(2H, m), 8.41(1H, dt, J=8.1, 1.2 Hz)

Example 53

(Compound 2-27); Yield: 53.6%

(CDCl$_3$): δ 2.71(3H, s), 4.44(2H, s), 6.94(2H, d, J=7.5 Hz), 7.21-7.33(5H, m), 7.49(1H, dd, J=8.7, 7.5 Hz), 7.55(1H, dd, J=8.7, 7.5 Hz), 8.27(1H, dd, J=7.5, 1.2 Hz), 8.36(1H, d, J=8.7 Hz), 8.53-8.56(1H, m).

Example 54

Preparation of 5-acetyloxy-N-benzylnaphthalene-2-sulfonamide (Compound No. 3-1)

(1) Preparation of 5-(acetyloxy)naphthalene-2-sulfonyl chloride

This compound was prepared by the preparation method disclosed in Tetrahedron, volume 48, No. 42, pp. 9207-9216 (published in 1992), and Japanese Patent Kokai Koho Sho 60-140240.

(2) Preparation of 5-acetyloxy-N-benzylnaphthalene-2-sulfonamide

Triethylamine (50 μl, 0.36 mmol) and 5-(acetyloxy)naphthalene-2-sulfonyl chloride (84.9 mg, 0.30 mmol) were added to benzylamine (32.1 mg, 0.30 mmol) dissolved in tetrahydrofuran (3 ml), and the mixture was stirred at room temperature for 30 minutes. The reaction mixture was poured into diluted hydrochloric acid and extracted with ethyl acetate. After the organic layer was washed with saturated brine, dried over anhydrous sodium sulfate, the residue obtained by evaporation of the solvent under reduced pressure was purified by column chromatography on silica gel (eluent; n-hexane: ethyl acetate=2:1→1:1) to give the title compound as a light yellow white crystal (72.1 mg, 67.6%).

$^1$H-NMR(CDCl$_3$): δ 2.49(3H, s), 4.16(2H, d, J=6.3 Hz), 4.92(1H, t, J=6.0 Hz), 7.16-7.26(5H, m), 7.43(1H, dd, J=7.8, 1.2 Hz), 7.61(1H, dd, J=8.1, 7.8 Hz), 7.84(1H, d, J=8.4 Hz), 7.86(1H, dd, J=8.7, 1.8 Hz), 8.00(1H, d, J=8.7 Hz), 8.45(1H, d, J=2.1 Hz).

Example 55 to Example 68

The following compounds were prepared in the same manner as the method of Example 54(2).

Example 55

(Compound 3-2); Yield: 88.5%

(DMSO-$d_6$): δ 2.49(3H, s), 4.10(2H, d, J=6.3 Hz), 7.34 (1H, dd, J=8.4, 2.1 Hz), 7.44(1H, d, J=8.4 Hz), 7.47(1H, d,

J=2.4 Hz), 7.51(1H, d, J=7.5 Hz), 7.70(1H, t, J=7.8 Hz), 7.86(1H, dd, J=8.7, 1.5 Hz), 8.08(1H, d, J=8.1 Hz), 8.12(1H, d, J=9.0 Hz), 8.44(1H, t, J=6.3 Hz), 8.48(1H, s).

Example 56

(Compound 3-3); Yield: 91.7%

(DMSO-$d_6$): δ 2.48(3H, s), 4.22(2H, d, J=6.3 Hz), 7.48-7.53(2H, m), 7.66-7.72(2H, m), 7.85(1H, dd, J=8.7, 1.5 Hz), 7.97-8.00(1H, m), 8.04-8.11(3H, m), 8.48(1H, d, J=1.5 Hz), 8.55(1H, t, J=6.3 Hz).

Example 57

(Compound 3-4); Yield: 91.3%

(CDCl$_3$): δ 1.23(9H, s), 2.49(3H, s), 4.14(2H, d, J=6.3 Hz), 4.94(1H, t, J=6.3 Hz), 7.09(2H, d, J=8.4 Hz), 7.21-7.26(2H, m), 7.42(1H, dd, J=7.8, 0.9 Hz), 7.60(1H, dd, J=7.8, 7.5 Hz), 7.83(1H, d, J=8.7 Hz), 7.84(1H, dd, J=9.0, 1.8 Hz), 7.98(1H, d, J=9.3 Hz), 8.44(1H, d, J=2.1 Hz).

Example 58

(Compound 3-5); Yield: 92.9%

(DMSO-$d_6$): δ 2.48(3H, s), 4.15(2H, s), 7.46(2H, d, J=8.1 Hz), 7.50(1H, dd, J=7.5, 1.5 Hz), 7.58(2H, d, J=8.4 Hz), 7.69(1H, t, J=8.1 Hz), 7.86(1H, dd, J=9.0, 1.8 Hz), 8.06(1H, d, J=8.1 Hz), 8.11(1H, d, J=8.7 Hz), 8.47(2H, d, J=1.5 Hz).

Example 59

(Compound 3-6); Yield: 92.8%

(CDCl$_3$): δ 2.48(3H, s), 3.69(3H, s), 3.72(3H, s), 4.19(2H, d, J=6.6 Hz), 5.20(1H, t, J=6.3 Hz), 6.64(2H, d, J=7.5 Hz), 6.77(1H, dd, J=8.7, 6.9 Hz), 7.39(1H, dd, J=7.8, 1.2 Hz), 7.58(1H, dd, J=8.4, 7.2 Hz), 7.77-7.81(2H, m), 7.90(1H, d, J=8.7 Hz), 8.35(1H, d, J=1.8 Hz).

Example 60

(Compound 3-7); Yield: 63.7%

(DMSO-$d_6$): δ 2.49(3H, s), 3.83(2H, d, J=6.3 Hz), 5.03 (2H, s), 6.35(1H, d, J=7.5 Hz), 6.40(1H, d, J=7.2 Hz), 6.50 (1H, s), 6.88(1H, t, J=7.5 Hz), 7.51(1H, d, J=7.5 Hz), 7.70 (1H, t, J=7.8 Hz), 7.90(1H, dd, J=8.7, 1.5 Hz), 8.09-8.16(2H, m), 8.18(1H, t, J=6.0 HZ), 8.52(1H, d, J=1.8 Hz).

Example 61

(Compound 3-8); Yield: 65.8%

(DMSO-$d_6$): δ 4.50(3H, s), 4.46(2H, d, J=6.0 Hz), 7.37-7.45(2H, m), 7.48-7.53(3H, m), 7.71(1H, t, J=7.8 Hz), 7.81 (1H, d, J=7.8 Hz), 7.87-7.93(2H, m), 8.05-8.14(3H, m), 8.34 (1H, t, J=6.0 Hz), 8.56(1H, d, J=1.8 Hz).

Example 62

(Compound 3-9); Yield: 94.3%

(DMSO-$d_6$): δ 1.87(3H, s), 2.48(3H, s), 4.01(2H, d, J=6.0 Hz), 5.75(1H, dd, J=3.0, 1.2 Hz), 6.01(1H, d, J=3.0 Hz), 7.49(21, dd, J=7.2, 0.6 Hz), 7.68(1H, t, J=7.8 Hz), 7.81(1H, dd, J=9.0, 1.8 Hz), 8.06(1H, d, J=8.1 Hz), 8.08(1H, d, J=9.0 Hz), 8.29(1H, t, J=6.0 Hz), 8.43(1H, d, J=1.8 Hz).

Example 63

(Compound 3-10); Yield: 99.5%

(DMSO-$d_6$): δ 2.48(3H, s), 4.14(2H, d, J=6.3 Hz), 7.16 (1H, ddd, J=7.5, 4.8, 1.2 Hz), 7.35(1H, d, J=7.8 Hz), 7.50(1H, dd, J=7.5, 1.2 Hz), 7.63-7.72(2H, m), 7.87(1H, dd, J=9.0, 1.8 Hz), 8.07(1H, d, J=7.5 Hz), 8.10(1H, d, J=8.7 Hz), 8.37(1H, ddd, J=4.8, 1.8, 0.9 Hz), 8.44(1H, t, J=6.3 Hz), 8.49(1H, d, J=1.5 Hz).

Example 64

(Compound 3-11); Yield: 59.6%

(DMSO-$d_6$): δ 0.73-0.86(2H, m), 1.06-1.13(3H, m), 1.33 (1H, m), 1.54-1.66(5H, m), 2.48(3H, s), 2.60(2H, t, J=6.3 Hz), 7.50(1H, dd, J=7.5, 0.9 Hz), 7.69(1H, t, J=8.1 Hz), 7.74(1H, t, J=6.0 Hz), 7.86(1H, dd, J=8.7, 1.8 Hz), 8.11(1H, d, J=7.2 Hz), 8.13(1H, d, J=8.7 Hz), 8.49(1H, d, J=1.8 H).

Example 65

(Compound 3-12); Yield: 88.2%

(DMSO-$d_6$): δ 2.45(3H, 9), 7.00(1H, t, J=7.2 Hz), 7.11-7.14(2H, m), 7.18-7.23 (2H, m), 7.49(1H, d, J=7.5 Hz), 7.67 (1H, t, J=8.1 Hz), 7.81(1H, dd, J=9.0, 1.5 Hz), 8.09(2H, t, J=9.0 Hz), 8.51(1H, d, J=1.5 Hz), 10.46(1H, s).

Example 66

(Compound 3-13); Yield: 76.7%

(DMSO-$d_6$): δ 2.40(3H, s), 2.68(2H, t, J=7.5 Hz), 2.98-3.05(2H, m), 7.12-7.25(5H, m), 7.50(1H, dd, J=7.5, 0.9 Hz), 7.69(1H, t, J=7.2 Hz), 7.85(1H, dd, J=9.0, 1.8 Hz), 7.89(1H, t, J=5.7 Hz), 8.09-8.14(2H, m), 8.50(1H, d, J=1.5 Hz).

Example 67

(Compound 3-14); Yield: 96.0%

(CD$_3$OD): δ 1.34(3H, d, J=7.2 Hz), 2.45(3H, s), 4.47(1H, q, J=6.9 Hz), 6.86-6.92(1H, m), 6.94-6.99(2H, m), 7.02-7.06 (2H, m), 7.38(1H, dd, J=7.8, 1.2 Hz), 7.57(1H, t, J=7.8 Hz), 7.70(1H, dd, J=8.7, 1.8 Hz), 7.77(1H, d, J=8.1 Hz), 7.88(1H, d, J=9.0 Hz), 8.16(1H, d, J=1.8 Hz).

Example 68

(Compound 3-15); Yield: 87.2%

(DMSO-$d_6$): δ 2.50(3H, s), 2.61(3H, s), 4.22(2H, s), 7.31-7.40(5H, m), 7.55(1H, d, J=7.5 Hz), 7.74(1H, t, J=7.8 Hz), 7.91(1H, dd, J=8.7, 1.5 Hz), 8.18(1H, d, J=8.4 Hz), 8.19(1H, d, J=9.0 Hz), 8.64(1H, d, J=1.5 Hz).

Example 69

Preparation of
N-benzyl-5-hydroxynaphthalene-2-sulfonamide
(Compound No. 4-1)

Ethanol (3 ml) and 2N aqueous sodium hydroxide (0.1 ml) were added to 5-acetyloxy-N-benzylnaphthalene-2-sulfonamide (Compound No. 3-1; 62.0 mg, 0.17 mmol), and the mixture was stirred at room temperature for 5 minutes. The reaction mixture was poured into diluted hydrochloric acid and extracted with ethyl acetate. After the organic layer was washed with saturated brine, dried over anhydrous sodium sulfate, the residue obtained by evaporation of the solvent under reduced pressure was purified by column chromatography on silica gel (eluent; n-hexane: ethyl acetate=1:1) to give the title compound as a yellow white crystal (53.3 mg, 100%).

$^1$H-NMR(DMSO-$d_6$): δ 4.01(2H, d, J=6.3 Hz), 7.04(1H, dd, J=7.5, 1.2 Hz), 7.18-7.31(5H, m), 7.46(1H, dd, J=8.1, 7.5 Hz), 7.55(1H, d, J=8.4 Hz), 7.75(1H, dd, J=8.7, 1.8 Hz), 8.21(1H, t, J=6.3 Hz), 8.27(1H, d, J=9.0 Hz), 8.32(1H, d, J=1.8 Hz), 10.45(1H, s).

Example 70 to Example 83

The following compounds were prepared in the same manner as the method of Example 69. The compounds prepared in Example 55 to Example 68 were used as the law materials.

Example 70

(Compound 4-2); Yield: 69.5%

(DMSO-$d_6$): δ 4.08(2H, s), 7.04(1H, dd, J=7.5, 1.2 Hz), 7.36(1H, dd, J=8.4, 2.4 Hz), 7.43-7.49(3H, m), 7.54(1H, d, J=7.8 Hz), 7.74(1H, dd, J=8.7, 1.5 Hz), 8.26-8.34(3H, m), 10.48(1H, s).

Example 71

(Compound 4-3); Yield: 87.8%

(DMSO-$d_6$): δ 4.20(2H, d, J=6.0 Hz), 7.03(1H, d, J=7.2 Hz), 7.42-7.55(3H, m), 7.72(2H, t, J=7.5 Hz), 7.99(1H, d, J=5.7 Hz), 8.10(1H, s), 8.25(1H, d, J=9.0 Hz), 8.28(1H, s), 8.45(1H, t, 6.0 Hz), 10.45(1H, s).

Example 72

(Compound 4-4); Yield: 99.4%

(CDCl$_3$): δ 1.24(9H, s), 4.25(2H, d, J=6.0 Hz), 4.74(1H, t, J=6.0 Hz), 5.83(1H, s), 6.98(1H, dd, J=7.5, 0.9 Hz), 7.10(2H, d, J=8.4 Hz), 7.25(2H, d, J=8.4 Hz), 7.42(1H, dd, J=8.1, 7.8 Hz), 7.52(1H, d, J=8.4 Hz), 7.79(1H, dd, J=8.7, 2.1 Hz), 8.31(1H, d, J=8.7 Hz), 8.37(1H, d, J=2.1 Hz).

Example 73

(Compound 4-5); Yield: 92.4%

(DMSO-$d_6$): δ 4.13(1H, d, J=3.3 Hz), 7.04(1H, dd, J=7.5, 1.2 Hz), 7.43-7.49(3H, m), 7.53(1H, d, J=7.8 Hz), 7.60(2H, d, J=8.4 Hz), 7.74(1H, dd, J=9.0, 1.8 Hz), 8.27(1H, d, J=9.0 Hz), 8.29(1H, d, J=1.8 Hz), 8.36(1H, bs), 10.46(1H, bs)

Example 74

(Compound 4-6); Yield: 67.3%

(DMSO-$d_6$): δ 3.61(3H, s), 3.74(3H, s), 3.99(2H, d, J=6.3 Hz), 6.86-6.91(2H, m), 6.70(1H, dd, J=8.1, 7.2 Hz), 7.04(1H, dd, J=7.2, 1.2 Hz), 7.46(1H, dd, J=8.4, 7.2 Hz), 7.55(1H, d, J=8.1 Hz), 7.76(1H, dd, J=9.0, 2.1 Hz), 8.07(1H, t, J=6.3 Hz), 8.28(1H, d, J=8.7 Hz), 8.31(1H, d, J=1.8 Hz), 10.45(1H, s).

Example 75

(Compound 4-7); Yield: 88.9%

(DMSO-$d_6$): δ 3.82(2H, d, J=6.3 Hz), 5.05(2H, s), 6.36 (1H, d, J=7.5 Hz), 6.40-6.43(1H, m), 6.51(1H, s), 6.90(1H, t, J=7.8 Hz), 7.04(1H, dd, J=7.8, 1.2 Hz), 7.46(1H, t, J=7.8 Hz), 7.56(1H, d, J=8.1 Hz), 7.77(1H, dd, J=8.7, 1.5 Hz), 8.07(1H, t, J=6.3 Hz), 8.29(1H, d, J=8.7 Hz), 8.33(1H, d, J=1.8 Hz), 10.46(1H, s).

Example 76

(Compound 4-8); Yield: 95.0%

(DMSO-$d_6$): δ 4.44(2H, d, J=6.0 Hz), 7.05(1H, d, J=7.5 Hz), 7.38-7.47(3H, m), 7.50-7.58(3H, m), 7.80-7.84(2H, m), 7.91(1H, dd, J=6.3, 3.6 Hz), 8.08(1H, dd, J=6.3, 3.6 Hz), 8.23(1H, t, J=6.0 Hz), 8.30(1H, d, J=9.0 Hz), 8.39(1H, d, J=1.8 Hz), 10.48(1H, s).

Example 77

(Compound 4-9); Yield: 86.7%

(DMSO-$d_6$): δ 1.94(3H, s), 3.98(2H, d, J=6.0 Hz), 5.80 (1H, d, J=1.8 Hz), 6.01(1H, d, J=2.7 Hz), 7.02(1H, d, J=7.5 Hz), 7.45(1H, t, J=7.5 Hz), 7.53(1H, d, J=8.1 Hz), 7.70(1H, dd, J=9.0, 1.8 Hz), 8.17(1H, t, J=6.0 Hz), 8.24(1H, d, J=8.7 Hz), 8.25(1H, s), 1H, s).

Example 78

(Compound 4-10); Yield: 90.5%

(DMSO-$d_6$): δ 4.12(2H, d, J=6.0 Hz), 7.04(1H, dd, J=7.5, 0.9 Hz), 7.19(1H, dd, J=6.6, 4.8 Hz), 7.38(1H, d, J=8.1 Hz), 7.46(1H, t, J=8.1 Hz), 7.55(1H, d, J=8.4 Hz), 7.70(1H, td, J=7.8, 1.8 Hz), 7.76(1H, dd, J=9.0, 1.8 Hz), 8.27(1H, d, J=9.0 Hz), 8.32(1H, d, J=1.8 Hz), 8.35(1H, t, J=6.3 Hz), 8.40(1H, dd, J=4.8, 0.9 Hz), 10.47(1H, s).

Example 79

(Compound 4-11); Yield: 79.7%

(DMSO-$d_6$): δ 0.73-0.88(2H, m), 1.03-1.15(3H, m), 1.38 (1H, m), 1.50-1.69(5H, m), 2.59(2H, t, J=6.3 Hz), 7.03(1H, d, J=6.9 Hz), 7.45(1H, t, J=7.5 Hz), 7.56(1H, d, H=8.1), 7.65 (1H, t, J=6.0 Hz), 7.74(1H, dd, J=8.7, 1.8 Hz), 8.28(1H, d, J=8.7 Hz), 8.30(1H, s), 10.46(1H, s).

Example 80

(Compound 4-12); Yield: 94.3%

(DMSO-$d_6$): δ 6.96-7.03(2H, m), 7.10-7.13(2H, m), 7.17-7.22(2H, m), 7.43(1H, t, J=8.1 Hz), 7.52(1H, d, J=8.4 Hz), 7.69(1H, dd, J=9.0, 1.8 Hz), 8.23(1H, d, J=9.0 Hz), 8.30(1H, d, J=1.5 Hz), 10.35(1H, s), 10.47(1H, s).

Example 81

(Compound 4-13); Yield: 94.5%

(DMSO-d$_6$): δ 2.67(2H, t, J=7.5 Hz), 2.96-3.03(2H, m), 7.03(1H, d, J=7.5 Hz), 7.12-7.26(5H, m), 7.45(1H, t, J=7.8 Hz), 7.56(1H, d, J=8.4 Hz), 8.28(1H, d, J=8.7 Hz), 8.31(1H, d, J=1.2 Hz), 10.47(1H, s).

Example 82

(Compound 4-14); Yield: 89.8%

(DMSO-d$_6$): δ 1.19(3H, d, J=6.9 Hz), 4.40(1H, m), 7.01 (1H, dd, J=6.9, 1.8 Hz), 7.07(1H, tt, J=6.9, 1.8 Hz), 7.10-7.23 (4H, m), 7.39-7.48(2H, m), 7.66(1H, dd, J=8.7, 2.1 Hz), 8.18(1H, d, J=8.7 Hz), 8.19(1H, d, J=2.7 Hz), 8.26(1H, d, J=8.1 Hz), 10.41(1H, s).

Example 83

(Compound 4-15); Yield: 89.8%

(DMSO-d$_6$): δ 2.59(3H, s), 4.20(2H, s), 7.08(1H, dd, J=8.7, 0.9 Hz), 7.28-7.40(5H, m), 7.50(1H, t, J=8.4 Hz), 7.64(1H, d, J=8.1 Hz), 7.79(1H, dd, J=8.7, 1.5 Hz), 8.36(1H, d, J=8.7 Hz), 8.43(1H, d, J=1.8 Hz), 10.54(1H, s).

Example 84

Preparation of
5-acetylamino-N-benzylnaphthalene-2-sulfonamide
(Compound No. 5-1)

(1) Preparation of
5-(acetylamino)naphthalene-2-sulfonyl chloride

This compound was prepared by the preparation method disclosed in the U.S. Pat. No. 5,378,715.

(2) Preparation of
5-acetylamino-N-benzylnaphthalene-2-sulfonamide 5-(Acetylamino)naphthalene-2-sulfonyl chloride (280 mg, 0.987 mmol) was added to benzylamine (127 mg, 1.19 mmol) and triethylamine (0.17 ml, 1.22 mmol) dissolved in tetrahydrofuran (3.0 ml), and the mixture was stirred at room temperature for 1 hour. Water (10 ml) was added to the reaction solution, and after the mixture was stirred for 10 minutes, the resulting solid was collected. The solid was washed with water and isopropyl ether to give the title compound as a light pink solid (296 mg, 84.6%).

$^1$H-NMR(DMSO-d$_6$): δ 2.21(3H, s), 4.03(2H, d, J=6.3 Hz), 7.18-7.26(5H, m), 7.64(1H, t, J=8.1 Hz), 7.83-7.88(2H, m), 7.98(1H, d, J=7.8 Hz), 8.25(1H, d, J=9.0 Hz), 8.28(1H, t, J=6.3 Hz), 8.44(1H, d, J=1.8 Hz), 10.06(1H, s).

Example 85 to Example 87

The following compounds were prepared in the same manner as the method of Example 84(2).

Example 85

(Compound 5-2); Yield: 85.7%

(DMSO-d$_6$): δ 1.18(9H, s), 2.20(3H, s), 3.98(2H, d, J=6.3 Hz), 7.13(2H, d, J=8.4 Hz), 7.24(2H, d, J=8.1 Hz), 7.62(1H, t, J=7.8 Hz), 7.80-7.86(2H, m), 7.94(1H, d, J=7.8 Hz), 8.21 (1H, t, J=6.0 Hz), 8.22(1H, d, J=9.3 Hz), 8.38(1H, d, J=1.8 Hz), 10.04(1H, s).

Example 86

(Compound 5-3); Yield: 80.7%

(DMSO-d$_6$): δ 2.21(3H, s), 3.61(3H, s), 3.73 '3H, s), 4.00 (2H, d, J=6.0 H), 6.86-6.90(2H, m), 6.97(1H, dd, J=8.4, 7.5 Hz), 7.64(1H, t, J=7.8 Hz), 7.84-7.89(2H, m), 7.97(1H, d, J=8.4 Hz), 8.13(1H, t, J=6.0 Hz), 8.25(1H, d, J=9.0 Hz), 8.43(1H, d, J=1.8 Hz), 10.06(1H, s).

Example 87

(Compound 5-4); Yield: 63.9%

(DMSO-d$_6$): δ 1.19(3H, d, J=6.9 Hz), 2.20(3H, s), 4.36-4.46(1H, m), 7.03-7.08(1H, m), 7.12-7.23(4H, m), 7.60(1H, t, J=8.1 Hz), 7.78(1H, dd, J=9.0, 2.1 Hz), 7.83(1H, d, J=7.5 Hz), 7.88(1H, d, J=7.8 Hz), 8.18(1H, d, J=8.7 Hz), 8.28(1H, d, J=1.5 Hz), 8.32(1H, d, J=8.1 Hz), 10.01(1H, s).

Example 88

Preparation of
5-amino-N-benzylnaphthalene-2-sulfonamide
(Compound No. 6-1)

5-Acetylamino-N-benzylnaphthalene-2-sulfonamide (compound No. 5-1; 175 mg, 0.494 mmol) was suspended to a mixed solvent of 1-propanol (3.0 ml) and water (1.5 ml). Concentrated hydrochloric acid (1.5 ml) was added to the suspension and the mixture was refluxed for 1 hour. After cooling to room temperature, the separated crystal was collected and washed with 1-propanol and isopropyl ether to give the title compound as a light yellow crystal (128 mg, 74.4%).

$^1$ H-NMR(DMSO-d$_6$): δ 4.03(2H, d, J=6.0 Hz), 7.17-7.27 (5H, m), 7.47(1H, d, J=6.3 Hz), 7.59(1H, t, J=7.8 Hz), 7.84-7.90(2H, m), 8.26(1H, d, J=9.0 Hz), 8.32(1H, t, J=6.3 Hz), 8.42(1H, d, J=1.5 Hz).

Example 89 to Example 91

The following compounds were prepared in the same manner as the method of Example 88. The compounds prepared in Example 85 to Example 87 were used as the law materials.

Example 89

(Compound 6-2); Yield: 74.1%

(DMSO-d$_6$): δ 1.19(9H, s), 3.99(2H, d, J=6.0 Hz), 7.15 (2H, d, J=8.7 Hz), 7.22-7.26(2H, m), 7.48(1H, d, J=7.2 Hz), 7.58(t, J=7.8 Hz), 7.83-7.90(2H, m), 8.25(1H, d, J=7.8 Hz), 8.28(1H, t, J=6.0 Hz), 8.37(1H, d, J=1.8 Hz).

Example 90

(Compound 6-3); Yield: 80.5%

(DMSO-d$_6$): δ 3.61(3H, s), 3.74(3H, s), 4.00(1H, d, J=5.7 Hz), 6.87-6.91(2H, m), 6.96(1H, d, J=7.2 Hz), 7.45(1H, d,

J=7.5 Hz), 7.59(1H, t, J=7.8 Hz), 7.83-7.90(2H, m), 8.17(1H, t, J=6.0 Hz), 8.26(1H, d, J=9.3 Hz), 8.41(1H, d, J=1.5 Hz).

Example 91

(Compound 6-4); Yield: 73.3%

(DMSO-$d_6$): δ 1.19(3H, d, J=7.2 Hz), 4.37-4.47(1H, m), 7.02-7.08(1H, m), 7.12-7.23(4H, m), 7.37(1H, d, J=7.2 Hz), 7.53(1H, t, J=7.8 Hz), 7.70(1H, d, J=8.1 Hz), 7.76(1H, dd, J=8.7, 1.8 Hz), 8.16(1H, d, J=9.3 Hz), 8.24(1H, d, J=1.8 Hz), 8.34(1H, d, J=8.4 Hz).

Example 92

Preparation of 6-acetylamino-N-benzylnaphthalene-1-sulfonamide (Compound No. 7-1)

(1) Preparation of 6-(acetylamino)naphthalene-1-sulfonyl chloride

This compound was prepared by the preparation method disclosed in the U.S. Pat. No. 5,378,715.

(2) Preparation of 6-acetylamino-N-benzylnaphthalene-1-sulfonamide 6-(Acetylamino)naphthalene-1-sulfonyl chloride (280 mg, 0.987 mmol) was added to a solution of benzylamine (127 mg, 1.19 mmol) and triethylamine (0.17 ml, 1.22 mmol) in tetrahydrofuran (3.0 ml), and the mixture was stirred at room temperature for 1 hour. Water (10 ml) was added to the reaction solution, and after the mixture was stirred for 10 minutes, the resulting solid was collected. The solid was washed with water and a mixed solvent of ethyl acetate/isopropyl ether (1/1) to give the title compound as a white solid (284 mg, 81.1%).
$^1$H-NMR(DMSO-$d_6$): δ 2.13(3H, s), 4.01(1H, d, J=6.3 Hz), 7.13-7.20(5H, m), 7.54(1H, t, J=7.8 Hz), 7.71(1H, dd, J=9.3, 2.1 Hz), 7.97(1H, dd, J=7.5, 1.2 Hz), 8.08(1H, d, J=8.4 Hz), 8.43-8.47(2H, m), 8.58(1H, d, J=9.3 Hz), 10.30(1H, s).

Example 93 and Example 94

The following compounds were prepared in the same manner as the method of Example 92(2).

Example 93

(Compound 7-2); Yield: 88.4%

(DMSO-$d_6$): δ 1.20(9H, s), 2.13(3H, s), 3.96(2H, d, J=5.7 Hz), 7.01(2H, d, J=8.1 Hz), 7.15(2H, d, J=8.4 Hz), 7.52(1H, t, J=7.8 Hz), 7.70(1H, dd, J=9.3, 2.1 Hz), 7.94(1H, dd, J=7.2, 0.9 Hz), 8.05(1H, d, J=7.8 Hz), 8.37(1H, t, J=6.0 Hz), 8.42(1H, d, J=1.8 Hz), 8.56(1H, d, J=9.3 Hz), 10.29(1H, s).

Example 94

(Compound 7-3); Yield: 84.8%

(DMSO-$d_6$): δ 2.13(3H, s), 3.55(3H, s), 3.74(3H, s), 4.00(2H, d, J=6.0 Hz), 6.78(1H, dd, J=5.7, 3.9 Hz), 6.86-6.89(2H, m), 7.55(1H, t J=7.8 Hz), 7.71(1H, dd, J=9.3, 2.1 Hz), 7.98(1H, dd, J=7.5, 1.2 Hz), 8.09(1H, d, J=8.7 Hz), 8.29(1H, t, J=6.0 Hz), 8.44(1H, d, J=1.8 Hz), 8.60(1H, d, J=9.0 Hz), 10.30(1H, s).

Example 95

Preparation of 6-amino-N-benzylnaphthalene-1-sulfonamide hydrochloride (Compound No. 8-1)

6-Acetylamino-N-benzylnaphthalene-1-sulfonamide (compound No. 7-1; 188 mg, 0.530 mmol) was suspended to a mixed solvent of 1-propanol (3.0 ml) and water (1.5 ml). Concentrated hydrochloric acid (1.5 ml) was added to the suspension and the mixture was refluxed for 1 hour. After cooling to room temperature, the separated crystal was collected and washed with 1-propanol and isopropyl ether to give the title compound as a light yellow crystal (118 mg, 63.8%).
$^1$H-NMR(DMSO-$d_6$): δ 4.02(2H, d, J=6.3 Hz), 7.13-7.20(5H, m), 7.49(1H, dd, J=9.0, 2.4 Hz), 7.57(1H, t, J=7.8 Hz), 7.69(1H, d, J=1.8 Hz), 7.99(1H, dd, J=7.5, 1.2 Hz), 8.53(1H, t, J=6.0 Hz), 8.63(1H, d, J=9.0 Hz).

Example 96 and Example 97

The following compounds were prepared in the same manner as the method of Example 88. The compounds prepared in Example 93 and Example 94 were used as the law materials.

Example 96

(Compound 8-2); Yield: 35.4%

(DMSO-$d_6$): δ 1.21(9H, s), 3.97(2H, d, J=6.0 Hz), 7.04(2H, d, J=8.1 Hz), 7.17(2H, d, J=8.4 Hz), 7.42(1H, dd, J=8.7, 2.4 Hz), 7.52(1H, t, J=7.8 Hz), 7.56(1H, bs), 7.9(1H, dd, J=7.2, 0.9 Hz), 8.04(1H, d, J=8.4 Hz), 8.42(1H, t, J=6.0 Hz), 8.58(1H, d, J=9.3 Hz).

Example 97

(Compound 8-3); Yield: 39.8%

(DMSO-$d_6$): δ 3.55(3H, s), 3.74(3H, s), 4.01(2H, d, J=6.0 Hz), 6.79(1H, dd, J=6.0, 3.3 Hz), 6.86-6.90(2H, m), 7.45(1H, dd, J=9.3, 2.1 Hz), 7.58(1H, t, J=7.8 Hz), 7.64(1H, bs), 7.98(1H, dd, J=7.5, 0.9 Hz), 8.10(1H, d, J=8.4 Hz), 8.35(1H, t, J=6.0 Hz), 8.63(1H, d, J=9.3 Hz).

Example 98

Preparation of 6-acetylamino-N-benzylnaphthalene-2-sulfonamide (Compound No. 9-1)

(1) Preparation of 6-(acetylamino)naphthalene-2-sulfonyl chloride

This compound was prepared by the preparation method disclosed in the U.S. Pat. No. 5,378,715.

(2) Preparation of 6-acetylamino-N-benzylnaphthalene-2-sulfonamide 6-(Acetylamino)naphthalene-2-sulfonyl chloride (280 mg, 0.987 mmol) was added to a solution of benzylamine (127 mg, 1.19 mmol) and triethylamine (0.17 ml, 1.22 mmol) in tetrahydrofuran (3.0 ml), and the mixture was stirred at room temperature for 1 hour. Water (10 ml) was added to the reaction solution, and after the mixture was stirred for 10 minutes, the resulting solid was collected. The solid was washed with water and a mixed solvent of ethyl acetate/isopropyl ether (1/1) to give the title compound as a white solid (307 mg, 87.7%).

¹H-NMR(DMSO-d₆): δ 2.14(3H, s), 4.00(2H, d, J=6.3 Hz), 7.17-7.25(5H, m), 7.68(1H, dd, J=8.7, 1.8 Hz), 7.76(1H, dd, J=8.4, 1.8 Hz), 7.99(1H, d, J=9.0 Hz), 8.07(1H, d, J=9.0 Hz), 8.16(1H, t, J=6.3 Hz), 8.33(1H, d, J=1.8 Hz), 8.42(1H, d, J=1.5 Hz), 10.33(1H, s).

Example 99 and Example 100

The following compounds were prepared in the same manner as the method of Example 98(2).

Example 99

(Compound 9-2); Yield: 84.7%

(DMSO-d₆): δ 1.19(9H, s), 2.13(3H, s), 3.96(2H, d, J=6.0 Hz), 7.13(2H, d, J=8.7 Hz), 7.22(2H, d, J=8.4 Hz), 7.67(1H, dd, J=8.7, 1.8 Hz), 7.73(1H, dd, J=8.4, 1.8 Hz), 7.96(1H, d, J=9.0 Hz), 8.04(1H, d, J=9.0 Hz), 8.13(1H, t, J=6.3 Hz), 8.28(1H, d, J=1.8 Hz), 8.41(1H, d, J=1.5 Hz), 10.32(1H, s).

Example 100

(Compound 9-3); Yield: 88.5%

(DMSO-d₆): δ 2.13(3H, s), 3.60(3H, s), 3.74(3H, s), 3.99 (2H, d, J=6.0 Hz), 6.85-6.90(2H, m), 6.96(1H, dd, J=8.4, 7.2 Hz), 7.68(1H, dd, J=8.7, 1.8 Hz), 7.77(1H, dd, J=8.7, 1.8 Hz), 7.98-8.08(3H, m), 8.32(1H, d, J=1.2 Hz), 8.42(1H, d, J=1.2 Hz), 10.33(1H, s).

Example 101

Preparation of 6-amino-N-benzylnaphthalene-2-sulfonamide hydrochloride (Compound No. 10-1)

6-Acetylamino-N-benzylnaphthalene-2-sulfonamide (compound No. 9-1; 185 mg, 0.522 mmol) was suspended to a mixed solvent of 1-propanol (3.0 ml) and water (1.5 ml). Concentrated hydrochloric acid (1.5 ml) was added to the suspension and the mixture was refluxed for 1 hour. After cooling to room temperature, the separated crystal was collected and washed with 1-propanol and isopropyl ether to give the title compound as a light yellow crystal (135 mg, 74.2%).

¹H-NMR(DMSO-d₆): δ 3.99(2H, d, J=5.7 Hz), 7.12-7.25 (5H, m), 7.35(1H, d, J=9.0 Hz), 7.46(1H, s), 7.75(1H, d, J=8.7 Hz), 7.93(1H, d, J=8.7 Hz), 8.04(1H, d, J=8.7 Hz), 8.18(1H, t, J=6.3 Hz), 8.31(1H, s).

Example 102 and Example 103

The following compounds were prepared in the same manner as the method of Example 88. The compounds prepared in Example 99 and Example 100 were used as the law materials.

Example 102

(Compound 10-2); Yield: 78.1%

(DMSO-d₆): δ 1.19(9H, s), 3.99(2H, d, J=6.0 Hz), 7.15 (2H, d, J=8.7 Hz), 7.22-7.26(2H, m), 7.48(1H, d, J=7.2 Hz), 7.58(1H, t, J=7.8 Hz), 7.83-7.90(2H, m), 8.25(2H, d, J=8.4 Hz), 8.37(1H, d, J=1.8 Hz).

Example 103

(Compound 10-3); Yield: 67.3%

(DMSO-d₆): δ 3.60(3H, s), 3.73(3H, s), 3.98(2H, d, J=5.4 Hz), 6.86-6.99(3H, m), 7.36(1H, d, J=8.7 Hz), 7.47(1H, s), 7.76(1H, dd, J=8.7, 1.8 Hz), 7.94(1H, d, J=8.7 Hz), 8.02-8.06 (2H, m), 8.31(1H, s)

Example 104

Preparation of 5-amino-N-benzylnaphthalene-1-carboxamide (Compound No. 11-1)

(1) Preparation of 5-nitronaphthalene-1-carboxylic acid

This compound was prepared by the preparation method disclosed in Tetrahedron, volume 49, No. 17, pp. 3655-3663 (published in 1993).

(2) Preparation of N-benzyl-5-nitronaphthalene-1-carboxamide

Triethylamine (0.16 ml, 1.15 mmol) and ethyl chloroformate (0.11 ml, 1.115 mmol) were added to a suspension of 5-nitronaphthalene-1-carboxylic acid (250 mg, 1.15 mmol) and anhydrous tetrahydrofuran (3 ml) under ice cooling, and the mixture was stirred for 0.5 hour. Benzylamine (0.13 ml, 1.20 mmol) was added to the reaction mixture and the mixture was stirred at room temperature for 6 hours. Water was added to the reaction solution, and after the mixture was stirred for 10 minutes, the resulting precipitate was collected. The precipitate was washed with water and isopropyl ether, and dried to give the title compound as a light brown solid (189 mg, 53.5%).

¹H-NMR(DMSO-d₆): δ 4.57(2H, d, J=6.0 Hz), 7.26-7.31 (1H, m), 7.34-7.44(4H, m), 7.77(1H, dd, J=8.4, 7.8 Hz), 7.84-7.85(2H, m), 8.33(1H, dd, J=7.5, 0.9 Hz), 8.36-8.41(1H, m), 8.55(1H, d, J=8.7 Hz), 9.28(1H, t, J=6.0 Hz).

(3) Preparation of 5-amino-N-benzylnaphthalene-1-carboxamide

5% Palladium on carbon (14 mg) was added to a suspension of N-benzyl-5-nitronaphthalene-1-carboxamide (128.0 mg, 0.418 mmol) in methanol (2.5 ml). The mixture was stirred at room temperature for 2 hours, under hydrogen atmosphere. After the palladium on carbon was filtered off, the filtrate was concentrated. The residue was solidified by a mixture of isopropyl ether: ethyl acetate (1:1), and the resulting solid was washed with isopropyl ether and dried to give the title compound as a light yellow solid (102 mg, 88.7%).

¹H-NMR(DMSO-d₆): δ 4.51(2H, d, J=6.0 Hz), 5.77(2H, s), 6.70(1H, dd, J=7.5, 1.2 Hz), 7.19-7.40(8H, m), 7.49(1H, dd, J=7.2, 1.2 Hz), 8.15(1H, d, J=8.1 Hz), 8.95(1H, t, J=6.0 Hz).

Example 105

Preparation of 5-amino-N-[4-(tert-butyl)benzyl] naphthalene-1-carboxamide (Compound No. 11-2)

(1) Preparation of N-[4-(tert-butyl)benzyl]-5-nitronaphthalene-1-carboxamide

Using 5-nitronaphthalene-1-carboxylic acid (197 mg, 0.907 mmol) and 4-tert-butylbenzylamine (107 mg, 0.998 mmol), the same operation as the Example 104(2) gave the title compound as a light yellow solid (140 mg, 42.6%).

¹H-NMR(CDCl₃): δ 1.32(9H, s), 4.72(1H, d, J=5.4 Hz), 6.29(1H, s), 7.34(2H, d, J=8.7 Hz), 7.42(2H, d, J=8.4 Hz), 7.64(1H, dd, J=8.7, 7.2 Hz), 7.68(1H, dd, J=8.7, 7.2 Hz), 7.74(1H, dd, J=7.2, 1.5 Hz), 8.24(1H, dd, J=7.5, 1.2 Hz), 8.60(1H, dt, J=7.5, 1.5 Hz), 8.71(1H, dt, J=8.4, 1.2 Hz).

(2) Preparation of 5-amino-N-[4-(tert-butyl)benzyl]naphthalene-1-carboxamide Using N-[4-(tert-butyl)benzyl]-5-nitronaphthalene-1-carboxamide (140 mg, 0.386 mmol), the same operation as the Example 104(3) gave the title compound as a yellow solid (97 mg, 75.8%).

$^1$H-NMR(DMSO-$d_6$): δ 1.28(9H, s), 4.47(2H, d, J=6.0 Hz), 6.71(1H, dd, J=7.5, 0.9 Hz), 7.22(1H, dd, J=8.4, 7.5 Hz), 7.30(2H, d, J=8.4 Hz), 7.33-7.41(2H, m), 7.38(2H, d, J=8.4 Hz), 7.48(1H, dd, J=6.9, 1.2 Hz), 8.14(1H, d, J=8.7 Hz), 8.91(1H, t, J=6.0 Hz).

Example 106

Preparation of 5-amino-N-(2,3-dimethoxybenzyl)naphthalene-1-carboxamide (Compound No. 11-3)

(1) Preparation of N-(2,3-dimethoxybenzyl)-5-nitronaphthalene-1-carboxamide Using 5-nitronaphthalene-1-carboxylic acid (250 mg, 1.15 mmol) and 2,3-dimethoxybenzylamine (0.18 ml, 1.20 mmol), the same operation as the Example 104(2) gave the title compound as a gray white solid (232 mg, 55.0%).

$^1$H-NMR(DMSO-$d_6$): δ 3.81(3H, s), 3.82(3H, s), 4.58(2H, d, J=6.0 Hz), 6.98-7.00(2H, m), 7.09(1H, dd, J=8.7, 6.9 Hz), 7.70(1H, dd, 8.4, 7.8 Hz), 7.83-7.85(2H, m), 8.33(1H, dd, J=7.5, 1.2 Hz), 8.36-8.40(1H, m), 8.55(1H, dt, J=8.4, 0.9 Hz), 9.15(1H, t, J=6.0 Hz).

(2) Preparation of 5-amino-N-(2,3-dimethoxybenzyl)naphthalene-1-carboxamide Using N-(2,3-dimethoxybenzyl)-5-nitronaphthalene-1-carboxamide (168 mg, 0.459 mmol), the same operation as the Example 104(3) gave the title compound as a light pink solid (147 mg, 95.4%).

$^1$H-NMR(DMSO-$d_6$): δ 3.79(3H, s), 3.81(3H, s), 4.52 (2H.d.J=6.3 Hz), 5.78(2H, s), 6.70(1H, dd, J=7.2, 0.6 Hz), 6.95-6.99(2H, m), 7.06(1H, d, J=7.5 Hz), 7.22(1H, t, J=8.7 Hz), 7.33(1H, d, J=8.4 Hz), 7.38(1H, dd, J=8.4, 7.2 Hz), 7.49(1H, dd, J=7.2, 0.6 Hz), 8.15(1H, d, J=8.1 Hz), 8.82(1H, t, J=5.7 Hz 9).

Test Example

By using aforementioned synthetic compounds, effects on proliferation of Jurkat cells by sole administration and inhibitory effects on cell proliferation by administration in combination with bleomycin were examined. Materials and methods are as follows. Jurkat cells obtained from Dainippon Pharmaceutical Co. Ltd. were inoculated at about 10,000 cells per well in a 96 well culture plate, and incubated in 10% bovine fetal serum (Irvine Scientific) supplemented with RPMI1640 (ICN) medium in 5% $CO_2$ incubator at 37° C. For the culture, each compound was added alone, or the culture was further added with bleomycin (Wako) to give a concentration of 5 μg/ml or 10 μg/ml. 36 hours after the incubation, the number of living cells was counted by the MTS method. More specifically, 20 μl of CellTiter96™ AQueous One Solution (Promega) was added per one well, and after the cells were incubated for additional one hour, an absorbance at 490 nm was measured by using a microplate reader. The same culture added with DMSO as a solvent at final concentration of 0.25% was used as a control. The number of cells in the control was considered as 100% survival rate, and for each compound, survival rates by sole administration or a combined administration were calculated. Treatments solely with bleomycin at 5 μg/ml or 10 μg/ml gave about 5 to 10% of decrease in the survival rates of the Jurkat cells. Whilst, when the compound of the present invention coexisted, the survival rates of the Jurkat cells by bleomycin at 5 μg/ml or 10 μg/ml were remarkably decreased. The results are shown in the following table. In the table, ⌈++⌋ indicates observation of remarkable enhancement, ⌈+⌋ indicates moderated enhancement.

| Compound Number | Activity |
|---|---|
| 1-1 | ++ |
| 1-2 | + |
| 1-3 | ++ |
| 1-5 | ++ |
| 1-6 | ++ |
| 1-7 | ++ |
| 1-9 | ++ |
| 1-11 | ++ |
| 1-12 | + |
| 1-13 | + |
| 1-15 | + |
| 1-16 | + |
| 1-17 | ++ |
| 1-19 | ++ |
| 1-20 | + |
| 1-23 | + |
| 1-24 | ++ |
| 1-25 | + |
| 1-26 | ++ |
| 1-27 | + |
| 2-3 | ++ |
| 2-7 | ++ |
| 2-8 | + |
| 2-9 | + |
| 2-11 | + |
| 2-13 | + |
| 2-19 | ++ |
| 2-23 | + |
| 2-25 | + |
| 3-1 | + |
| 3-4 | ++ |
| 3-5 | + |
| 3-9 | + |
| 4-1 | + |
| 4-3 | + |
| 4-4 | ++ |
| 4-5 | + |
| 4-6 | + |
| 4-7 | + |
| 4-8 | + |
| 4-13 | + |
| 6-2 | + |
| 6-3 | + |
| 8-2 | + |
| 11-1 | + |

INDUSTRIAL APPLICABILITY

In cancer treatments based on the mode of action of DNA injury, the medicaments of the present invention have inhibitory actions against protein kinases, which are activated in the cancer cells suffered from the DNA injury, to kill said cancer cells. The medicaments of the present invention thus enhance the effect of a cancer therapy based on the mode of action of DNA injury and reduce a dose of an anticancer agent and/or radiation. Therefore, the medicaments can reduce side effects resulting from the cancer therapy.

What is claimed is:

1. A composition, which comprises as an active ingredient a substance selected from a compound represented by the following general formula (I) or a pharmacologically acceptable salt thereof:

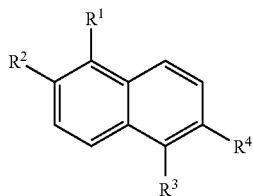

wherein one of $R^1$ and $R^2$ represents hydrogen atom and the other represents the formula —X-A wherein A represents a hydrogen atom, a hydrocarbon-carbonyl group, or a hydrocarbon-sulfonyl group, X represents an oxygen atom or NH; one of $R^3$ and $R^4$ represents hydrogen atom and the other represents the following formula:

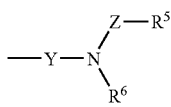

wherein
  Y represents a sulfonyl group or a carbonyl group,
  $R^5$ represents
    a phenyl group which may be substituted with one or more substituents selected from
      a halogen atom,
      a nitro group,
      an alkyl group,
      a halogenated alkyl group,
      a hydroxyl group,
      an alkoxy group,
      an alkylenedioxy group,
      an amino group,
      an N,N-di(alkyl)-amino group, and
      an alkyl-sulfonyl group,
    a naphthyl group which may be substituted,
    a furyl group which may be substituted,
    a pyridyl group which may be substituted,
    a benzimidazolyl group which may be substituted, or
    a cycloalkyl group,
  Z represents a single bond or a $C_1$ to $C_4$ alkylene group,
  $R^6$ hydrogen atom or a $C_1$ to $C_6$ alkyl group, with the following provisos:
  a compound represented by the following formula:

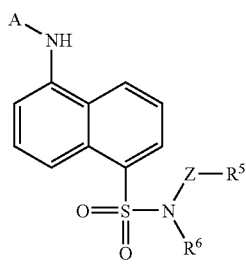

wherein each of A, Z, $R^5$ and $R^6$ has the same meaning as that defined above is excluded;

when one of $R^1$ and $R^2$ is the formula —O—A, A is a hydrogen atom, Y is a carbonyl group, Z is a single bond, and $R^6$ is hydrogen atom, then $R^5$ is
  a phenyl group which may be substituted with one or more substituents selected from
    a halogen atom,
    a nitro group,
    an alkyl group,
    a halogenated alkyl group,
    an alkoxy group,
    an alkylenedioxy group,
    an amino group,
    an N,N-di(alkyl)-amino group, and
    an alkyl-sulfonyl group,
  a naphthyl group which may be substituted,
  a furyl group which may be substituted,
  a pyridyl group which may be substituted,
  a benzimidazolyl group which may be substituted, or
  a cycloalkyl group;

when $R^2$ is the formula —NH-A, A is a hydrogen atom, Y is a sulfonyl group, Z is a $C_1$ alkylene group, and $R^6$ is hydrogen atom, then $R^5$ is
  a phenyl group which may be substituted with one or more substituents selected from
    a halogen atom,
    a nitro group,
    an alkyl group,
    a halogenated alkyl group,
    a hydroxyl group,
    an alkoxy group,
    an alkylenedioxy group,
    an amino group,
    an N,N-di(alkyl)-amino group, and
    an alkyl-sulfonyl group,
  a naphthyl group which may be substituted,
  a furyl group which may be substituted,
  a pyridyl group which may be substituted,
  a benzimidazolyl group which may be substituted, or
  a cycloalkyl group;

when $R^1$ is the formula —NH-A, A is a hydrogen atom, $R^3$ is a hydrogen atom, Y is a sulfonyl group, Z is a $C_1$ alkylene group, and $R^6$ is hydrogen atom, then $R^5$ is
  a phenyl group which may be substituted with one or more substituents selected from
    a halogen atom,
    a nitro group,
    an alkyl group,
    a halogenated alkyl group,
    a hydroxyl group,
    an alkoxy group,
    an alkylenedioxy group,
    an amino group,
    an N,N-di(alkyl)-amino group, and
    an alkyl-sulfonyl group,
  a naphthyl group which may be substituted,
  a furyl group which may be substituted,
  a pyridyl group which may be substituted,
  a benzimidazolyl group which may be substituted, or
  a cycloalkyl group; and when one of $R^1$ and $R^2$ is the formula —NH-A, A is a hydrogen atom, Y is a sulfonyl group, Z is a single bond, and $R^6$ is hydrogen atom, then $R^5$ is
  a phenyl group which is substituted with one or more substituents selected from
    a halogen atom,
    a nitro group,
    an alkyl group, a halogenated alkyl group,
a hydroxyl group,
an alkoxy group,
an alkylenedioxy group,
an amino group,
an N,N-di(alkyl)-amino group, and
an alkyl-sulfonyl group,
a naphthyl group which may be substituted,
a furyl group which may be substituted,
a pyridyl group which may be substituted, or
a benzimidazolyl group which may be substituted.

2. The composition according to claim 1, wherein Z is a methylene group, an ethylene group, an ethane-1,1-diyl group, a propane-1,3-diyl group, a propane-1,2-diyl group, a propane-2,2-diyl group, or a butane-1,4-diyl group.

3. The composition according to claim 1, wherein Y is a sulfonyl group.

4. The composition according to claim 1, wherein $R^1$ is a group represented by the formula —X-A wherein A represents a hydrogen atom, a hydrocarbon-carbonyl group, or a hydrocarbon-sulfonyl group, X represents an oxygen atom or NH, and $R^2$ is a hydrogen atom.

5. The composition according to claim 1, further comprising an anticancer agent selected from bleomycin, adriamycin, cisplatin, cyclophosphamide, mitomycin C, and derivatives thereof.

6. The composition according to claim 1, which is a specific inhibitor of a protein kinase and/or an analogous enzyme thereof.

7. A compound represented by the general formula (I) or a pharmacologically acceptable salt thereof according to claim 1, provided that the following compound is excluded:

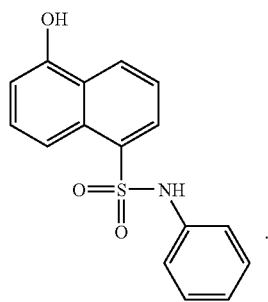

8. A compound selected from the following compounds or a pharmacologically acceptable salt thereof:
N-Benzyl-5-{[(4-methylphenyl)sulfonyl]oxy}naphthalene-1-sulfonamide;
N-(2,6-Difluorobenzyl)-5-{[(4-methylphenyl)sulfonyl]oxy}naphthalene-1-sulfonamide;
N-(2,4-Dichlorobenzyl)-5-{[(4-methylphenyl)sulfonyl]oxy}naphthalene-1-sulfonamide;
N-(3-Nitrobenzyl)-5-{[(4-methylphenyl)sulfonyl]oxy}naphthalene-1-sulfonamide;
N-(4-Nitrobenzyl)-5-{[(4-methylphenyl)sulfonyl]oxy}naphthalene--1-sulfonamide;
N-(2-Methylbenzyl)-5-{[(4-methylphenyl)sulfonyl]oxy}naphthalene-1-sulfonamide;
N-[4-(tert-Butyl)benzyl]-5-{[(4-methylphenyl)sulfonyl]oxy}naphthalene-1-sulfonamide;
N-[2-(Trifluoromethyl)benzyl]-5-{[(4-methylphenyl)sulfonyl]oxy}naphthalene-1-sulfonamide;
N-[4-(Trifluoromethyl)benzyl]-5-{[(4-methylphenyl)sulfonyl]oxy}naphthalene-1-sulfonamide;
N-(3,4-Dihydroxybenzyl)-5-{[(4-methylphenyl)sulfonyl]oxy}naphthalene-1-sulfonamide;
N-(2-Methoxybenzyl)-5-{[(4-methylphenyl)sulfonyl]oxy}naphthalene-1-sulfonamide;
N-(3-Methoxybenzyl)-5-{[(4-methylphenyl)sulfonyl]oxy}naphthalene-1-sulfonamide;
N-(2,3-Dimethoxybenzyl)-5-{[(4-methylphenyl)sulfonyl]oxy}naphthalene-1-sulfonamide;
N-(3,5-Dimethoxybenzyl)-5-{[(4-methylphenyl)sulfonyl]oxy}naphthalene-1-sulfonamide;
N-(3,4-Methylenedioxybenzyl)-5-{[(4-methylphenyl)sulfonyl]oxy}naphthalene-1-sulfonamide;
N-(3-Aminobenzyl)-5-{[(4-methylphenyl)sulfonyl]oxy}naphthalene-1-sulfonamide;
N-[4-(Dimethylamino)benzyl]-5-{[(4-methylphenyl)sulfonyl]oxy}naphthalene-1-sulfonamide;
N-[4-(Methanesulfonyl)benzyl]-5-{[(4-methylphenyl)sulfonyl]oxy}naphthalene-1-sulfonamide;
N-(1-Naphthylmethyl)-5-{[(4-methylphenyl)sulfonyl]oxy}naphthalene-1-sulfonamide;
N-[(5-Methylfuran-2-yl)methyl]-5-{[(4-methylphenyl)sulfonyl]oxy}naphthalene-1-sulfonamide;
N-[(Pyridin-2-yl)methyl]-5-{[(4-methylphenyl)sulfonyl]oxy}naphthalene-1-sulfonamide;
N-[(Benzimidazol-2-yl)methyl]-5-{[(4-methylphenyl)sulfonyl]oxy}naphthalene-1-sulfonamide;
N-Cyclohexylmethyl-5-{[(4-methylphenyl)sulfonyl]oxy}naphthalene-1-sulfonamide;
N-Phenyl-5-{[(4-methylphenyl)sulfonyl]oxy}naphthalene-1-sulfonamide;
N-(2-Phenethyl)-5-{[(4-methylphenyl)sulfonyl]oxy}naphthalene-1-sulfonamide;
N-(1-Phenethyl)-5-{[(4-methylphenyl)sulfonyl]oxy}naphthalene-1-sulfonamide;
N-Benzyl-N-methyl-5-{[(4-methylphenyl)sulfonyl]oxy}naphthalene-1-sulfonamide;
N-Benzyl-5-hydroxynaphthalene-1-sulfonamide;
N-(2,6-Difluorobenzyl)-5-hydroxynaphthalene-1-sulfonamide;
N-(2,4-Dichlorobenzyl)-5-hydroxynaphthalene-1-sulfonamide;
N-(3-Nitrobenzyl)-5-hydroxynaphthalene-1-sulfonamide;
N-(4-Nitrobenzyl)-5-hydroxynaphthalene-1-sulfonamide;
N-(2-Methylbenzyl)-5-hydroxynaphthalene-1-sulfonamide;
N-[4-(tert-Butyl)benzyl]-5-hydroxynaphthalene-1-sulfonamide;
N-[2-(Trifluoromethyl)benzyl]-5-hydroxynaphthalene-1-sulfonamide;
N-[4-(Trifluoromethyl)benzyl]-5-hydroxynaphthalene-1-sulfonamide;
N-(3,4-Dihydroxylbenzyl)-5-hydroxynaphthalene-1-sulfonamide;
N-(2-Methoxylbenzyl)-5-hydroxynaphthalene-1-sulfonamide;
N-(3-Methoxylbenzyl)-5-hydroxynaphthalene-1-sulfonamide;
N-(2,3-Dimethoxylbenzyl)-5-hydroxynaphthalene-1-sulfonamide;
N-(3,5-Dimethoxylbenzyl)-5-hydroxynaphthalene-1-sulfonamide;
N-(3,4-Methylenedioxylbenzyl)-5-hydroxynaphthalene-1-sulfonamide;
N-(3-Aminobenzyl)-5-hydroxynaphthalene-1-sulfonamide;

N-[4-(Dimethylamino)benzyl]-5-hydroxynaphthalene-1-sulfonamide;
N-[4-(Methanesulfonyl)benzyl]-5-hydroxynaphthalene-1-sulfonamide;
N-(1-Naphthylmethyl)-5-hydroxynaphthalene-1-sulfonamide;
N-[(5-Methylfuran-2-yl)methyl]-5-hydroxynaphthalene-1-sulfonamide;
N-[(Pyridin-2-yl)methyl]-5-hydroxynaphthalene-1-sulfonamide;
N-[(Benzimidazol-2-yl)methyl]-5-hydroxynaphthalene-1-sulfonamide;
N-Cyclohexylmethyl-5-hydroxynaphthalene-1-sulfonamide;
N-Phenyl-5-hydroxynaphthalene-1-sulfonamide;
N-(2-Phenethyl)-5-hydroxynaphthalene-1-sulfonamide;
N-(1-Phenethyl)-5-hydroxynaphthalene-1-sulfonamide;
N-Benzyl-N-methyl-5-hydroxynaphthalene-1-sulfonamide;
5-Acetyloxy-N-benzylnaphthalene-2-sulfonamide;
5-Acetyloxy-N-(2,4-dichlorobenzyl)naphthalene-2-sulfonamide;
5-Acetyloxy-N-(3-nitrobenzyl)naphthalene-2-sulfonamide;
5-Acetyloxy-N-[4-(tert-butyl)benzyl]naphthalene-2-sulfonamide;
5-Acetyloxy-N-[4-(trifluoromethyl)benzyl]naphthalene-2-sulfonamide;
5-Acetyloxy-N-(2,3-dimethoxybenzyl)naphthalene-2-sulfonamide;
5-Acetyloxy-N-(3-aminobenzyl)naphthalene-2-sulfonamide;
5-Acetyloxy-N-(1-naphthylmethyl)naphthalene-2-sulfonamide;
5-Acetyloxy-N-[(5-methylfuran-2-yl)methyl]naphthalene-2-sulfonamide;
5-Acetyloxy-N-[(pyridin-2-yl)methyl]naphthalene-2-sulfonamide;
5-Acetyloxy-N-(cyclohexylmethyl)naphthalene-2-sulfonamide;
5-Acetyloxy-N-phenylnaphthalene-2-sulfonamide;
5-Acetyloxy-N-(2-phenethyl)naphthalene-2-sulfonamide;
5-Acetyloxy-N-(1-phenethyl)naphthalene-2-sulfonamide;
5-Acetyloxy-N-benzyl-N-methylnaphthalene-2-sulfonamide;
N-Benzyl-5-hydroxynaphthalene-2-sulfonamide;
N-(2,4-Dichlorobenzyl)-5-hydroxynaphthalene-2-sulfonamide;
N-(3-Nitrobenzyl)-5-hydroxynaphthalene-2-sulfonamide;
N-[4-(tert-Butyl)benzyl]-5-hydroxynaphthalene-2-sulfonamide;
N-[4-(Trifluoromethyl)benzyl]-5-hydroxynaphthalene-2-sulfonamide;
N-(2,3-Dimethoxybenzyl)-5-hydroxynaphthalene-2-sulfonamide;
N-(3-Aminobenzyl)-5-hydroxynaphthalene-2-sulfonamide;
N-(1-Naphthylmethyl)-5-hydroxynaphthalene-2-sulfonamide;
N-[(5-Methylfuran-2-yl)methyl]-5-hydroxynaphthalene-2-sulfonamide;
N-[(Pyridin-2-yl)methyl]-5-hydroxynaphthalene-2-sulfonamide;
N-(Cyclohexylmethyl)-5-hydroxynaphthalene-2-sulfonamide;
N-Phenyl-5-hydroxynaphthalene-2-sulfonamide;
N-(2-Phenethyl)-5-hydroxynaphthalene-2-sulfonamide;
N-(1-Phenethyl)-5-hydroxynaphthalene-2-sulfonamide;
N-Benzyl-N-methyl-5-hydroxynaphthalene-2-sulfonamide;
5-Acetylamino-N-benzylnaphthalene-2-sulfonamide;
5-Acetylamino-N-[4-(tert-butyl)benzyl]naphthalene-2-sulfonamide;
5-Acetylamino-N-(2,3-dimethoxybenzyl)naphthalene-2-sulfonamide;
5-Acetylamino-N-benzyl-N-methylnaphthalene-2-sulfonamide;
5-Amino-N-[4-(tert-butyl)benzyl]naphthalene-2-sulfonamide;
5-Amino-N-(2,3-dimethoxybenzyl)naphthalene-2-sulfonamide;
5-Amino-N-benzyl-N-methylnaphthalene-2-sulfonamide;
6-Acetylamino-N-[4-(tert-butyl)benzyl]naphthalene-1-sulfonamide;
6-Acetylamino-N-(2,3-dimethoxybenzyl)naphthalene-1-sulfonamide;
6-Amino-N-[4-(tert-butyl)benzyl]naphthalene-1-sulfonamide;
6-Amino-N-(2,3-dimethoxybenzyl)naphthalene-1-sulfonamide;
6-Acetylamino-N-benzylnaphthalene-2-sulfonamide;
6-Acetylamino-N-[4-(tert-butyl)benzyl]naphthalene-2-sulfonamide;
6-Acetylamino-N-(2,3-dimethoxybenzyl)naphthalene-2-sulfonamide;
6-Amino-N-[4-(tert-butyl)benzyl]naphthalene-2-sulfonamide;
6-Amino-N-(2,3-dimethoxybenzyl)naphthalene-2-sulfonamide;
5-Amino-N-benzylnaphthalene-1-carboxamide;
5-Amino-N-[4-(tert-butyl)benzyl]naphthalene-1-carboxamide; and
5-Amino-N-(2,3-dimethoxybenzyl)naphthalene-1-carboxamide.

9. A composition which comprises as an active ingredient a substance selected from a compound represented by the general formula (I) or a pharmacologically acceptable salt thereof according to claim 7.

10. The composition according to claim 1, wherein $R^5$ is a substituted phenyl group.

11. The composition according to claim 1, wherein the compound is selected from the following compounds:
N-Benzyl-5-{[(4-methylphenyl)sulfonyl]oxy}naphthalene-1-sulfonamide;
N-(2,6-Difluorobenzyl)-5-{[(4-methylphenyl)sulfonyl]oxy}naphthalene-1-sulfonamide;
N-(2,4-Dichlorobenzyl)-5-{[(4-methylphenyl)sulfonyl]oxy}naphthalene-1-sulfonamide;
N-(3-Nitrobenzyl)-5-{[(4-methylphenyl)sulfonyl]oxy}naphthalene-1-sulfonamide;
N-(4-Nitrobenzyl)-5-{[(4-methylphenyl)sulfonyl]oxy}naphthalene-1-sulfonamide; N-(2-Methylbenzyl)-5-{[(4-methylphenyl)sulfonyl]oxy}naphthalene-1-sulfonamide;
N-[4-(tert-Butyl)benzyl]-5-{[(4-methylphenyl)sulfonyl]oxy}naphthalene-1-sulfonamide;
N-[2-(Trifluoromethyl)benzyl]-5-{[(4-methylphenyl)sulfonyl]oxy}naphthalene-1-sulfonamide;

N-[4-(Trifluoromethyl)benzyl]-5-{[(4-methylphenyl)sulfonyl]oxy}naphthalene-1-sulfonamide;
N-(3,4-Dihydroxybenzyl)-5-{[(4-methylphenyl)sulfonyl]oxy}naphthalene-1-sulfonamide;
N-(2-Methoxybenzyl)-5-{[(4-methylphenyl)sulfonyl]oxy}naphthalene-1-sulfonamide;
N-(3-Methoxybenzyl)-5-{[(4-methylphenyl)sulfonyl]oxy}naphthalene-1-sulfonamide;
N-(2,3-Dimethoxybenzyl)-5-{[(4-methylphenyl)sulfonyl]oxy}naphthalene-1-sulfonamide;
N-(3,5-Dimethoxybenzyl)-5-{[(4-methylphenyl)sulfonyl]oxy}naphthalene-1-sulfonamide;
N-(3,4-Methylenedioxybenzyl)-5-{[(4-methylphenyl)sulfonyl]oxy}naphthalene-1-sulfonamide;
N-(3-Aminobenzyl)-5-{[(4-methylphenyl)sulfonyl]oxy}naphthalene-1-sulfonamide;
N-[4-(Dimethylamino)benzyl]-5-{[(4-methylphenyl)sulfonyl]oxy}naphthalene-1-sulfonamide;
N-[4-(Methanesulfonyl)benzyl]-5-{[(4-methylphenyl)sulfonyl]oxy}naphthalene-1-sulfonamide;
N-(1-Naphthylmethyl)-5-{[(4-methylphenyl)sulfonyl]oxy}naphthalene-1-sulfonamide;
N-[(5-Methylfuran-2-yl)methyl]-5-{[(4-methylphenyl)sulfonyl]oxy}naphthalene-1-sulfonamide;
N-[(Pyridin-2-yl)methyl]-5-{[(4-methylphenyl)sulfonyl]oxy}naphthalene-1sulfonamide;
N-[(Benzimidazol-2-yl)methyl]-5-{[(4-methylphenyl)sulfonyl]oxy}naphthalene-1-sulfonamide;
N-Cyclohexylmethyl-5-{[(4-methylphenyl)sulfonyl]oxy}naphthalene-1-sulfonamide;
N-Phenyl-5-{[(4-methylphenyl)sulfonyl]oxy}naphthalene-1-sulfonamide;
N-(2-Phenethyl)-5-{[(4-methylphenyl)sulfonyl]oxy}naphthalene-1-sulfonamide;
N-(1-Phenethyl)-5-{[(4-methylphenyl)sulfonyl]oxy}naphthalene-1-sulfonamide;
N-Benzyl-N-methyl-5-{[(4-methylphenyl)sulfonyl]oxy}naphthalene-1-sulfonamide;
N-Benzyl-5-hydroxynaphthalene-1-sulfonamide;
N-(2,6-Difluorobenzyl)-5-hydroxynaphthalene-1-sulfonamide;
N-(2,4-Dichlorobenzyl)-5-hydroxynaphthalene-1-sulfonamide;
N-(3-Nitrobenzyl)-5-hydroxynaphthalene-1-sulfonamide;
N-(4-Nitrobenzyl)-5-hydroxynaphthalene-1-sulfonamide;
N-(2-Methylbenzyl)-5-hydroxynaphthalene-1-sulfonamide;
N-[4-(tert-Butyl)benzyl]-5-hydroxynaphthalene-1-sulfonamide;
N-[2-(Trifluoromethyl)benzyl]-5-hydroxynaphthalene-1-sulfonamide;
N-[4-(Trifluoromethyl)benzyl]-5-hydroxynaphthalene-1-sulfonamide;
N-(3,4-Dihydroxylbenzyl)-5-hydroxynaphthalene-1-sulfonamide;
N-(2-Methoxylbenzyl)-5-hydroxynaphthalene-1-sulfonamide;
N-(3-Methoxylbenzyl)-5-hydroxynaphthalene-1-sulfonamide;
N-(2,3-Dimethoxylbenzyl)-5-hydroxynaphthalene-1-sulfonamide;
N-(3,5-Dimethoxylbenzyl)-5-hydroxynaphthalene-1-sulfonamide;
N-(3,4-Methylenedioxylbenzyl)-5-hydroxynaphthalene-1-sulfonamide;
N-(3-Aminobenzyl)-5-hydroxynaphthalene-1-sulfonamide;
N-[4-(Dimethylamino)benzyl]-5-hydroxynaphthalene-1-sulfonamide;
N-[4-(Methanesulfonyl)benzyl]-5-hydroxynaphthalene-1-sulfonamide;
N-(1-Naphthylmethyl)-5-hydroxynaphthalene-1-sulfonamide;
N-[(5-Methylfuran-2-yl)methyl]-5-hydroxynaphthalene-1-sulfonamide;
N-[(Pyridin-2-yl)methyl]-5-hydroxynaphthalene-1-sulfonamide;
N-[(Benzimidazol-2-yl)methyl]-5-hydroxynaphthalene-1-sulfonamide;
N-Cyclohexylmethyl-5-hydroxynaphthalene-1-sulfonamide;
N-Phenyl-5-hydroxynaphthalene-1-sulfonamide;
N-(2-Phenethyl)-5-hydroxynaphthalene-1-sulfonamide;
N-(1-Phenethyl)-5-hydroxynaphthalene-1-sulfonamide;
N-Benzyl-N-methyl-5-hydroxynaphthalene-1-sulfonamide;
5-Acetyloxy-N-benzylnaphthalene-2-sulfonamide;
5-Acetyloxy-N-(2,4-dichlorobenzyl)naphthalene-2-sulfonamide;
5-Acetyloxy-N-(3-nitrobenzyl)naphthalene-2-sulfonamide;
5-Acetyloxy-N-[4-(tert-butyl)benzyl]naphthalene-2-sulfonamide;
5-Acetyloxy-N-[4-(trifluoromethyl)benzyl]naphthalene-2-sulfonamide;
5-Acetyloxy-N-(2,3-dimethoxybenzyl)naphthalene-2-sulfonamide;
5-Acetyloxy-N-(3-aminobenzyl)naphthalene-2-sulfonamide;
5-Acetyloxy-N-(1-naphthylmethyl)naphthalene-2-sulfonamide;
5-Acetyloxy-N-[(5-methylfuran-2-yl)methyl]naphthalene-2-sulfonamide;
5-Acetyloxy-N-[(pyridin-2-yl)methyl]naphthalene-2-sulfonamide;
5-Acetyloxy-N-(cyclohexylmethyl)naphthalene-2-sulfonamide;
5-Acetyloxy-N-phenylnaphthalene-2-sulfonamide;
5-Acetyloxy-N-(2-phenethyl)naphthalene-2-sulfonamide;
5-Acetyloxy-N-(1-phenethyl)naphthalene-2-sulfonamide;
5-Acetyloxy-N-benzyl-N-methylnaphthalene-2-sulfonamide;
N-Benzyl-5-hydroxynaphthalene-2-sulfonamide;
N-(2,4-Dichlorobenzyl)-5-hydroxynaphthalene-2-sulfonamide;
N-(3-Nitrobenzyl)-5-hydroxynaphthalene-2-sulfonamide;
N-[4-(tert-Butyl)benzyl]-5-hydroxynaphthalene-2-sulfonamide;
N-[4-(Trifluoromethyl)benzyl]-5-hydroxynaphthalene-2-sulfonamide;
N-(2,3-Dimethoxybenzyl)-5-hydroxynaphthalene-2-sulfonamide;
N-(3-Aminobenzyl)-5-hydroxynaphthalene-2-sulfonamide;
N-(1-Naphthylmethyl)-5-hydroxynaphthalene-2-sulfonamide;
N-[(5-Methylfuran-2-yl)methyl]-5-hydroxynaphthalene-2-sulfonamide;

N-[(Pyridin-2-yl)methyl]-5-hydroxynaphthalene-2-sulfonamide;
N-(Cyclohexylmethyl)-5-hydroxynaphthalene-2-sulfonamide;
N-Phenyl-5-hydroxynaphthalene-2-sulfonamide;
N-(2-Phenethyl)-5-hydroxynaphthalene-2-sulfonamide;
N-(1-Phenethyl)-5-hydroxynaphthalene-2-sulfonamide;
N-Benzyl-N-methyl-5-hydroxynaphthalene-2-sulfonamide;
5-Acetylamino-N-benzylnaphthalene-2-sulfonamide;
5-Acetylamino-N-[4-(tert-butyl)benzyl]naphthalene-2-sulfonamide;
5-Acetylamino-N-(2,3-dimethoxybenzyl)naphthalene-2-sulfonamide;
5-Acetylamino-N-benzyl-N-methylnaphthalene-2-sulfonamide;
5-Amino-N-[4-(tert-butyl)benzyl]naphthalene-2-sulfonamide;
5-Amino-N-(2,3-dimethoxybenzyl)naphthalene-2-sulfonamide;
5-Amino-N-benzyl-N-methylnaphthalene-2-sulfonamide;
6-Acetylamino-N-[4-(tert-butyl)benzyl]naphthalene-1-sulfonamide;
6-Acetylamino-N-(2,3-dimethoxybenzyl)naphthalene-1-sulfonamide;
6-Amino-N-[4-(tert-butyl)benzyl]naphthalene-1-sulfonamide;
6-Amino-N-(2,3-dimethoxybenzyl)naphthalene-1-sulfonamide;
6-Acetylamino-N-[4-(tert-butyl)benzyl]naphthalene-2-sulfonamide;
6-Acetylamino-N-(2,3-dimethoxybenzyl)naphthalene-2-sulfonamide;
6-Amino-N-[4-(tert-butyl)benzyl]naphthalene-2-sulfonamide;
6-Amino-N-(2,3-dimethoxybenzyl)naphthalene-2-sulfonamide;
5-Amino-N-benzylnaphthalene-1-carboxamide;
5-Amino-N-[4-(tert-butyl)benzyl]naphthalene-1-carboxamide; and
5-Amino-N-(2,3-dimethoxybenzyl)naphthalene-1-carboxamide.

12. The composition according to claim 1, wherein the compound is N-[4-(tert-butyl)benzyl]-5-{[(4-methylphenyl)sulfonyl]oxy}naphthalene-1-sulfonamide.

13. The compound according to claim 7 or a pharmacologically acceptable salt thereof, wherein A is a hydrogen atom, an acetyl group, or a para-toluenesulfonyl group.

14. The composition according to claim 1, wherein A is a hydrogen atom, an alkyl-carbonyl group, or an aryl-sulfonyl group which may be substituted with one or more alkyl groups.

15. The composition according to claim 1, wherein A is a hydrogen atom, an acetyl group, or a para-toluenesulfonyl group.

16. The composition according to claim 1, wherein $R^5$ is a phenyl group, 2,6-difluorophenyl group, 2,4-dichlorophenyl group, 3-nitrophenyl group, 4-nitrophenyl group, 2-methylphenyl group, 4-(tert-butyl)phenyl group, 2-(trifluoromethyl)phenyl group, 4-(trifluoromethyl)phenyl group, 3,4-dihydroxyphenyl group, 2-methoxyphenyl group, 3-methoxyphenyl group, 2,3-dimethoxyphenyl group, 3,5-dimethoxyphenyl group, 3,4-methylenedioxyphenyl group, 3-aminophenyl group, 4-(dimethylamino)phenyl group, 4-methanesulfonylphenyl group, 1-naphthyl group, 5-methylfuran-2-yl group, pyridin-2-yl group, benzimidazol-2-yl group, or cyclohexyl group.

17. The compound according to claim 7 or a pharmacologically acceptable salt thereof, wherein Z is a methylene group, an ethylene group, an ethane-1,1-diyl group, a propane-1,3-diyl group, a propane-1,2-diyl group, a propane-2,2-diyl group, or a butane-1,4-diyl group.

18. The compound according to claim 7 or a pharmacologically acceptable salt thereof, wherein A is a hydrogen atom, an alkyl-carbonyl group, or an aryl-sulfonyl group which may be substituted with one or more alkyl groups.

19. The compound according to claim 7 or a pharmacologically acceptable salt thereof, wherein $R^5$ is a phenyl group, 2,6-difluorophenyl group, 2,4-dichlorophenyl group, 3-nitrophenyl group, 4-nitrophenyl group, 2-methylphenyl group, 4-(tert-butyl)phenyl group, 2-(trifluoromethyl)phenyl group, 4-(trifluoromethyl)phenyl group, 3,4-dihydroxyphenyl group, 2-methoxyphenyl group, 3-methoxyphenyl group, 2,3-dimethoxyphenyl group, 3,5-dimethoxyphenyl group, 3,4-methylenedioxyphenyl group, 3-aminophenyl group, 4-(dimethylamino)phenyl group, 4-methanesulfonylphenyl group, 1-naphthyl group, 5-methylfuran-2-yl group, pyridin-2-yl group, benzimidazol-2-yl group, or cyclohexyl group.

20. The composition according to claim 9, which is a specific inhibitor of a protein kinase and/or an analogous enzyme thereof.

21. The composition according to claim 9, which is used for reducing a side effect resulting from a cancer therapy based on a mode of action of DNA injury.

* * * * *